(12) United States Patent
Bruheim

(10) Patent No.: US 10,328,105 B2
(45) Date of Patent: Jun. 25, 2019

(54) FLOWABLE CONCENTRATED PHOSPHOLIPID KRILL OIL COMPOSITION

(71) Applicant: RIMFROST TECHNOLOGIES AS, Fosnavaag (NO)

(72) Inventor: Inge Bruheim, Volda (NO)

(73) Assignee: Rimfrost Technologies AS, Fosnavag (NO)

( * ) Notice: Subject to any disclaimer, the term of this patent is extended or adjusted under 35 U.S.C. 154(b) by 0 days.

(21) Appl. No.: 15/163,127

(22) Filed: May 24, 2016

(65) Prior Publication Data

US 2017/0020928 A1   Jan. 26, 2017

Related U.S. Application Data

(60) Provisional application No. 62/281,974, filed on Jan. 22, 2016, provisional application No. 62/166,872, filed on May 27, 2015.

(51) Int. Cl.
*A61K 35/612* (2015.01)
*A61K 31/683* (2006.01)
*A61K 9/48* (2006.01)
*A61K 31/685* (2006.01)
*A61K 45/06* (2006.01)

(52) U.S. Cl.
CPC .......... *A61K 35/612* (2013.01); *A61K 9/4825* (2013.01); *A61K 9/4858* (2013.01); *A61K 31/683* (2013.01); *A61K 31/685* (2013.01); *A61K 45/06* (2013.01)

(58) Field of Classification Search
CPC ................................................... A61K 35/612
See application file for complete search history.

(56) References Cited

U.S. PATENT DOCUMENTS

| | | | |
|---|---|---|---|
| 5,053,234 A | 10/1991 | Anderson et al. | 426/59 |
| 6,365,181 B1 | 4/2002 | Matthews | 424/451 |
| 8,030,348 B2 | 10/2011 | Sampalis et al. | 514/506 |
| 8,057,825 B2 | 11/2011 | Sampalis et al. | 424/522 |
| 8,586,567 B2 | 11/2013 | Sampalis et al. | 514/120 |
| 2012/0149867 A1 | 6/2012 | Bruheim et al. | 530/300 |
| 2013/0225794 A1 | 8/2013 | Bruheim et al. | 530/359 |
| 2014/0141074 A1 | 5/2014 | Sampalis et al. | 424/451 |
| 2014/0370115 A1 | 12/2014 | Hoem et al. | 424/522 |
| 2017/0182074 A1* | 6/2017 | Hupfeld | A61K 31/685 |

FOREIGN PATENT DOCUMENTS

| | | |
|---|---|---|
| AU | 2014 256 345 | 11/2014 |
| CN | 1948317 A | 10/2005 |
| CN | 101006824 A | 1/2007 |
| CN | 104498180 | 4/2015 |
| EP | 0 519 916 B1 | 12/1993 |
| GB | 1 572 226 | 7/1980 |
| JP | S62263192 A | 11/1987 |
| JP | 2001072693 A | 3/2001 |
| WO | WO 2008/117062 | 10/2008 |
| WO | WO 2010/136900 | 5/2010 |
| WO | WO 2010/097701 | 9/2010 |
| WO | WO 2011/050474 | 5/2011 |
| WO | WO2011/051743 | 5/2011 |
| WO | WO 2012/149867 | 8/2012 |
| WO | WO 2013/102792 | 7/2013 |
| WO | WO 2015/121378 | 8/2015 |

OTHER PUBLICATIONS

Adam Adler, et al., "Motif Module Map Reveals Enforcement of Aging by Continual NF-KappaB Activity." *Genes Dev,* 21(24):3244-3257 (2007).
Amidon, et al., "A Theoretical Basis for a Biopharmaceutic Drug Classification: The Correlation of in Vitro Drug Product Dissolution and in Vivo Bioavailability." *Pharm Res,* 12(3):413-420 (1995).
Armstrong, et al., "Drug Migration into Soft Gelatin Capsule Shells and Its Effect on in-Vitro Availability." *J Pharm Pharmacol,* 36(6):361-365 (1984).
B1151N Pharmaceutical Dosage Forms, USP 30—NF 25, pp. 620-631, 2007.
Basu, "F2-Isoprostanes in Human Health and Diseases: From Molecular Mechanisms to Clinical Implications." *Antioxid Redox Signal,* 10(8):1405-1434 (2008).
Baykara and Yüksel, "The Preparation of Prolonged Action Formulations in the Form of Semi Solid Matrix into Hard Gelatin Capsules of Oxprenolol I. Thermocap Method." *Drug development and industrial pharmacy,* 17(9):1215-1227 (1991).
Baynes, et al., "Apotransferrin Receptors and the Delivery of Iron from Cultured Human Blood Monocytes." *Am J Hematol,* 25(4):417-425 (1987).
Benameur, "Liquid and Semi-Solid Formulations for Enhancing Oral Absorption." *Bulletin Technique Gattefossé,* 99:63-75 (2006).
Bergstrom, et al., "Capsules, Soft." In: *Encyclopedia of Pharmaceutical Technology,* Marcel Dekker, New York: 317-327 (2002).
Bligh and Dyer, "A Rapid Method of Total Lipid Extraction and Purification." *Can J Biochem Physiol,* 37(8):911-917 (1959).
Bond, et al., "Cephalexin: A New Oral Broad-Spectrum Antibiotic." *Pharm. J,* 205:210-214 (1970).

(Continued)

*Primary Examiner* — Gina C Justice
(74) *Attorney, Agent, or Firm* — Medlen & Carroll, LLP

(57) ABSTRACT

The present invention is related to methods of making crustacean oil compositions. In particular, the crustacean oil compositions are krill oil compositions. In some embodiments, the krill oil compositions are concentrated in phospholipids. These concentrated phospholipid krill oil compositions have a sufficient flowability to permit successful encapsulation at phospholipid concentrations that is currently unattainable in the art. Such phospholipid krill oil compositions are capable of encapsulation even though they may have a phospholipid concentration ranging between approximately 60%-99% and a viscosity ranging between 100,000-3,000,000 cP. Such concentrated phospholipid krill oil compositions may be created using a small molecule organic solvent/water extraction mixture and/or sub-critical or super-critical fluid extraction at low temperatures followed by a drying process to remove water and organic solvent (e.g., for example, ethanol).

14 Claims, 21 Drawing Sheets

(56) References Cited

OTHER PUBLICATIONS

Bowtle, "Liquid Filling of Hard Gelatin Capsules: A New Technology for Alternative Formulations." *Pharm. Tech. Eur,* 10:84-90 (1998).
Brown, et al., "The Effect of Cross-Linking on the in Vivo Disintegration of Hard Gelatin Capsules." *Pharm Res,* 15(7):1026-1030 (1998).
Cabezas, et al., "Sunflower Lecithin: Application of a Fractionation Process with Absolute Ethanol." *Journal of the American Oil Chemists' Society,* 86(2):189-196 (2009).
Chang, et al., "A Study on Gelatin Capsule Brittleness: Moisture Transfer between the Capsule Shell and Its Content." *J Pharm Sci,* 87(5):556-558 (1998).
Charman, et al., "Self-Emulsifying Drug Delivery Systems: Formulation and Biopharmaceutic Evaluation of an Investigational Lipophilic Compound." *Pharm Res,* 9(1):87-93 (1992).
Chatham, "The Use of Bases in SSM Formulations." *STP Pharma,* 3(7):575-582 (1987).
Cole "Liquid-Filled and-Sealed Hard Gelatin Capsule Technologies." *Chapter 14.* In: Rathbone, et al., (Eds.), *Modified-Release Drug Delivery Technology,* Marcel Dekker, New York: 177-188 (2003).
Cole, et al., "In Vitro and in Vivo Pharmacoscintigraphic Evaluation of Ibuprofen Hypromellose and Gelatin Capsules." *Pharm Res,* 21(5):793-798 (2004).
Cole, et al., "Challenges and Opportunities in the Encapsulation of Liquid and Semi-Solid Formulations into Capsules for Oral Administration." *Adv Drug Deliv Rev,* 60(6):747-756 (2008).
Conway and Byrne, "LXI. An Absorption Apparatus for the Micro-Determination of Certain Volatile Substances: I. The Micro-Determination of Ammonia." *Biochem J,* 27(2):419-429 (1933).
Cuiné, et al., "Das Einbringen Viskoser Lösungen Von Aktivstoffen in Hartgelatinekapseln." *Pharm. Ind,* 40(6):654-657 (1987).
de Morais Coutinho, et al., "State of Art of the Application of Membrane Technology to Vegetable Oils: A Review." *Food Research International,* 42(5):536-550 (2009).
Dennis, et al., "In Vivo Evaluation of Rapid Release and Sustained Release Gelucire Capsule Formulations." *International Journal of Pharmaceutics,* 65(1):85-100 (1990).
Dey, et al., "The Dissolution and Bioavailability of Etodolac from Capsules Exposed to Conditions of High Relative Humidity and Temperatures." *Pharm Res,* 10(9):1295-1300 (1993).
Digenis, et al., "Cross-Linking of Gelatin Capsules and Its Relevance to Their in Vitro-in Vivo Performance." *J Pharm Sci,* 83(7):915-921 (1994).
Doelker, et al., "The Incorporation and in Vitro Release Profiles of Liquid, Deliquescent or Unstable Drugs with Fusible Excipients in Hard Gelatin Capsules." *Drug Development and Industrial Pharmacy,* 12(10):1553-1565 (1986).
Gaby, "Nutritional Therapies for Ocular Disorders: Part Three." *Altern Med Rev,* 13(3):191-204 (2008).
Ghirardi, et al., "Bioavailability of Digoxin in a New Soluble Pharmaceutical Formulation in Capsules." *J Pharm Sci,* 66(2):267-269 (1977).
Goltzman, "Discoveries, Drugs and Skeletal Disorders." *Nat Rev Drug Discov,* 1(10):784-796 (2002).
Hawley, et al., "Physical and Chemical Characterization of Thermosoftened Bases for Molten Filled Hard Gelatin Capsule Formulations." *Drug Development and Industrial Pharmacy,* 18(16):1719-1739 (1992).
Hermansdorff, et al., "Dietary Total Antioxidant Capacity Is Inversely Related to Central Adiposity as Well as to Metabolic and Oxidative Stress Markers in Healthy Young Adults." *Nutr Metab (Lond),* 8:59 (2011).
Hom, et al., "Soft Gelatin Capsules II: Oxygen Permeability Study of Capsule Shells." *J Pharm Sci,* 64(5):851-857 (1975).
Howard and Gould, "Drug Release from Thermosetting Fatty Vehicles Filled into Hard Gelatin Capsules." *Drug Development and Industrial Pharmacy,* 13(6):1031-1045 (1987).

Jones, "Manufacture and Properties of Two-Piece Hard Capsules. Chapter 4 "In: *Pharmaceutical Capsules,* Podczeck and Jones, Eds., *Pharmaceutical Press, London:* 79-100 (2004A).
Joshi, et al., "Bioavailability Enhancement of a Poorly Water-Soluble Drug by Solid Dispersion in Polyethylene Glycol-Polysorbate 80 Mixture." *Int J Pharm,* 269(1):251-258 (2004).
Joshi, et al., "Modification of Lecithin by Physical, Chemical and Enzymatic Methods." *European Journal of Lipid Science and Technology,* 108(4):363-373 (2006).
Kattige and Rowley, "Influence of Rheological Behaviour of Particulate/Polymer Dispersions on Liquid-Filling Characteristics for Hard Gelatin Capsules." *Int J Pharm,* 316(1-2):74-85 (2006).
Kontny and Mulski, "Gelatin Capsule Brittleness as a Function of Relative Humidity at Room Temperature." *International Journal of Pharmaceutics,* 54(1):79-85 (1989).
Kovarik, et al., "Reduced inter- and intraindividual variability in cyclosporin pharmacokinetics from a microemulsion formulation." J. Pharm. Sci., 83:444-446, 1994.
Kuentz and Rothlisberger, "Determination of the Optimal Amount of Water in Liquid-Fill Masses for Hard Gelatin Capsules by Means of Texture Analysis and Experimental Design." *Int J Pharm,* 236(1-2):145-152 (2002).
Kuksis, et al., "Covalent Binding of Acetone to Aminophospholipids in Vitro and in Vivo." In: Baynes, et al., Eds. Maillard Reaction: Chemistry at the interface of Nutrition, Aging and Disease. *Ann N Y Acad Sci,* 1043:417-439 New York Academy of Sciences, New York. (2005).
Lahr, "Flüssig Befüllte Hartgelatinekapseln." *Pharm. Ztg,* 131(15):88-91 (1986).
Lipinski, et al., "Experimental and Computational Approaches to Estimate Solubility and Permeability in Drug Discovery and Development Settings." *Adv Drug Deliv Rev,* 46(1-3):3-26 (2001).
Liu, et al., "Preparation of Deoiled Soy Lecithin by Ultrafiltration." *Journal of the American Oil Chemists' Society,* 88(11):1807-1812 (2011).
Lucas, et al., "Disposition of Vancomycin in Healthy Volunteers from Oral Solution and Semi-Solid Matrix Capsules." *J Clin Pharm Ther,* 12(1):27-31 (1987).
Lusas, et al., "Final Report: IPA as an Extraction Solvent." *Inform,* 8(3):290-292 (1997).
Manjula and Subramanian, "Laboratory Studies on Membrane Deoiling of Lecithin." *Journal of the American Oil Chemists' Society,* 85(6):573-580 (2008).
McTaggart, et al., "The Evaluation of an Automatic System for Filling Liquids into Hard Gelatin Capsules." *J Pharm Pharmacol,* 36(2):119-121 (1984).
"Method 937.09"; In: *Official Methods of Analysis,* 18th ed. Association of Official Analytical Chemists, Gaithersburg, MD (2005).
Method Ce 1b-89: "Fatty acid composition by GLC. Marine oils" In: Official Methods and Recommended Practices of the AOCS, 5th ed.; Firestone, Ed.; American Oil Chemists' Society Press: Champaign, IL, 1998.
Meyer, et al., "The Effect of Gelatin Cross-Linking on the Bioequivalence of Hard and Soft Gelatin Acetaminophen Capsules." *Pharm Res,* 17(8):962-966 (2000).
Ooi and Colucci, Pharmacological treatment of heart failure. In: J.G. Hardman, L.E. Limbird (Eds.), Goodman & Gilman's The pharmacological basis of therapeutics, p. 918, McGraw-Hill, New York, 2001.
Petersen, et al., "Mitochondrial Dysfunction in the Elderly: Possible Role in Insulin Resistance." *Science,* 300(5622):1140-1142 (2003).
Peterson, et al., "Skeletal Muscle Mitochondria and Aging: A Review." *J Aging Res,* 2012:1-10 (2012).
Podczek, "Technology to Manufacture Soft Capsules." Chapter 10 In: F. Podczek, B.E. Jones (Eds.), *Pharmaceutical Capsules,* Pharmaceutical Press, London, 2004, pp. 195-199, (2004).
Pouton, "Formulation of Poorly Water-Soluble Drugs for Oral Administration: Physicochemical and Physiological Issues and the Lipid Formulation Classification System." *Eur J Pharm Sci,* 29(3-4):278-287 (2006).
Reich, "Formulation and physical properties of soft capsules." Chapter 11 In: F. Podczek, B.E. Jones (Eds.), *Pharmaceutical Capsules,* Pharmaceutical Press, London, 2004, pp. 201-212.

(56) References Cited

OTHER PUBLICATIONS

Rowley, "Filling of liquids and semi-solids into hard two-piece capsules" Chapter 9 In: F. Podczek, B.E. Jones (Eds.), *Pharmaceutical Capsules*, Pharmaceutical Press, London, pp. 169-194, 2004A.
Rowley, "Filling of liquids and semi-solids into hard two-piece capsules" Chapter 9 In: F. Podczek, B.E. Jones (Eds.), *Pharmaceutical Capsules*, Pharmaceutical Press, London, pp. 169-194, 2004B.
Saeed et al., "Rheological Characteristics of Poloxamers and Poloxamer/Silicon Dioxide Gels in Relation to Liquid Filling of Hard Gelatin Capsules" *Proceedings Pharmaceutical Technology Conference (Athens)* 16:217-224 (1997).
Sahena, et al., "Application of Supercritical $CO_2$ in Lipid Extraction—a Review." *Journal of Food Engineering*, 95(2):240-253 (2009).
Schamp, et al., "Development of an in Vitro/in Vivo Correlation for Lipid Formulations of EMD50733, a Poorly Soluble, Lipophilic Drug Substance." *Eur J Pharm Biopharm*, 62(3):227-234 (2006).
Seager, "Soft Gelatin Capsules: A Solution to Many Tableting Problems." *Pharm Technol*, 9:84, 86, 88, 90, 92, 94, 96, 98, 100, 102, 104. (1985).
Rajagopal Sekhar, et al., "Deficient Synthesis of Glutathione Underlies Oxidative Stress in Aging and Can Be Corrected by Dietary Cysteine and Glycine Supplementation." *Am J Clin Nutr*, 94(3):847-853 (2011).
Seta, et al., "Design and Preparation of Captopril Sustained-Release Dosage Forms and Their Biopharmaceutical Properties." *International Journal of Pharmaceutics*, 41(3):245-254 (1988A).
Seta, et al., "Preparation and Pharmacological Evaluation of Captopril Sustained-Release Dosage Forms Using Oily Semisolid Matrix." *International Journal of Pharmaceutics*, 41(3):255-262 (1988B).
Seta, et al., "Design of Captopril Sustained-Release Preparation with Oily Semisolid Matrix Intended for Use in Human Subjects." *International Journal of Pharmaceutics*, 41(3):263-269 (1988C).
Soliman and Khan, "Preparation and in Vitro Characterization of a Semi-Solid Dispersion of Flurbiprofen with Gelucire 44/14 and Labrasol." *Pharmazie*, 60(4):288-293 (2005).
Strickley, "Solubilizing Excipients in Oral and Injectable Formulations." *Pharm Res*, 21(2):201-230 (2004).
Strickrodt, "Fully-Automatic Process for Filling High-Viscosity Pastes into Hard Gelatin Capsules." *Pharmazeutische Industrie*, 52(10):1276-1279 (1990).
Su, et al., "Study on a Novel Process for the Separation of Phospholipids, Triacylglycerol and Cholesterol from Egg Yolk." *J Food Sci Technol*, 52(7):4586-4592 (2015).
Talley, "Scope of the Problem of Functional Digestive Disorders." *Eur J Surg Suppl*(582):35-41 (1998).
Tilstra, et al., "NF-KappaB Inhibition Delays DNA Damage-Induced Senescence and Aging in Mice." *J Clin Invest*, 122(7):2601-2612 (2012).
Tsuchida, "The Role of Myostatin and Bone Morphogenetic Proteins in Muscular Disorders." *Expert Opin Biol Ther*, 6(2):147-154 (2006).
Vial-Bernasconi, et al., "In Vivo Evaluation of an Indomethacin Monolithic, Extended Zero-Order Release Hard-Gelatin Capsule Formulation Based on Saturated Polyglycolysed Glycerides." *Pharm Acta Helv*, 70(4):307-313 (1995).
Walker, et al., "The Filling of Molten and Thixotropic Formulations into Hard Gelatin Capsules." *J Pharm Pharmacol*, 32(6):389-393 (1980).
Walters and Rowley, "*Moisture Uptake of Excipients for Liquid-Filling into Hard Gelatin Capsules.*" Paper presented at the Pharmaceutical Technology Conference. Proceedings *Pharmaceutical Technology Conference* (Utrecht), 18:97-101 (1999).
Warman, et al., "Nosology and Classification of Genetic Skeletal Disorders: 2010 Revision." *Am J Med Genet A*, 155A(5):943-968 (2011).
Wilkinson and Fraunfelder, "Use of Herbal Medicines and Nutritional Supplements in Ocular Disorders: An Evidence-Based Review." *Drugs*, 71(18):2421-2434 (2011).

Wittwer, "New developments in hermetic sealing of hard gelatin capsules." *Pharm. Manuf.* 2:24-27, (1985).
Wu and Benet, "Predicting Drug Disposition Via Application of BCS: Transport/Absorption/Elimination Interplay and Development of a Biopharmaceutics Drug Disposition Classification System." *Pharm Res*, 22(1):11-23 (2005).
Yüksel, et al., "Enhanced Bioavailability of Piroxicam Using Gelucire 44/14 and Labrasol: In Vitro and in Vivo Evaluation." *European Journal of Pharmaceutics and Biopharmaceutics*, 56(3):453-459 (2003).
Zanotti and Canalis, "Notch Regulation of Bone Development and Remodeling and Related Skeletal Disorders." *Calcif Tissue Int*, 90(2):69-75 (2012).
Zhao, et al., "Cell-Permeable Peptide Antioxidants Targeted to Inner Mitochondrial Membrane Inhibit Mitochondrial Swelling, Oxidative Cell Death, and Reperfusion Injury." *J Biol Chem*, 279(33):34682-34690 (2004).
Ziegelitz, "Lecithin Processing Possibilities." *Inform*, 6(11):1224-1230 (1995).
Onemia, Acasti Products, Acasti Pharma, Inc., May 14, 2015.
Krill Oil With Repeatably Low Viscosity Rimfrost Sublime Antarctic Krill Oil, Technical Paper, pp. 1-3. Oct. 2014.
Cadé and Madit, "Liquid Filling in Hard Gelatin Capsules—Preliminary Steps." *Bulletin Technique-Gattefosse*:15-20 (1996).
Krakeli et al., "Matriksinterferenser i krillolje ved maling av vanninnhold (KF)" or "Concentration of phospolipids in krill oil by ethanol fractionation." NOFIMA notat. (2015).
Nielsen and Shukla, "In Situ Solid Phase Extraction of Lipids from Spray-Dried Egg Yolk by Ethanol with Subsequent Removal of Triacylglycerols by Cold Temperature Crystallization." *LWT-Food Science and Technology*, 37(6):613-618 (2004).
Cole, "Hartgelatinekapseln." In: *Pharmazeutische Technologie*, Georg Thieme Verlag, Stuttgart: 319-320 (1991).
Fischer, Weichgelatinekapseln, in: H. Sucker, P. Fuchs, P. Speiser (Eds.), Pharmazeutische Technologie, Georg Thieme Verlag, Stuttgart, 1991, pp. 337-347, (1991).
Bohne, et al., "A New Process for Filling Hard Gelatin Capsules with Semisolid Materials—Experiences in Development and Production." Pharmazeutische Industrie, 53(12):1127-1134 (1991). English Abstract.
Bowtle, et al., S.S.M. Formulations and Capsules: An Improved Way to Handle Toxic Compounds. Abstract PT 726. Presented at the AAPS annual meeting and exposition, Pharm. Res 7 p. 612 (1989).
Cuiné, et al., "Das Einbringen Viskoser Lösungen Von Aktivstoffen in Hartgelatinekapseln." *Pharm. Ind*, 40(6):654-657 (1987). English Abstract.
Duerr, et al., "Entwicklung Von Rezepturen Und Verfahren Zur Abfüllung Von Flüssigen Massen in Hartgelatinekapseln Unter Produktionsbedingungen." *Acta Pharm. Technol*, 29(3):245-251 (1983). English Abstract.
Hermann, "Bioverftigbarkeit zweier neuer Nifedipin-Formulierungen", Pharm. ZTG., 131:869-870, (1986). English Abstract.
Miller, et al., "[Stres oksydacyjny w stwardnieniu rozsianym] Oxidative Stress in Multiple Sclerosis]." *Pol Merkur Lekarski*, 27(162):499-502 (2009). English Abstract.
Serra, "[Clinical Research Techniques in Functional Digestive Disorders]." *Gastroenterol Hepatol*, 29(4):255-262 (2006). English Abstract.
Strickrodt, "Fully-Automatic Process for Filling High-Viscosity Pastes into Hard Gelatin Capsules." *Pharmazeutische Industrie*, 52(10):1276-1279 (1990). English Abstract.
Rowley, "Filling of liquids and semi-solids into hard two-piece capsules" Chapter 9 In: F. Podczek, B.E. Jones (Eds.), Pharmaceutical Capsules, Pharmaceutical Press, London, pp. 169-180, 2004A.
Rowley, "Filling of liquids and semi-solids into hard two-piece capsules" Chapter 9 In: F. Podczek, B.E. Jones (Eds.), Pharmaceutical Capsules, Pharmaceutical Press, London, pp. 169 (repeat), 181-194, 2004B1.
"Method 937.09" under 35.1.18 AOAC Official Method 937.09 Salt (Chlorine as Sodium Chloride) in Seafood; Chapter 35, pp. 9-10: In: *Official Methods of Analysis*, 18th ed. Association of Official Analytical Chemists, Gaithersburg, MD (2005).

(56) References Cited

OTHER PUBLICATIONS

"Method Ce 1b-89" under AOCS Official Method Ce 1b-89: "Fatty acid composition by GLC. Marine Oils", Sampling And Analysis of Commercial Fats and Oils, pp. 1-5: In: *Official Methods and Recommended Practices of the AOCS,* 5th ed.; Firestone, Ed.; American Oil Chemists' Society Press: Champaign, IL, 1998a, revised 2001.

Jones, "Manufacture and Properties of Two-Piece Hard Capsules. Chapter 4 "In: Pharmaceutical Capsules, Podczeck and Jones, Eds., Pharmaceutical Press, London: 79-87 (2004A).

Jones, "Manufacture and Properties of Two-Piece Hard Capsules. Chapter 4 "In: Pharmaceutical Capsules, Podczeck and Jones, Eds., Pharmaceutical Press, London: 88-100 (2004B).

* cited by examiner

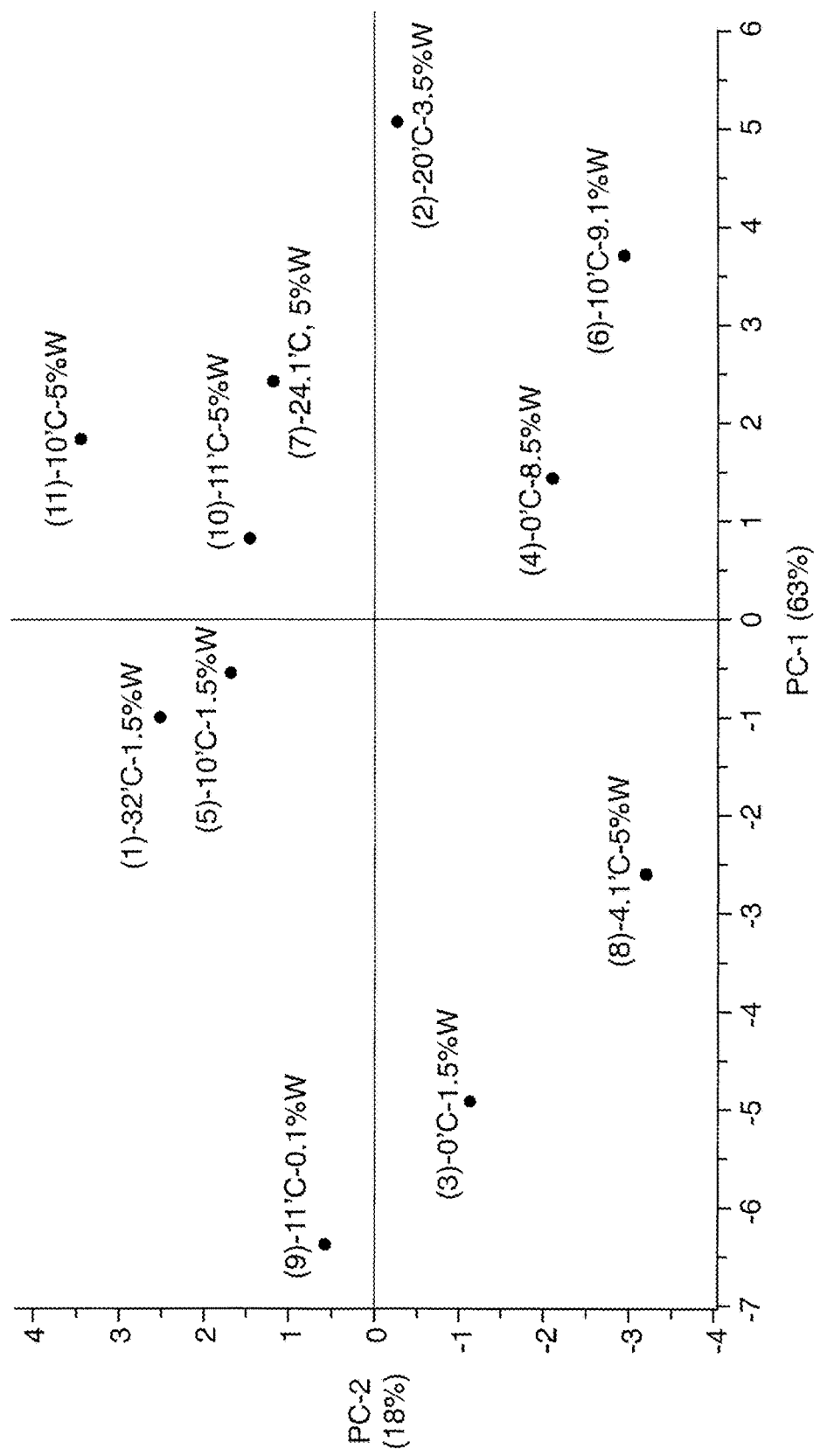

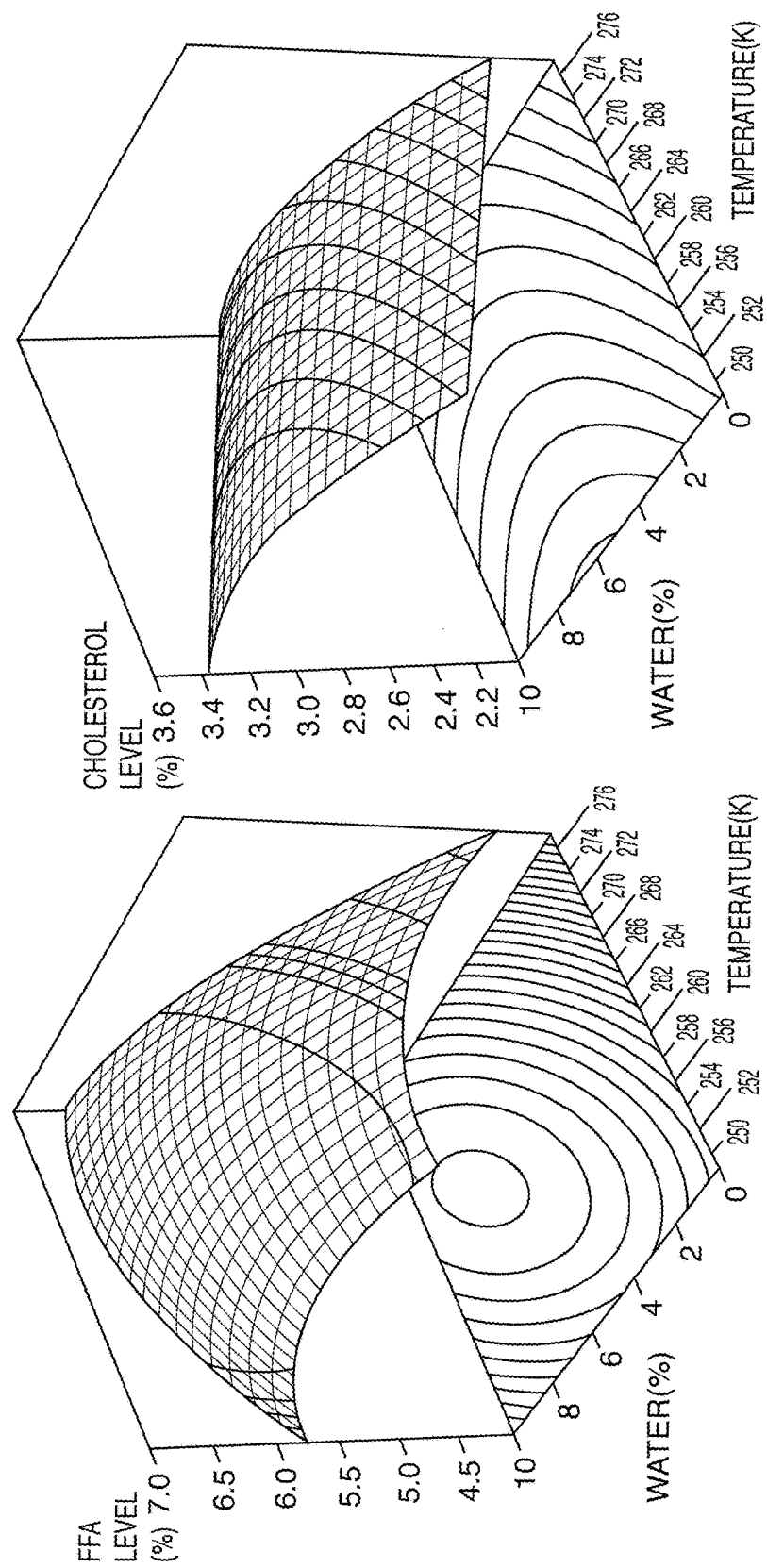

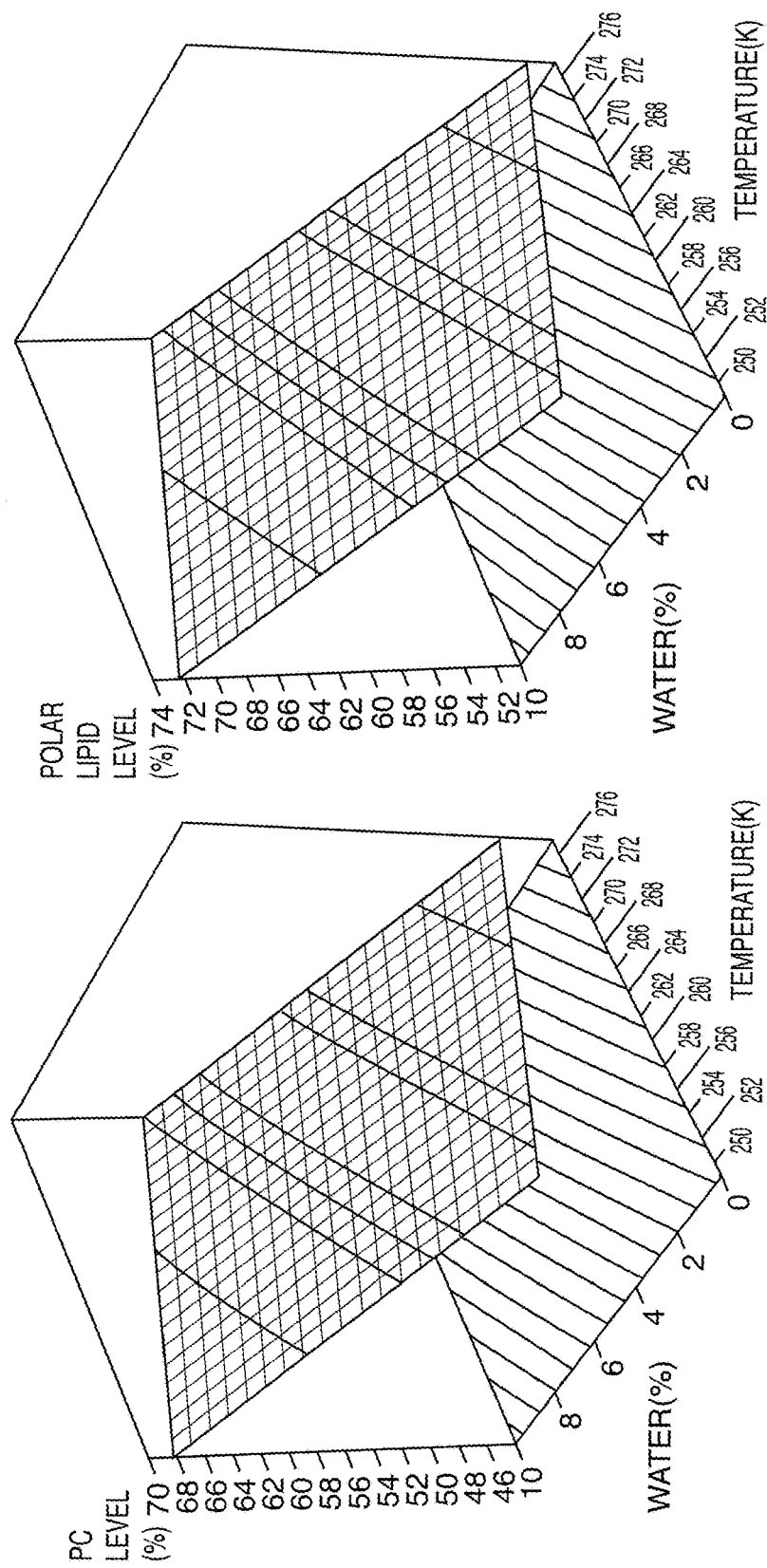

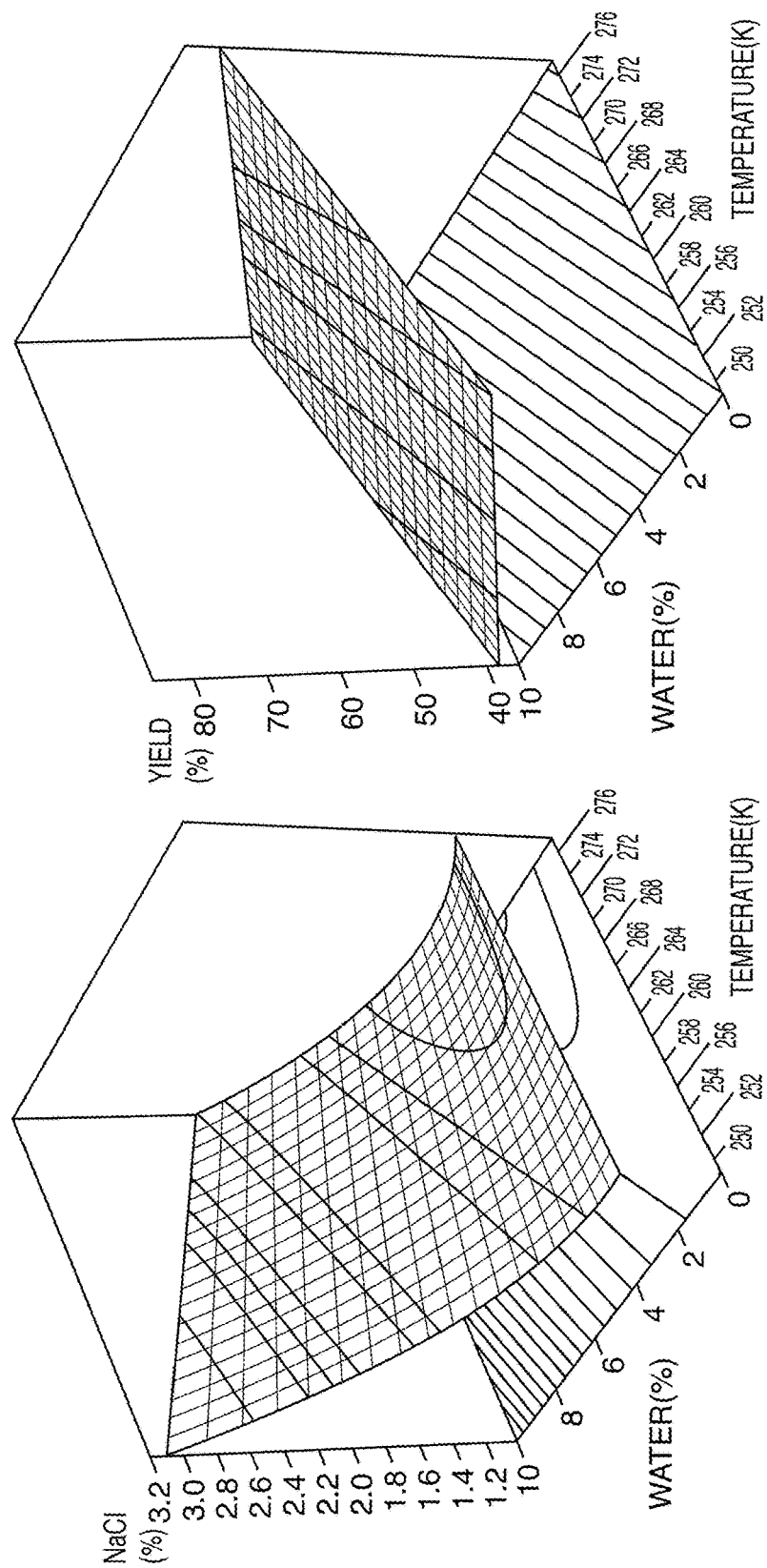

| Fatty Acid | ECL* | %** | g/100g sample (expressed as FFA) | g/100g sample (expressed as TG) |
|---|---|---|---|---|
| 14:0 | 14.01 | 6.9 | 4.8 | 5.1 |
| 15:0 | 14.99 | 0.3 | 0.2 | 0.2 |
| 16:0 | 16.00 | 21.6 | 14.7 | 15.6 |
| 16:1 n-9 | 16.24 | 0.4 | 0.2 | 0.3 |
| 16:1 n-7 | 16.30 | 3.4 | 2.3 | 2.5 |
| 16:1 n-5 | 16.42 | 0.5 | 0.3 | 0.3 |
| i17:0 | 16.51 | 0.3 | 0.2 | 0.2 |
| 16:2 | 16.90 | 0.4 | 0.3 | 0.3 |
| 17:1 | 17.26 | 0.3 | 0.2 | 0.2 |
| i18:0 | 17.50 | 0.4 | 0.3 | 0.3 |
| 16:4 n-1 | 17.83 | 0.4 | 0.2 | 0.3 |
| 18:0 | 18.00 | 1.1 | 0.8 | 0.8 |
| 18:1 n-9 | 18.23 | 8.6 | 5.9 | 6.2 |
| 18:1 n-7 | 18.30 | 6.1 | 4.2 | 4.4 |
| 18:1 n-5 | 18.43 | 0.4 | 0.3 | 0.3 |
| 18:2 n-6 | 18.71 | 1.9 | 1.3 | 1.3 |
| 18:3 n-3 | 19.36 | 1.3 | 0.9 | 1.0 |
| 18:4 n-3 | 19.68 | 3.5 | 2.4 | 2.5 |
| 20:1 n-9 | 20.22 | 0.6 | 0.4 | 0.4 |
| 20:1 n-7 | 20.30 | 0.2 | 0.1 | 0.2 |
| 20:4 n-6 | 21.20 | 0.5 | 0.3 | 0.3 |
| 20:4 n-3 | 21.63 | 0.6 | 0.4 | 0.4 |
| 20:5 n-3 EPA | 21.87 | 21.8 | 14.9 | 15.6 |
| 22:1 n-11 | 22.20 | 0.7 | 0.5 | 0.5 |
| 21:5 n-3 | 22.90 | 0.5 | 0.4 | 0.4 |
| 22:5 n-3 | 23.84 | 0.6 | 0.4 | 0.4 |
| 22:6 n-3 DHA | 24.12 | 13.2 | 9.1 | 9.5 |
| Others | | 2.7 | 1.9 | 2.0 |
| Total n-3 | | 41.5 | 28.5 | 29.8 |
| Total fatty acids | | | 68.7 | 72.1 |

* ECL = equivalent chain length; ** % w/w of total fatty acids

Figure 13

| Phospholipid (PL) | | wt% of total PL | g/100g sample |
|---|---|---|---|
| Phosphatidylcholine | PC | 66.9 | 40.4 |
| Alkyl acyl phosphatidylcholine | AAPC | 7.8 | 4.7 |
| Phosphatidylinositol | PI | 1.3 | 0.8 |
| Phosphatidylserine | PS | 0.5 | 0.3 |
| Lysophosphatidylcholine | LPC | 11.3 | 6.8 |
| Lyso alkyl acyl phosphatidylcholine | LAAPC | 0.8 | 0.5 |
| Phosphatidylethanolamine | PE | 2.7 | 1.6 |
| Alkyl acyl phosphatidylethanolamine | AAPE | 2.6 | 1.5 |
| Cardiolipin + N-acylphosphatidylethanolamine | CL/NAPE | 4.9 | 3.0 |
| Lysophosphatidylethanolamine | LPE | 1.1 | 0.7 |
| Lyso alkyl acyl phosphatidylethanolamine | LAAPE | 0.2 | 0.1 |

Total phospholipid content*     60.5 g/100g sample
    62.4 g/100g solids n.d. = not detected
* Sum of the identified phospholipid classes
 g free choline equivalent per 100g sample Total phospholipid-bound choline     7.2 g/100g sample

Figure 14

FLOWABLE CONCENTRATED PHOSPHOLIPID KRILL OIL COMPOSITION

FIELD OF THE INVENTION

The present invention is related to methods of making crustacean oil compositions. In particular, the crustacean oil compositions are krill oil compositions. In some embodiments, the krill oil compositions are concentrated in phospholipids. These concentrated phospholipid krill oil compositions have a sufficient flowability to permit successful encapsulation at phospholipid concentrations that is currently unattainable in the art. Such phospholipid krill oil compositions are capable of encapsulation even though they may have a phospholipid concentration ranging between approximately 60%-99% and a viscosity ranging between 100,000-3,000,000 cP. Such concentrated phospholipid krill oil compositions may be created using a small molecule organic solvent/water extraction mixture and/or a sub-critical or super-critical fluid extraction at low temperatures followed by a drying process to remove water and organic solvent (e.g., for example, ethanol).

BACKGROUND

Krill are marine crustaceans (Class Malacostraca, Order Euphausiacea) comprising approximately 86 species, a majority of which are free swimming, and are considered plankton. Krill sometimes form dense swarms that can extend over several square kilometers and represent a biomass of thousands or even millions of tons.

There are currently several active krill fisheries but these are dominated by two; one based in *Antarctica* for *E. superba* and the other based predominantly in Japan (but also Canada) targeting *E. pacifica*. Together these two fisheries (*E. superba* and *E. pacifica*) represent at least 97% of the total krill landed. The low levels of environmental pollutants in the Antarctic krill is a benefit for the utilization of the krill for health products. Currently available krill products for human consumption is mainly based on krill oil in where the protein fraction is removed.

To utilize the whole krill for nutritional supplements or for pharmaceuticals (clinical nutrition) there is a need for compositions and formulations in where most of the nutrients and the bioactive components from krill are kept intact and where both lipid soluble and lipid insoluble micronutrients which are required can be in mixed in a feasible way.

While the overall beneficial effects of krill compositions (e.g., for example, krill oil) have been suggested, compositions are unavailable that provide an effective therapeutic treatment without repeated daily doses. Due to this, there is a great need for effective nutritional supplements that contain sufficient concentrations of therapeutic krill oil components such that a only a single daily dose is required.

SUMMARY OF THE INVENTION

The present invention is related to methods of making crustacean oil compositions. In particular, the crustacean oil compositions are krill oil compositions. In some embodiments, the krill oil compositions are concentrated in phospholipids. These concentrated phospholipid krill oil compositions have a sufficient flowability to permit successful encapsulation at phospholipid concentrations that is currently unattainable in the art. Such phospholipid krill oil compositions capable of encapsulation even though they may have a phospholipid concentration ranging between approximately 60%-99% and a viscosity ranging between 100,000-3,000,000 cP. Such concentrated phospholipid krill oil compositions may be created using a small molecule organic solvent/water extraction mixture and/or a sub-critical or super-critical fluid extraction at low temperatures followed by a drying process to remove water and organic solvent (e.g., for example, ethanol).

In one embodiment, the present invention contemplates a krill oil comprising a phospholipid content ranging between approximately 60%-99% (w/w), a water content ranging between 1-4% (w/w) and an organic solvent content of less than 1%. In one embodiment, the organic solvent is ethanol. In one embodiment, the krill oil comprises a viscosity ranging between approximately 100,000-3,000,000 cP. In one embodiment, the krill oil is a gently dried krill oil. In one embodiment, the gently dried krill oil is a lyophilized krill oil. In one embodiment, the krill oil is encapsulated. In one embodiment the krill oil is a semi-solid at a temperature of at least 40° C. In one embodiment, the krill oil further comprises a viscosity modifier. In one embodiment, the krill oil further comprises a thixotropic carrier. In one embodiment, the phospholipid content comprises phosphatidylcholine in a range of approximately 35-55% (w/w), alkyl acyl phosphatidylcholine in a range of approximately 3.0-6.0% (w/w), phosphatidylinositol in a range of approximately 0.5-0.9% (w/w), phosphatidylserine (PS) in a range of approximately 0.3-0.6%, lysophosphatidylcholine in a range of approximately 1.5-4.0%, lyso alkyl acyl phosphatidylcholine in a range of approximately 1.0-0.25%, phosphatidylethanolamine in a range of approximately 2.0-4.0%, alkyl acyl phosphatidylethanolamine in a range of approximately 0.25-1.25%, cardiolipin+N-acylphosphatidylethanolamine in a range of approximately 0.5-2.5%, lysophosphatidylethanolamine in a range of approximately 0.2-0.6%, and lyso alkyl acyl phosphatidylethanolamine of <0.1%. In one embodiment, the krill oil is encapsulated with a capsule that includes but is not limited to a soft gel capsule and a hard gelatin capsule.

In one embodiment, the present invention contemplates a capsule comprising a krill oil having a phospholipid content ranging between approximately 60%-99% (w/w), a water content ranging between 1-4% (w/w) and an organic solvent content of less than 1%. In one embodiment, the organic solvent is ethanol. In one embodiment, the krill oil comprises a viscosity ranging between approximately 100,000-3,000,000 cP. In one embodiment, the krill oil is a gently dried krill oil. In one embodiment, the gently dried krill oil is a lyophilized krill oil. In one embodiment, the krill oil is encapsulated. In one embodiment, the krill oil is a semi-solid at a temperature of at least 40° C. In one embodiment, the capsule further comprises a viscosity modifier. In one embodiment, the capsule further comprises a thixotropic carrier. In one embodiment, the phospholipid content comprises phosphatidylcholine in a range of approximately 35-55% (w/w), alkyl acyl phosphatidylcholine in a range of approximately 3.0-6.0% (w/w), phosphatidylinositol in a range of approximately 0.5-0.9% (w/w), phosphatidylserine (PS) in a range of approximately 0.3-0.6%, lysophosphatidylcholine in a range of approximately 1.5-4.0%, lyso alkyl acyl phosphatidylcholine in a range of approximately 1.0-0.25%, phosphatidylethanolamine in a range of approximately 2.0-4.0%, alkyl acyl phosphatidylethanolamine in a range of approximately 0.25-1.25%, cardiolipin+N-acyl-phosphatidylethanolamine in a range of approximately 0.5-2.5%, lysophosphatidylethanolamine in a range of approximately 0.2-0.6%, and lyso alkyl acyl phosphatidylethanolamine of <0.1%.

In one embodiment, the present invention contemplates a method, comprising: a) providing; i) a krill oil; ii) a mixture comprising a small molecule organic solvent and water; iii) a temperature controlled reaction vessel; b) mixing said krill oil and said mixture in said reaction vessel; d) incubating said mixture and said krill oil in said reaction vessel such that a phase separation comprising a triglyceride-rich insoluble fraction and a concentrated polar lipid krill oil is created; e) isolating said concentrated polar lipid krill oil from said triglyceride-rich insoluble fraction; and f) gently drying said concentrated polar lipid krill oil to evaporate said small molecule organic solvent and said water from said concentrated polar lipid krill oil to create a concentrated polar lipid semi-solid krill oil comprising a water content ranging between approximately 1-4% (w/w) and an organic solvent content of less than 1%. In one embodiment, the organic solvent is ethanol. In one embodiment, the concentrated polar lipid krill oil comprises a viscosity ranging between approximately 100,000-3,000,000 cP. In one embodiment, the concentrated polar lipid krill oil is encapsulated. In one embodiment, the concentrated polar lipid krill oil is a semi-solid at a temperature of at least 40° C. In one embodiment, said concentrated polar lipid krill oil comprises between approximately 60-99% polar lipids. In one embodiment, the concentrated polar lipid krill oil comprises approximately 63% polar lipids. In one embodiment, the concentrated polar lipid krill oil comprises approximately 72% polar lipids. In one embodiment, the small molecule organic solvent is selected from the group consisting of ethanol, subcritical carbon dioxide, supercritical carbon dioxide and acetone. In one embodiment, the temperature ranges between approximately 0° C. to −25° C. In one embodiment, the reaction mixture comprises a ratio of the small molecule organic solvent and the water ranging between 100:0 to 1:99. In one embodiment, the ratio of the small molecule organic solvent and the water ranges between 100:0 to 90:10. In one embodiment, the ratio of the small molecule organic solvent and the water is 94:6. In one embodiment, the polar lipids comprise a combination of phosphatidylethanolamine, phosphatidylcholine and lyso-phosphatidylcholine.

In one embodiment, the present invention contemplates a method comprising: a) providing; i) a krill oil composition comprising phospholipids ranging between 60%-99% (w/w), water and an organic solvent; ii) a means for gentle drying; and iii) an empty capsule; b) gently drying the krill oil composition under conditions such that a gently dried krill oil product comprising a water content between approximately 1-4% (w/w) and an organic solvent content less than 1% is created; and c) filling the empty capsule with the gently dried krill oil at a temperature of at least 40° C. In one embodiment, the means for gentle drying is a lyophilizer In one embodiment, the means for gentle drying is an oven. In one embodiment, the means for gentle drying is a nitrogen stream. In one embodiment, the gently dried krill oil is a semi-solid at a temperature of at least 40° C. In one embodiment, the filling is performed with a capsule filling machine. In one embodiment, the krill oil further comprises a viscosity modifier. In one embodiment, the krill oil further comprises a thixotropic carrier. In one embodiment, the phospholipid content comprises phosphatidylcholine in a range of approximately 35-55% (w/w), alkyl acyl phosphatidylcholine in a range of approximately 3.0-6.0% (w/w), phosphatidylinositol in a range of approximately 0.5-0.9% (w/w), phosphatidylserine (PS) in a range of approximately 0.3-0.6%, lysophosphatidylcholine in a range of approximately 1.5-4.0%, lyso alkyl acyl phosphatidylcholine in a range of approximately 1.0-0.25%, phosphatidylethanolamine in a range of approximately 2.0-4.0%, alkyl acyl phosphatidylethanolamine in a range of approximately 0.25-1.25%, cardiolipin+N-acylphosphatidylethanolamine in a range of approximately 0.5-2.5%, lysophosphatidylethanolamine in a range of approximately 0.2-0.6%, and lyso alkyl acyl phosphatidylethanolarnine of <0.1%. In one embodiment, the krill oil is a collodial krill oil. In one embodiment, the krill oil is a homogeneous krill oil.

In one embodiment, the present invention contemplates a method, comprising: a) providing: i) a patient exhibiting at least one symptom of a medical disorder; ii) a krill oil comprising a phospholipid concentration ranging between approximately 60%-99%, a water content ranging between approximately 1-4% and an organic solvent content of less than 1%; b) administering said krill oil to said patient under conditions such that said at least one symptom is reduced. In one embodiment, the krill oil comprises a viscosity ranging between approximately 100,000-3,000,000 cP. In one embodiment, the krill oil is a semi-solid at a temperature of at least 40° C. In one embodiment the medical disorder comprises an age-related medical disorder. In one embodiment, the age-related medical disorder includes, but is not limited to, a lack of homeostatic control, macular degeneration, diabetes, or inflammation. In one embodiment, the medical disorder comprises malnutrition. In one embodiment, the medical disorder comprises an ocular disorder. In one embodiment, the medical disorder comprises a cardiovascular disorder. In one embodiment, the medical disorder comprises a skeletal medical disorder. In one embodiment, the medical disorder comprises a central nervous system disorder. In one embodiment, the central nervous system disorder comprises a mental disorder. In one embodiment, the mental disorder includes, but is not limited to infancy, childhood or adolescence disorders, cognitive disorders, substance-related disorders, psychotic disorders including but not limited to schizophrenia, mood disorders including but not limited to depression, anxiety disorders, somatoform disorders, factitious disorder, dissociative disorders, sexual disorders, eating disorders, sleep disorders, impulse-control disorders, adjustment disorders or personality disorders. In one embodiment, the medical disorder comprises a muscular disorder. In one embodiment the medical disorder comprises cachexia. In one embodiment, the medical disorder comprises digestive tract medical disorder. In one embodiment, the medical disorder comprises a dyslipidemic medical disorder. In one embodiment, the medical disorder comprises a hair disorder. In one embodiment, the medical disorder comprises a nail disorder. In one embodiment, the medical disorder comprises a skin disorder. In one embodiment, the krill oil is encapsulated. In one embodiment, the krill oil is encapsulated in a hard gelatin capsule. In one embodiment, the krill oil is encapsulatedin a soft gel capsule. In one embodiment, the krill oil further comprises an additional ingredient including, but not limited to, minerals, lipid soluble vitamins, lipid insoluble vitamins, bioactive health ingredients and/or omega-3 oils. In one embodiment, the administered composition ranges between 0.005-0.50 grams per day per kilogram of said patient's body weight. In one embodiment, the encapsulated krill oil comprises approximately 600 mg phospholipids.

Definitions

As used herein and in the appended claims, the singular forms "a," "an," and "the" include plural reference unless the context clearly dictates otherwise, e.g., reference to "a method" includes a plurality of such methods.

The words "comprise", "comprises", and "comprising" are to be interpreted inclusively rather than exclusively.

The term "optionally" means here the same as "possibly". For example, compositions disclosed herein as "optionally comprises excipients", means that the composition may or may not comprise excipients, in other words the composition possibly comprises excipients.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "animal" as used herein, means species including but not limited to mammals, fish, crustaceans, amphibians, reptiles etc. In particular, a "companion animal" refers to any non-human animal kept by a human as a pet or any animal of a variety of species that have been widely domesticated as pets, such as dogs (*Canis familiaris*), and cats (*Felis domesticus*), whether or not the animal is kept solely or partly for companionship. Companion animals also include working animals including but not limited to horses, cows, pigs, goats, sheep, dogs (i.e., for example, livestock herding) and/or cats (i.e., for example, rodent control).

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds that exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "krill oil" as used herein, refers here to any mixture of extracted lipids derived from any portion of a krill organism. The term is not limited to any particular method of making krill oil, but any method known in the art is contemplated. Conventionally made krill oil is generally considered to be a liquid having a viscosity that is proportional to phospholipid concentration, where viscosity increases a phospholipid concentration increases.

The term "semi-solid" as used herein, refers to the physical nature of a substance or material that has characteristics of both solids and liquids. While similar to a solid in some respects, semisolids can support their own weight and hold their shapes, and retains an ability to flow under pressure. Semisolids are also known as amorphous solids because at the microscopic scale they have a disordered structure unlike the more common crystalline solids. Those in the art would understand that the words quasisolid, semisolid, and semiliquid may be used interchangeably.

The term "gently dried" as used herein, refers to an evaporation process that selectively removes low molecular weight molecules (e.g., water and/or organic solvents such as ethanol). For example, heating in a oven, evaporation under a nitrogen stream or lyophilization are examples of gentle drying techniques.

The term "gently dried krill oil" as used herein, refers to any mixture of extracted lipids derived from a krill organism that has been processed into a product having substantially reduced water content and/or organic solvent content (e.g., for example, ethanol). For example, a gently dried krill oil may be expected to have a water content of between 1-4% (w/w) and/or an organic solvent content of less than 1%. A gentle drying process produces an oil that is a semi-solid and has flowable properties at temperatures above forty (40) degrees Centigrade (40° C.).

The term "small molecule organic solvent" as used herein refers to a non-cyclic aliphatic molecule comprising five (5) carbon atoms or less. Preferably, such solvents are short chain alcohols (e.g., ethanol) or oxidative products thereof (e.g., acetone).

The term "temperature controlled reaction vessel" as used herein refers to any container of any size or shape configured to maintain a desired stable temperature. Preferably, the temperature is maintained between +45° C. to −50° C.

The term "viscosity" as used herein, refers to a measured parameter (e.g., expressed as poise) describing the fluidic nature of a material. For example, a material having high viscosity may have a glutinous nature or consistency and is described as being, for example, sticky, thick and/or adhesive. On the other hand, a material having low viscosity may have a free flowing fluid nature that is more comparable water or other aqueous substance.

The term "poise" as used herein, refers to a centimeter-gram-second unit of viscosity, equal to the viscosity of a fluid in which a stress of one dyne per square centimeter is required to maintain a difference of velocity of one centimeter per second between two parallel planes in the fluid that lie in the direction of flow and are separated by a distance of one centimeter. Generally, the units of expression are reported as centipoise.

The term "medical disorders", as used herein, refers to any biological condition diagnosed by medically trained personnel to require treatment. For example, medical disorders may include, but are not limited to, hair disorders, nail disorders, skin disorders, skeletomuscular disorders, multiple sclerosis, or sexual disorders.

The term "delusion", as used herein, refers to any mental condition that results in the perception of an altered reality. Specifically, delusion is contemplated to be, but not limited to, "delusions of grandeur", psychoses or hallucinations.

The term "schizophrenia", as used herein, refers to any idiopathic psychosis characterized by chronically disordered thinking and emotional withdrawal often associated with paranoid delusions and auditory hallucinations.

The term "mood disorder", as used herein, refers to any mental condition that results in behavior patterns representing alterations in mood. Specifically, mood disorders are contemplated to be, but not limited to, unipolar depression or bipolar depression.

The term "personality disorder", as used herein, refers to any condition, that may or may not respond to medical intervention, that include perversion and chronic dysfunction appearing in multiple forms during a patient's life. In one embodiment, characteristic symptoms include, but are not limited to, avoidance, paranoia, withdrawal and dependency. More generally, another embodiment reflects a pattern of behavior such as, but not limited to, chemical dependency, deviant eating patterns, hypochondriasis or antisocial behavior.

The term "deviant eating patterns", as used herein, refer to any condition wherein a compulsive behavior pattern results in a significant increase or decrease in food consumption. Specifically, the present invention contemplates, but is not limited to, conditions such as bulimia and anorexia nervosa.

The term "depression", as used herein, refers to any nervous system disorder and/or mental condition characterized by, but not limited to, the following symptoms: withdrawal, insomnia, hypersomnia, loss of appetite, altered daily rhythms of mood, activity, temperature and neuroendocrine function. For example, dsythymia, seasonal affective disorder and the like.

The term "neuroses", as used herein, refers to any mild psychiatric disorder wherein the ability to comprehend is retained but suffering and disability are very severe. Other characteristics of neuroses include, but are not limited to, mood changes (i.e., for example, anxiety, panic, dysphoria) or limited abnormalities of thought (i.e., for example, obsessions, irrational fears) or of behavior (rituals or compulsions, pseudoneurological or hysterical conversion signs).

The term "psychoses", as used herein, refers to any severe psychiatric disorder wherein there is a marked impairment of behavior, a serious inability to think coherently, or to comprehend reality. Psychoses may include organic conditions associated with a definable toxic, metabolic, or neuropathologic change characterized by confusion, disorientation, memory disturbances and behavioral or intrapulmonary disorganization.

The term "anxiety state", as used herein, refers to any human emotion, closely allied with appropriate fear, often serving psychobiologically adaptive purposes that is a cardinal symptom of many psychiatric disorders. Specifically, anxiety is commonly associated with, but not limited to, neurotic depression, panic disorder, phobias, obsessive-compulsive disorders and other related personality disorders.

The term "improved performance", as used herein, refers to any biological condition, where controlled medical testing measures results that medically trained personnel would considered above the expected norm. For example, improved performance may be measured for physical or mental tests.

The term "effective amount" refers to any amount of a supplement that improves the palatability of the food or feed.

The term "ingredient" or "supplement" refers to any composition can be formulated to a suitable form, such as a tablet, a granule, a pellet or powder. The composition may be formulated also to a pet treat or a hard gelatin capsule (sprinkle capsule) can be filled with the composition.

As used herein, the term "omega-3 fatty acid" refers to fatty acids which have the final double bond between the third and the fourth carbon atom counting from the methyl end of the carbon chain. Omega-3 fatty acids mainly concerned in this disclosure are the long chain polyunsaturated fatty acids eicosapentaenoic acid (EPA) and docospentaenoic acid (DHA) as well as the minor omega-3 fatty acids including eicosatetraenoic acid (ETA) and docosapentaenoic acid (DPA).

The term "excipients", as used herein, refer to any substance needed to formulate the composition to the desired form. For example, suitable excipients include but are not limited to, diluents or fillers, binders or granulating agents or adhesives, disintegrants, lubricants, antiadherants, glidants, wetting agents, dissolution retardants or enhancers, adsorbents, buffers, chelating agents, preservatives, colours, flavours and sweeteners. Typical excipients are for example starch, pregelatinized starch, maltodextrin, monohydrous dextrose, alginic acid, sorbitol and mannitol. In general, the excipient should be selected from non-toxic excipients (IIG, Inactive Ingredient Guide, or GRAS, Generally Regarded as safe, Handbook of Pharmaceutical Excipients). Typical excipients in particular for tableting are for example magnesium stearate, stearic acid, talc, silic, cellulose, microcrystalline cellulose, methyl cellulose, polyvinylpyrrolidone and—commercial products, such as Aerosil®, Kollidon® and Explotab®. Excipients can be added into the direct powder compression formula.

The term "clinical nutrition", as used herein, refers to the study, treatment and/or prevention of nutritionally-related medical disorders, including but not limited to malnutrition.

The term "fluoride" as used herein interchangeably and refer to any compound containing an organofluoride and/or an inorganic fluoride.

The term "low fluoride" as used herein may refer to the product of any method and/or process that reduced the fluoride from the original material by approximately one third (i.e., for example, from 1500 ppm to 500 ppm). For example, "a low fluoride crustacean phospholipid-protein complex" comprises approximately one third of the fluoride than "a hydrolyzed and disintegrated crustacean material".

The term "low fluoride oil" as used herein refers to a lipid-rich composition created by the extraction of a phospholipid-peptide complex composition subfraction using a selective extraction process, such as with a supercritical carbon dioxide fluid. Such a process removes approximately ten-fold of the fluoride from the raw hydrolyzed and disintegrated crustacean material.

The term "phospholipid composition" as used herein refers to a low fluoride composition comprising a high percentage of polar lipids (e.g., approximately 75%) created by the extraction of a de-oiled phospholipid-peptide complex using a co-solvent, such as ethanol.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "pharmaceutically acceptable" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to amino acid sequences, that are removed from their natural environment, isolated or separated, and are at least 60% free, preferably 75% free, and more preferably 90% free from other components with which they are naturally associated. An "isolated peptide or protein" is therefore a substantially purified peptide or protein.

BRIEF DESCRIPTION OF THE FIGURES

FIG. 9A-9B presents exemplary data showing a Principal Component Analysis of acetone versus ethanol fractionation of krill oil.

FIG. 9A: PCA correlation loading plot based on process optimization design and response variables given in Tables 9, 11 and 12. Figures represent correlation coefficients r1 and r2 between the input X- and Y-variables and the first 2 PCs t1 (abscissa) and t2 (ordinate). The two ellipses represents 50% and 100% explained variances.

FIG. 9B: PCA score plot showing similarities and differences in response based on the applied combinations of process conditions. Markers represents (ENo)—temperature (° C.)—water content in the ethanol phase (%). Abbreviations explained in Table 7.

FIG. 10A-10E presents exemplary data showing a neutral lipid response surface and contour plots based on models described in Table 9.

FIG. 11A-11F presents exemplary data showing a polar lipid, sodium chloride and total yield response surface and contour plots based on models described in Table 9.

FIG. 13 presents exemplary data showing a representative fatty acid analysis of krill oil extracted with a solvent comprising subcritical carbon dioxide.

FIG. 14 presents exemplary data showing a representative phospholipid analysis of krill oil extracted with a solvent comprising subcritical carbon dioxide.

DETAILED DESCRIPTION OF THE INVENTION

Figure 1:
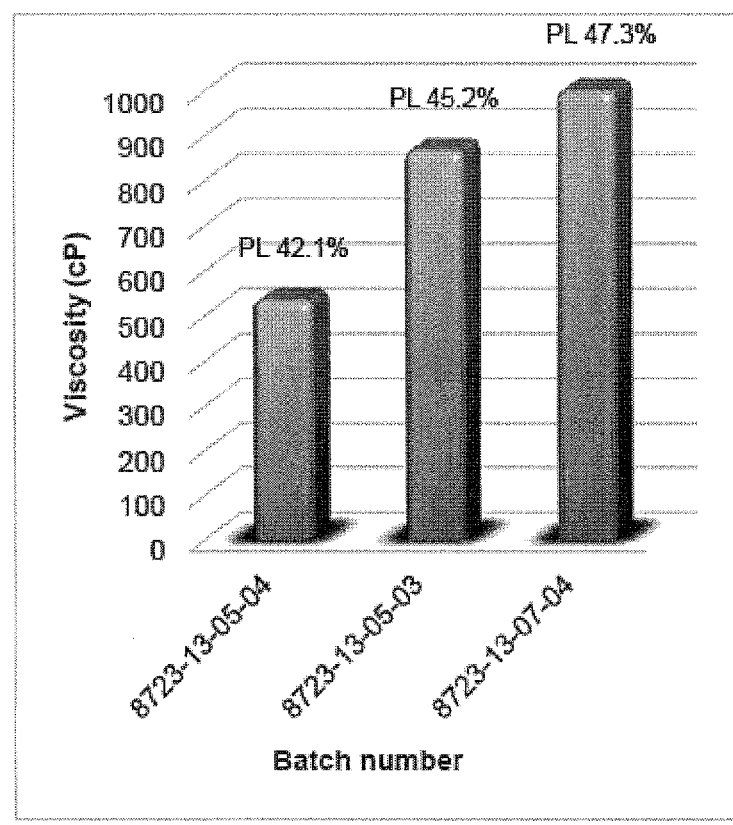
FIG. 1 presents exemplary data of phospholipid (PL) content's effect on viscosity of concentrated krill oil compositions. Viscosity (cP) was measured at 35° C. in 3 batches of krill oil. Batch 8723-13-06-04, 8723-05-03 and 8723-13-07-04 contained 42.1%, 45.2% and 47.3% phospholipids (PL), respectively.

The present invention is related to methods of making crustacean oil compositions. In particular, the crustacean oil compositions are krill oil compositions. In some embodiments, the krill oil compositions are concentrated in phospholipids. These concentrated phospholipid krill oil compositions have a sufficient flowability to permit successful encapsulation at phospholipid concentrations that is currently unattainable in the art. Such phospholipid krill oil compositions are capable of encapsulation event though they may have a phospholipid concentration ranging between approximately 60%-99% and a viscosity ranging between 100,000-3,000,000 cP. Such concentrated phospholipid krill oil compositions may be created using a small molecule organic solvent/water extraction mixture and/or sub-critical or super-critical fluid extraction at low temperatures followed by a drying process to remove water and organic solvent (e.g., for example, ethanol).

In one embodiment, the present invention contemplates a crustacean oil composition (e.g., for example, a krill oil composition) comprising a phospholipid content ranging between approximately 60%-99% (w/w), a water content ranging between approximately 1-4% (w/w) and an organic solvent content of less than 1%. In one embodiment, the viscosity of the crustacean oil composition ranges between approximately 100,000-3,000,000 centipoise, preferably between approximately 100,000-150,000 cP, preferably between approximately 140,000-1,700,000 cP, preferably between approximately 2,000,000-3,000,000 cP or preferably between approximately 2,500,000-275,000,000 cP. In other embodiments, the present invention contemplates concentrated krill oil compositions comprising at least 60% (w/w) phospholipids including, but not limited to, phosphatidylcholine in a range of approximately 35-55% (w/w), alkyl acyl phosphatidylcholine in a range of approximately 3.0-6.0% (w/w), phosphatidylinositol in a range of approximately 0.5-0.9% (w/w), phosphatidylserine (PS) in a range of approximately 0.3-0.6%, lysophosphatidylcholine in a range of approximately 1.5-4.0%, lyso alkyl acyl phosphatidylcholine in a range of approximately 1.0-0.25%, phosphatidylethanolamine in a range of approximately 2.0-4.0%, alkyl acyl phosphatidylethanolamine in a range of approximately 0.25-1.25%, cardiolipin+N-acylphosphatidylethanolamine in a range of approximately 0.5-2.5%, lysophosphatidylethanolamine in a range of approximately 0.2-0.6%, and lyso alkyl acyl phosphatidylethanolamine of <0.1%.

It has previously been reported that some conventional krill oil extraction methods generally result in a phospholipid concentration ranging between approximately 39-52%. One particular method is directed towards producing crustacean oils that are low in fluoride and/or trimethylamine (TMA)/trimethylamine oxide (TMAO). Bruheim et al., WO 2013/102792.

Others have reported krill oil compositions that are suggested to be concentrated therapeutic phospholipid concentrations where the phospholipids are claimed in the range of approximately 50%-99%. One report appears to suggest that concentrated phospholipid compositions are not resultant from natural extraction methods, but require addition of previously purified phospholipids to the naturally extracted krill oil. Sampalis et al., U.S. Pat. No. 8,586,567 (herein incorporated by reference).

I. Conventional Phospholipid Extraction Methods

Separation of neutral and polar lipids in crude lipid extracts have been obtained by use of acetone fractionation or deoiling. Ziegelitz, "Lecithin processing possibilities" *INFORM* 6:1224-1230 (1995); and Joshi et al., "Modification of lecithin by physical, chemical and enzymatic methods" *Eur. J. Lipid. Sci. Technol.* 108:363-373. (2006). These processes are used on an industrial scale to de-oil crude vegetable lecithin from degumming of vegetable oils after hexane extraction. The principle is based on the insolubility of phospholipids and glycolipids in acetone. Cool acetone at 8-10° C. is intensively mixed in excess with the crude lipid extract and the separated lecithin glycolipid mixture is decanted. The acetone is removed and the product formulated. Crude vegetable lecithin is described to give a phospholipid product after acetone fractionation that can be sieved into granules and powder. A less focused drawback is the possible formation of adducts between acetone and the aminophospholipids phosphatidylethanolamine (PE) and -serine (PS). Kuksis et al., "Covalent binding of acetone to aminophospholipids in vitro and in vivo" In: Baynes, J. W.; Monnier, V. M.; Ames, J. M., and Thorpe, S. R., Eds., Maillard Reaction: Chemistry at the Interface of Nutrition, Aging, and Disease. Annals of the New York Academy of Sciences, pp. 417-439 (2005).

Figure 8:
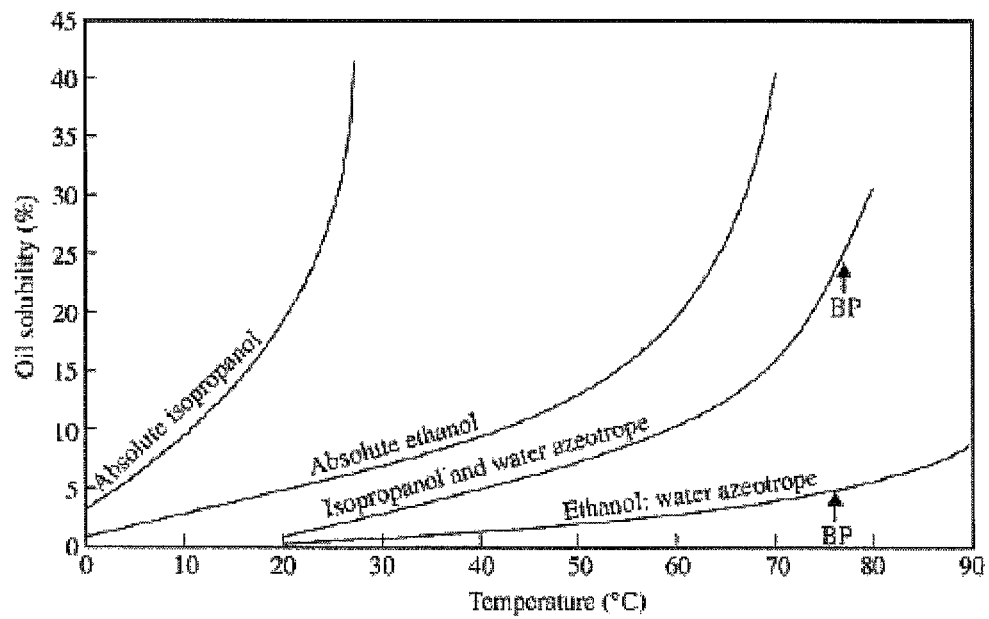
FIG. 8 presents exemplary data showing the relationships between triacylglycerol (TAG) solubility in alcohols with temperature and water content. Shown is the solubility of cottonseed oil in absolute ethanol and isopropanol and their azeotropes, BP=boiling point. Lusas et al., "Final report: IPA as an extraction solvent" INFORM 8(3):290-306 (1997).

The use of alcohols has been extensively studied by the vegetable oil industry to find a safer and environmental friendly alternative to hexane. Lusas et al., "Final report: IPA as an extraction solvent" *INFORM* 8(3):290-306 (1997). The biggest disadvantages of alcohols as compared to hexane are believed to be higher energy consumption for vapour recovery and a lower solubility of vegetable oil of about half of is practical achievable in counter current extraction based on hexane (33% oil). However, this property can also be used to achieve a fractionation of the triacylglycerides (TAG) in the oil. For example, it has been reported that TAG solubility in alcohols is reduced by both temperature and water content. See, FIG. 8.

Crude vegetable lecithins obtained by the conventional methods described above generally contain a mixture of PC, PE and PI. It has been reported that the PC and PI fractions have different solubility when extracted using the lower aliphatic chain alcohols (e.g., ethanol and/or methanol) or when using ethanol/water mixtures at varying temperatures where the PC fraction appears more soluble. Joshi et al., "Modification of lecithin by physical, chemical and enzymatic methods" *Eur. J. Lipid. Sci. Technol.* 108:363-373. (2006). These processes have also obtained lecithin with a PC content of 35-50%. For example, fractionation of sunflower lecithin by ethanol fractionation has been reported where the main objective was to separate PC, PI and PE by use of absolute ethanol with an ethanol:lecithin ratio of between 2:1 and 3:1 within a temperature range of between 35-65° C. A PC-enriched ethanol phase was obtained having up to approximately 62.5% phospholipids. Cabezas et al., "Sunflower Lecithin: Application of a Fractionation Process With Absolute Ethanol" *J. Am. Oil Chem. Soc.* 86:189-196 (2009).

The use of fractional separation to concentrate PUFA and phospholipids in an isopropanol (IPA) extracted marine lipids has also been reported. Sola et al., "Process for enrichment of fat with regard to polyunsaturated fatty acids and phospholipids, and application of such enriched fat" EP 0 519 916 B1 (1993). Following partial IPA evaporation, insoluble lipids were separated and collected that contained concentrated PUFA levels. A combination of low temperature (4° C.) ethanol fractionation and β-cyclodextrine complexation was oberved to extract triacylglycerols and cholesterol from egg yolk. Su et al. "Study on a Novel Process for the Separation of Phospholipids, Triacylglycerol and Cholesterol From Egg Yolk" *Journal of Food Science and Technology-Mysore* 52:4586-4592 (2015). In this study, 75.8% of the TAG was precipitated after 10 hours at 4° C. After β-cyclodextrine cholesterol complexation, the residual phospholipids in the ethanol phase was obtained after solvent removal. Alternatively, ethanol extracted lipids from dried egg yolk were cold temperature crystallized to remove TAG. A PL-level of 77% phospholipids was obtained based on crystallization at 0° C. and 4% water content in the ethanol phase. Nielsen et al., "In Situ Solid Phase Extraction of Lipids From Spray-Dried Egg Yolk by Ethanol With Subsequent Removal of Triacylglycerols by Cold Temperature Crystallization" *Food Science and Technology* 37:613-618 (2004).

Supercritical (SC) carbon dioxide has been used in several studies to concentrate phospholipids. The neutral lipid components are soluble in the SC carbon dioxide leaving the polar phospholipids behind. SC carbon dioxide mixed with ethanol as a co-solvent has also been used for fractionation of phospholipids, oil and cholesterol from egg-yolk. Sahena et al., "Application of Supercritical $CO_2$ in Lipid Extraction—a Review" *Journal of Food Engineering* 95:240-253 (2009).

Membrane filtration technology has been extensively studied as a more environmental friendly and cost-effective alternative to conventional organic solvent oil extraction and refining methods related to degumming, dewaxing, deacidification, pigment removal, concentration of minor components and/or separation of emulsions, exemplified by several reports of soy and rice bran lecithin deoiling using ultrafiltration. Coutinho et al., "State of Art of the Application of Membrane Technology to Vegetable Oils: a Review. Food Research International" 42:536-550 (2009); Manjula et al., "Laboratory Studies on Membrane Deoiling of Lecithin" *J. Am. Oil Chem. Soc.* 85:573-580 (2008); and Liu et al., "Preparation of Deoiled Soy Lecithin by Ultrafiltration" *Journal of the American Oil Chemists Society* 88:1807-1812 (2011). Alternatively, reverse micelles have been prepared in hexane by the addition of lecithin and water. Filtration was then run in a diafiltration mode and the obtained final PL concentration was in the range 90-96% measured as acetone insoluble matter. Both nonporous polymeric composite hydrophobic membrane and ceramic membrane (5 nm) have successfully been used. Generally, a ceramic membrane will be of advantage since it is inert against solvents and avoids the possible swelling of synthetic membranes with change in the physicochemical properties. "Production of purified yolk lecithin" JPS62263192(A) (Priority date 1987-11-16); "Production of egg yolk lecithin" JP2001072693(A) (Priority date 1999-09-03); "Method of preparing low impurity, clear and transparent food grade lecithin and product" CN1948317 (A) (Priority date 2005-10-13); and "A producing method for food-level concentrated soybean phospholipid" CN101006824 (A) (Priority date 2007-01-22).

II. Relationships Between Phospholipid Concentration and Krill Oil Viscosity

In general, a higher level of phospholipids makes a krill oil on average, thicker and more viscous than fish oils, for example. If the viscosity gets too high, it becomes problematic to encapsulate the oil resulting in capsules that are leaking and unusable. This results in high losses for the capsule producers. Another problem is when the variation in viscosity is high. While the high variability may be overcome, it is more tedious and time consuming for the capsule producer.

Hence, the present invention provides an improved concentrated phospholipid krill oil comprising a low water content and a low organic solvent content that is a semi-solid composition at a temperature of at least 40° C. that provides efficient, and commercially feasible encapsulation. The data presented herein show that, using the provided methods, a concentrated phospholipid krill oil composition is made having a high viscosity but can efficiently undergo commercial encapsulation with automated capsule filling machines.

A. Effect of Phospholipid Content on Krill Oil Viscosity

Preliminary data from krill oil compositions having approximately 42% phospholipids demonstrated a viscosity of equal to, or less than, 800 cP. Although it is not necessary to understand the mechanism of an invention, it is believed that these moderate phospholipid krill oils have a low viscosity that allow for easy encapsulation with repeatable results and of high quality. However, as the viscosity of the krill oil becomes higher and higher as a result of increases in phospholipid content, the concomitant increase in viscosity prevents efficient capsule filling.

Surprisingly, the data presented herein shows that by reducing both the water content and ethanol content in these concentrated phospholipid krill oils, a semi-solid oil is created having flowable characteristics at a temperature of at least 40° C. These conditions allow efficient use of automated capsule filling machines that is not possible with highly viscous conventional high phospholipid content, high water content and high organic solvent content krill oils, because these compositions are solid even at a temperature of approximately 80° C.

To demonstrate the relationship between krill oil phospholipids and viscosity, krill oils with different phospholipid content were prepared in accordance with Example I. The viscosity was measured in accordance with Example II which contained phospholipids in the amounts of 42.1 g, 45.1 g and 47.3 g per 100 g respectively at the temperature of 35° C. The data demonstrate that viscosity increases in proportion with increased concentration of phospholipids. For example, the viscosity was highest for the krill oil that had the highest phospholipid content around 47.3 g/100 g and lowest for batch 8723-13-07-04 which contained 42.1 g/100 g phospholipids. See, FIG. 1.

B. Low Batch-to-Batch Krill Oil Viscosity Variation

Figure 2:
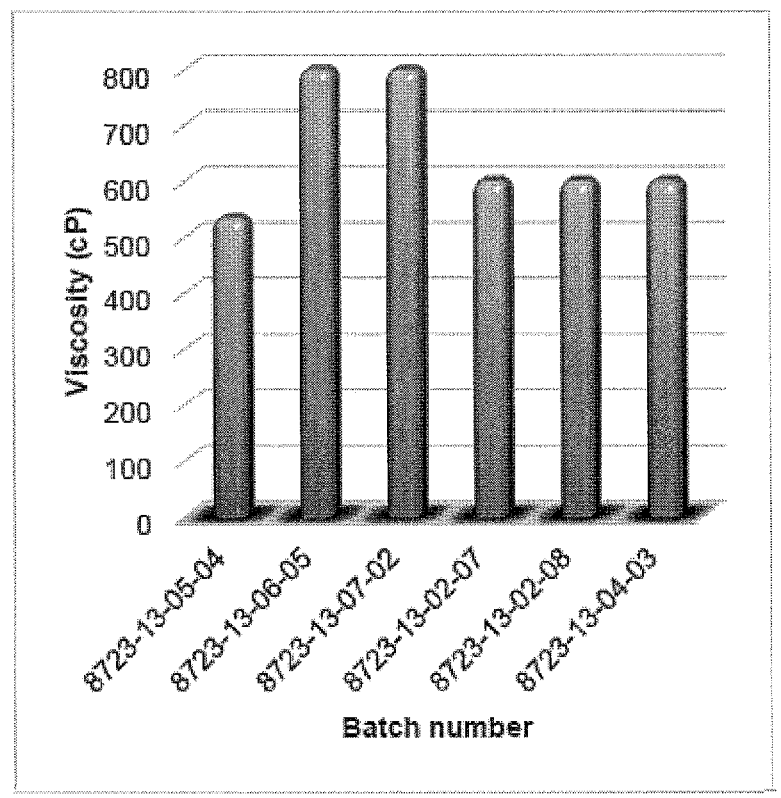
FIG. 2 presents exemplary data of a predictable krill oil viscosity (cP) level having an average PL content of 42.2% (RSD=0.7%) (N=6).

Krill oils with similar phospholipid content were prepared to determine the reliability of producing compositions having a predictable viscosity. For example, viscosity was measured for the batches of krill oil compositions labelled 8723-13-05-04, 8723-13-06-05, 8723-13-07-02, 8723-13-02-07, 8723-13-02-08 and 8723-13-04-03, which contained phospholipids in the amount of 42.1 g, 42.3 g, 41.8 g, 42 g, 42.6 g and 42.5 g per 100 g respectively at the temperature of 35° C. The results demonstrate a repeatable low viscosity with an average of 655 cP with a relative standard deviation (RSD) of 17%. See, FIG. 2.

C. Concentrated Phospholipid Krill Oils (e.g., >60%)

It has been reported that a krill oil having an approximate 52% phospholipid concentration can be successfully encapsulated into soft gels. Even though this report suggested that 65% phospholipid krill oil compositions might be obtainable, there is no enabling data and the reference teaches away from the presently contemplated invention by stating that encapsulation of krill oils having phospholipid concentrations higher than 52% was difficult and considered commercially unsuccessful due to an increased viscosity of the 65% composition. Bruheim et al., Example 5 and Tables 20A-C; WO 2008/117062.

While it has also been suggested that concentrated phospholipid krill oil in excess of 60% can be encapsulated, there is no guidance to one of ordinary skill in the art as how to successfully perform encapsulation of a 60% concentrated phospholipid krill oil compositions that overcome the known problems in the art as discussed herein. Sampalis et al., U.S. Pat. No. 8,586,567 (herein incorporated by reference). The '567 patent reported some viscosity measurements, but only for the 47% phospholipid krill oil composition which was reported to be 1323 centipoise. The reported composition analysis for 53%, 66%, 80% phospholipid krill oil compositions viscosity were not listed as a measured parameter. However, for the 90% phospholipid krill oil composition, viscosity was listed as an intended measured parameter but no data was presented.

Figure 3:
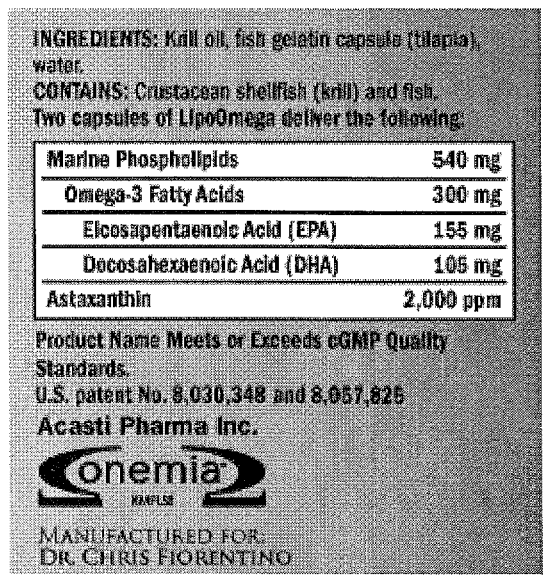
FIG. 3 presents the packaging label showing compositional analysis and patent protection of a commercially available krill oil composition (Omenia, Acasti, Inc.)
Figure 4:
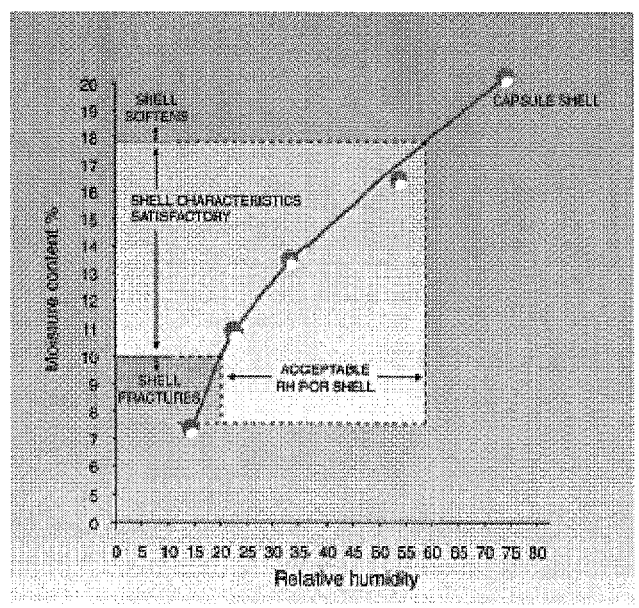
FIG. 4 presents exemplary data showing equilibrium moisture content of empty gelatin capsules shells stored at different relative humidities for 2 weeks at 20° C.

In fact, even though the Sampalis et al. '567 patent is currently assigned to Acasti, Inc. at the time of filing the present application, Acasti Inc. has no commercial krill oil composition with a phospholipid concentration of greater than 50%, much less a commercial product sold as soft gel capsules. Acasti's current commercial krill oil (Omenia®) is supported by Sampalis et al., U.S. Pat. No. 8,030,348 (herein incorporated by reference). See, FIG. 3. The '348 patent discloses a viscosity of approximately 1300 centipoise (cP) for a phospholipid krill extract composition having approximately 40% total phospholipids and teaches only that encapsulation may be performed by conventional means known at the time of filing of the application.

The commercially available Acasti, Inc. soft gel krill oil composition package label also refers to a patent teaching the treatment of patients for cardiovascular disease with enzyme-free krill oil extracts having an active phospholipid content of >5%. Sampalis et al., U.S. Pat. No. 8,057,825 (herein incorporated by reference). While a complete compositional analysis of the enzyme-free krill oil extracts was not disclosed including viscosity measurements, the reference further teaches that each capsule for clinical administration was loaded with only 800 mg of krill oil. The reference did not provide any technical details regarding any filling procedures or methods of modulation krill oil viscosity related to capsule preparation and/or filling. Consequently, one of skill in the art would expect that the viscosity of highly concentrated phospholipid krill oil compositions having phospholipid concentrations in excess of 60% would prevent encapsulation.

In one embodiment, the present invention contemplates a high phospholipid krill oil composition (e.g., for example, between approximately 60-99% (w/w) that can be subjected to a gentle drying process (e.g., for example, lyophilization, oven heating, nitrogen streaming) to remove excess water and organic solvent (e.g., for example, ethanol), where a flowable, high viscosity krill oil results when maintained at a temperature of at least 40° C. These krill oils can be extracted using either sub-critical fluids or super-critical fluids in optional combinations with a polar solvent (e.g., for example, ethanol). See, Table 1.

TABLE 1

Compositional Analysis of A Lyophilized Concentrated Phospholipid Krill Oil[a]

| | | |
|---|---|---|
| Viscosity | 140,000 Centipoise | |
| Phospholipids (g/100 g) | Total | 61.7 |
| | Phosphatidylcholine (PC) | 47.0 |
| | Alkyl Acyl Phosphatidylcholine (AAPC) | 4.5 |
| | Phosphatidylinositol (PI) | 0.75 |
| | Phosphatidylserine (PS) | 0.5 |
| | Lysophosphatidylcholine (LPC) | 2.9 |
| | Lyso Alkyl Acyl Phosphatidylcholine (LAAPC) | 0.65 |
| | Phosphatidylethanolamine (PE) | 2.8 |
| | Alkyl Acyl Phosphatidylethanolamine (AAPE) | 0.75 |
| | Cardiolipin + N-acylphosphatidylethanolamine (CL/NAPE) | 1.5 |
| | Lysophosphatidylethanolamine (LPE) | 0.35 |
| | Lyso Alkyl Acyl Phosphatidylethanolamine (LAAPE) | <0.1 |
| Astaxanthin (mg/100 g) | 40.5 | |
| Fatty Acids (% w/w) | Total n-3: 42.9 | |
| | 14:0 - 6.6 | |
| | 15:0 - 0.4 | |
| | 16:0 - 21.8 | |
| | 16:1 (n-9) - 0.6 | |
| | 16:1 (n-7) - 2.7 | |
| | 16:1 (n-5) - 0.6 | |
| | i17:0 - 0.3 | |
| | phytanic - 1.1 | |
| | 16:2 - 0.3 | |
| | 17:1 - 0.3 | |
| | i18:0 - 0.3 | |
| | 16:4 (n-1) - 0.4 | |
| | 18:0 - 1.1 | |
| | 18:1 (n-9) - 8.1 | |
| | 18:1 (n-7) - 6.1 | |
| | 18:1 (n-5) - 0.4 | |
| | 18:2 (n-6) - 2.0 | |
| | 18:3 (n-3) - 1.7 | |
| | 18:4 (n-3) - 4.9 | |
| | 20:1 (n-9) - 0.5 | |
| | 20:1 (n-7) - 0.3 | |
| | 18:1 (n-5) - 0.4 | |
| | 20:4 (n-6) - 0.4 | |
| | 20:4 (n-3) - 0.6 | |
| | 205 (n-3) EPA - 21.5 | |
| | 22:1 (n-9) - 0.6 | |
| | 21:5 (n-3) - 0.6 | |
| | 225 (n-3) - 0.5 | |
| | 22:6 (n-3) DHA - 13.1 | |
| | Others - 1.7 | |

TABLE 1-continued

Compositional Analysis of A Lyophilized Concentrated Phospholipid Krill Oil[a]

| | |
|---|---|
| Flashpoint PMCC, ° C. | 99 |
| Specific Gravity (@ 15/15° C.) | 1.0038 |
| Fecal Coliforms (grams) | Not Detected |
| *E. coli* (grams) | Not Detected |
| *Salmonella* (grams) | Not Detected |
| Aerobic plate count @ 35° C. (cfu/g) | <10 |
| Total yeast/mold (cfu/g) | <10 |
| Moisture @ 70° C. (g/100 g) | 1.9 |
| Ethanol (mL/100 mL) | 0.8 |
| Peroxide (meq $O_2$/kg fat) | <0.1 |
| TMA (mg/100 g) | 8 |
| TMAO (mg/100 g) | 1174 |

[a]avg: N = 2

Although it is not necessary to understand the mechanism of an invention, it is believed that the krill oil composition detailed in Table 1 having an approximate 60% phospholipid concentration and a viscosity of 140,000 cP is capable of undergoing encapsulation using commercially available capsule filling equipment while maintained at a temperature of at least 40° C. At this temperature range, even though highly viscous, the lack of water and organic solvent provides a semi-solid krill oil composition that imparts flowability. Although it is not necessary to understand the mechanism of the invention, it is believed that the drying of the krill oil needs to be a gentle drying in order to prevent oxidation believed responsible for the viscosity increase in high phospholipid krill oils. Consequently, it is believed that these gentle drying techniques, for example, freeze drying, nitrogen streaming or oven heat, removes excess ethanol and water as opposed to the standard oil drying methods such as falling film and thin film evaporation.

In one embodiment, the present invention contemplates encapsulating a gently-dried krill oil that was made by two step sub-critical fluid extraction. Although it is not necessary to understand the mechanism of an invention, it is believed that the present method comprises removing triglycerides by precipitation that concomitantly increases the krill oil phospholipid content to above 60% and then gently drying the high phospholipid krill oil to remove the excess water and organic solvent. In one embodiment, the gently-dried krill oil was put into soft gel capsules after heating to at least 40° C.

III. Encapsulation Methods

A. Basic Concepts

The encapsulation of liquids and semi-solids (e.g., for example, krill oil compositions) provides solutions for convenient delivery through improved oral absorption of poorly water-soluble drugs. Both hard and soft capsules can be considered and in each case the capsule wall may comprise gelatin or some other suitable polymer such as hypromellose. The choice of a hard or soft capsule will depend primarily on the components of the formulation which provides the best absorption characteristics as well as on the physical characteristics, such as the viscosity of the formulation and the temperature at which the product needs to be filled. Numerous excipients are available for formulation of lipid-based systems and their compatibilities with hard gelatin capsules have been tested. The availability of new enhanced manufacturing equipment has brought new opportunities for liquid-filled hard capsules. Commercially available filling and sealing technologies for hard capsules provides for scale-up capabilities.

When using compounds having higher molecular weights and greater lipophilicity that increase viscosity conventional formulation strategies are no longer adequate to achieve acceptable bioavailability. Cole et al., "Challenges and opportunities in the encapsulation of liquid and semi-solid formulations into capsules for oral administration" *Advanced Drug Delivery Reviews* 60:747-756 (2008). Such lipophilic formulations make use of excipients which are either liquid or semi-solid in nature and therefore the only solid oral dosage form that has good patient acceptability is a capsule.

Two types of capsules are commonly used and are classified according to the nature and flexibility of the capsule shell. Soft capsules are single unit solid dosage forms comprising a liquid or semi-solid fill and are usually oblong or oval in shape. They are formed, filled and sealed in one operation using a rotary die process. The technology is currently available from a few specialist companies.

Hard capsules are single unit dosage forms which are manufactured separately and supplied empty for filling. E. T. Cole, Hartgelatinekapseln, In: H. Sucker, P. Fuchs, P. Speiser (Eds.), *Pharmazeutische Technologie*, Georg Thieme Verlag, Stuttgart, 1991, pp. 319-320; and B. E. Jones, "Manufacture and properties of two-piece hard capsules" In: F. Podczek, B. E. Jones (Eds.), *Pharmaceutical Capsules*, Pharmaceutical Press, London, 2004, pp. 79-100. They are always cylindrical in shape, consist of a cap and body and have domed ends. Soft capsule have been used as unit dose containers for liquids for many years whereas hard capsules have conventionally been used for delivery of solids in the form of powders and pellets.

1. Encapsulation of Water-Insoluble Compounds

One characteristic of concentrated phospholipid krill oil compositions for which the liquid fill technology is applicable is related to low water solubility and concomitant increases in viscosity. The use of a capsule filled with a semi-solid formulation may be advantageous in improving bioavailability. An improvement in bioavailability may result the inclusion of polysorbate 80 which ensures complete release in a finely dispersed form and which was likely to facilitate solubilization by bile acids.

2. Physical Characteristics of Capsules

A useful polymer for the production of hard capsules comprises a gelatin compound. Additional components of a capsule shell includes, but is not limited to, water (which acts as a plasticizer), coloring agents and/or opacifiers. If an alternate to gelatin is required, hard capsules may be manufactured from hydroxypropyl methylcellulose (HPMC). Recent advances made in the HPMC capsule technology have resulted in the achievement of similar in vitro dissolution rates to gelatin capsules. The composition of a shell material for hard gelatin capsules for powder or liquid filling is identical, as are the capsule sizes.

Soft shells are generally thicker than those of hard capsules and are also most commonly manufactured from gelatin but, in contrast to hard capsules, the plasticizer includes, but is not limited to, glycerin, sorbitol and water. Soft shell capsules may also include a coloring agent and/or an opacifier. Alternative shell materials to gelatin that are either commercially available or in development, include a combination of iota carrageenan and hydroxypropyl starch, a specific potato starch and polyvinyl alcohol and the advantages and disadvantages of alternative materials to gelatin have been discussed. G. Reich, "Formulation and physical properties of soft capsules" In: F. Podczek, B. E. Jones (Eds.), *Pharmaceutical Capsules*, Pharmaceutical Press, London, 2004, pp. 201-212. The presence of a plasticizer in the soft gelatin shell can give a relatively high permeability to oxygen and it has been reported that at relative humidities of between 31 and 80%, the log of the oxygen permeability coefficient decreases linearly with decreasing glycerin content. Horn et al., "Soft gelatin capsules II: oxygen permeability study of capsule shells" *J. Pharm. Sci.* 64:851-857 (1975). Therefore, it is likely that the oxygen permeability of a sealed hard gelatin capsule will be lower than that of a soft capsule. An assessment of the smell of highly odorous products which were transferred from commercially available soft capsules into hard capsules and sealed effectively demonstrated this to be the case. Cadé et al., "Liquid filled and sealed hard gelatin capsules" *Acta Pharm. Technol.* 33:97-100 (1987).

In practice, soft gelatin capsules can perform well as oxygen barriers by modification of the type and level of plasticizer used. The primary function of the plasticizer in a soft capsule shell is to maintain the flexibility of the shell wall. The plasticizers are, however, hygroscopic and absorb moisture when exposed and it has been shown that the sorption of water by soft gelatin shells containing different plasticizers is considerably higher than is the case with hard gelatin capsules. The commonly used plasticizers for soft gelatin shells also have the ability to solubilize water-soluble compounds.

Any formulation approach should consider a potential interaction between the fill material and the capsule wall. To illustrate this point the moisture content of a range of different molecular weight PEGs at a relative humidity of 55% has been shown to vary between 18.8% for PEG 200 and b1% for the solid PEGs. Walters et al., "Moisture uptake of excipients for liquid filling into hard gelatin capsules" *Proceedings Pharmaceutical Technology Conference (Utrecht)* 18:97-101 (1999); and G. Rowley, "Filling of liquids and semi-solids into hard two-piece capsules" In: F. Podczek, B. E. Jones (Eds.), *Pharmaceutical Capsules*, Pharmaceutical Press, London, 2004, pp. 169-194. Liquid PEGs can thus only be used in low concentrations for filling hard gelatin capsules.

3. Fill Characteristics of Capsules

Fill formulations for hard gelatin capsules may be Newtonian liquids, such as oils, thixotropic or shear thinning gels or semi-solid matrix products that are filled at elevated temperatures and in which the compound is either dissolved or suspended as a fine dispersion. For example, a model system in which lactose was dispersed in poloxamers of different viscosities revealed that the limiting concentration of the dispersed phase decreased as particle size decreased and as the molecular weight of the poloxamer increased. Kattige et al., "Influence of rheological behaviour of particulate/polymer dispersions on liquid-filling characteristics for hard gelatin capsules" *Int. J. Pharm.* 316:74-85 (2006). Satisfactory filling characteristics were achieved with poloxamer F68 up to a concentration of 35% w/w when the mean particle size of lactose was 22.6 μm and 27.5% w/w when the mean particle size was 15.3 μm.

In principle, any formulation composition found to be compatible with gelatin can be used provided that the viscosity of the fill material conforms to the requirements of the filling process. The uniformity of capsule fill weights was shown to decrease as the viscosity of thermo-softened fill materials increased. Saeed et al., "Rheological Characteristics of Poloxamers and Poloxamer/Silicon Dioxide Gels in Relation to Liquid Filling of Hard Gelatin Capsules" *Proceedings Pharmaceutical Technology Conference (Athens)* 16:217-224 (1997); and Hawley et al., "Physical and chemical characterisation of theimosoftened bases for molten-filled hard gelatin capsule formulation" *Drug Dev. Ind. Pharm.* 18:1719-1739 (1992). The general guidelines for fill materials are listed in Table 2.

TABLE 2

General Guidelines for filling liquids/semi-solid fill materials into hard gelatin capsules

| Parameter | Recommendation |
|---|---|
| Temperature of fill material | Max. ~70° C. |
| Viscosity at the temperature of dosing | 10-1000 cPs |
| Dosing characteristics | Clean break from dosing nozzle Absence of "stringing" |

Compatible excipients have been categorized into three groups and are summarized below. See, Tables 3, 4 and 5. The broad categories are lipophilic liquid vehicles, semi-solid lipophilic vehicles and viscosity modifiers for lipophilic liquid vehicles and solubilizing agents, surfactants, emulsifying agents and absorption enhancers.

TABLE 3

Lipophilic liquid vehicles compatible with hard gelatin capsules

| Refined specialty oils | Medium chain triglycerides and related esters |
|---|---|
| Arachis oil | Caprylic/capric triglycerides (Akomed E, Akomed R, Miglyol 810, Captex 355) |
| Castor oil | Medium chain triglyceride (Labrafac CC) |
| Cottonseed oil | Propylene glycol diester of caprylic/capric acid (Labrafac PG) |
| Maize (corn) oil | Propylene glycol monolaurate (Lauroglycol FCC) |
| Olive oil | Fractionated coconut oil (Miglyol 812) |
| Sesame oil | Caprylic/capric/diglyceryl succinate (Miglyol 829) |
| Soybean oil | Medium chain diesters of propylene glycols (Miglyol 840) |
| Sunflower oil | Partial ester of diglycerides with natural fatty acids (Softisan 645) |

TABLE 4

Semi-solid lipophilic vehicles and viscosity modifying substances compatible with hard gelatin capsules

| Substance | Tradename |
|---|---|
| Arachis oil | Groundnut 36 |
| Castor oil | Cutina HR |
| Cottonseed oil | Sterotex |

TABLE 4-continued

Semi-solid lipophilic vehicles and viscosity modifying substances compatible with hard gelatin capsules

| Substance | Tradename |
|---|---|
| Palm oil | Softisan 154 |
| Soybean oil | Akosol 407 |
| Aerosil | |
| Cetosteryl alcohol | |
| Cetyl alcohol | |
| Semi-synthetic glycerides based on hydrogenated vegetable oils | Gelucires 33/01, 39/01, 43/01 |
| Glyceryl behenate | Compritol 888 ATO |
| Glyceryl palmitostearate | Precirol ATO 5 |
| Hydrogenated coco-glycerides | Softisans 100, 142 |
| Caprylic/capric/stearic triglycerid | Softisan 378 |
| Bis-diglyceryl/caprylate/caprate/stearate/adipate | Softisan 649 |
| Stearic acid | |
| Steryl alcohol | |

TABLE 5

Solubilizing agents, surfactants, emulsifying agents and absorption enhancers compatible with hard gelatin capsules

| Substance | Tradename |
|---|---|
| Propylene glycol monocaprylate | Capryol 90 |
| Polyglycolized glycerides | Gelucire 44/14, 50/13 |
| Polyoxyl-40 hydrogenated castor oil | Cremophor RH 40 |
| Glycerol monostearate/di-triglycerides + glycerin | Imwitor 191 |
| Glyceryl monocaprylate | Imwitor 308 a |
| Glyceryl cocoate/citrate/lactate | Imwitor 380 |
| Glyceryl mono-di-caprylate/caprate | Imwitor 742 |
| Isosteryl diglyceryl succinate | Imwitor 780 K |
| Glyceryl cocoate | Imwitor 928 |
| Glyceryl caprylate | Imwitor 988 |
| Oleoyl macrogol-8 glycerides | Labrafil M 1944 CS |
| Linoleoyl macrogolglycerides | Labrafil M 2125 CS) |
| PEG-8 caprylic/capric glycerides | Labrasol) |
| Lauric acid | |
| Propylene glycol laurate | Lauroglycol 90 |
| Oleic acid | |
| PEG MWN4000 | |
| Polyglycerol dioleate | Plurol Oleique CC 497 |
| Polyoxyethylene-polyoxypropylene copolymer | Poloxamer 124, 188 |
| Partial glycerides of hydroxylated unsaturated fatty acids | Softigen 701 |
| PEG-6 caprylic/capric glycerides | Softigen 767 |
| Polyoxyethylene glyceryl trioleate | Tagat TO |
| Polyoxyethylene(20)sorbitan monooleate | Tween 80 |

6. Capsule Filling Equipment

The equipment that is necessary to enable automatic filling of hard gelatin capsules with either hot or cold liquid is available in a range of filling rates, from laboratory to production scale. The liquid to be filled is usually dispensed by volume and the machines all meet the conventional requirements to allow for the industrial manufacture of liquid-filled capsules. Cole E., "Liquid-filled and-sealed hard gelatin capsule technologies" In M. J. Rathbone, J. Hadgraft, M. S. Roberts (Eds.), *Modified-Release Drug Delivery Technology*, Marcel Dekker, New York, 2003, pp. 177-188. A variety of commercially available capsule filling machines are available. See, Table 6.

TABLE 6

Major capsule-filling machines for liquid filling of hard gelatin capsules up to production scale

| Machine type | Filling action | Approximate filling rate (capsules/h) |
|---|---|---|
| Robert Bosch GmbH | | |
| GKF 1400 L | Intermittent motion | 60,000 |
| GKF 701 L | | 36,000 |
| Harro Hoefliger GmbH | | |
| KFM III-C | Intermittent motion | 5,000 |
| IMA Zanasi Division | | |
| Zanasi 6/12 | | 6000-12,000 |
| Zanasi 25/40 | | 25,000-40,000 |
| Zanasi Lab 8/16 | All intermittent motion | 8000-16,000 |
| Zanasi Plus 32E/48E/70E/85E | | 32,000-85,000 |
| MG2 | | |
| MG Compact | | 6000-96,000 |
| MG Futura | All continuous motion | 6000-96,000 |
| Planeta 100 | | 100,000 |
| Qualicaps | | |
| F-5 | | 4000 |
| F-40 | All continuous motion | 30,000 |
| F-80 | | 60,000 |
| F-120 | | 90,000 |
| F-150 | | 120,000 |
| Schaefer Technologies Inc. | | |
| LF-10 | Semi-automatic | 10,000-25,000 |
| Bonapace | | |
| IN-CAP | Intermittent motion | 3000 |

A capsule-filling machine for dosing hard capsules with high viscosity pastes and which operates by extrusion of a cylinder of material directly into a capsule body and an alternate system for filling highly viscous materials has been developed that operates by filling hot mixtures under high pressure by means of time controlled pneumatic valves and which has been used in a production environment for many years. Strickrodt J., "Fully automatic process for filling high viscosity pastes into hard gelatin capsules" *Pharm. Ind.* 52:1276-1279 (1990); and Bohne et al., "A new process for filling hard gelatin capsules with semisolid materials. Experiences in development and production" *Pharm. Ind.* 53:1127-1134 (1991).

B. Thixotropic Capsule Carriers for High Viscosity Compositions

Due the above described problems regarding the ability to fill capsules with high viscosity compositions, one proposed solution in the art offered to solve this problem was to suspend the high viscosity compositions in a thixotropic carrier to facilitate capsule filling.

Conventional carrier compositions are either liquid at ambient temperature or they become liquid with heating and they are poured into the hard or soft capsules as a liquid. When these carrier compositions are liquid at ambient temperature, the active agents incorporated therein must be dissolved. Consequently, they cannot be added at high loadings and it is difficult to maintain them in a uniform distribution within the capsule. Carrier compositions that are solid at ambient temperature require heating before they can be poured into the capsules and the heat can damage the capsule walls, reduce the activity of the active ingredient or damage other heat sensitive ingredients.

Thixotropic carriers were suggested to alleviate the problems encountered in filling capsules with highly viscous compositions because active agents may be easily mixed together by stirring and stable uniform dispersions with high loadings can be achieved because the carrier becomes semi-solid when the stirring is stopped. For example, one thixotropic carrier has been reported that includes vegetable oil (84%-95%), a viscosity modifier (1%-9%) and a surface active agent (1%-15%). Viscosity modifiers may include, but are not limited to, glyceryl palmitol stearate and glyceryl behenate. Surface active agents may include, but are not limited to, polyglyceryloleate.

A thixotropic gelatin carrier composition may be used as a vehicle in the manufacture of soft or hard gelatin capsule. These compositions may range from about 84% to 95% of a vegetable oil, from about 1% to 9% of a viscosity modifier and from about 1% to 15% of a surface active agent. Usually, when a carrier composition is stirred it becomes fluid and active solids may be dispersed in the carrier during stirring. When the stirring is stopped, the carrier becomes a semi-solid and maintains the active solids in a stable uniform dispersion. Although it is not necessary to understand the mechanism of an invention, it is believed that up to about 50% by weight of active solids can be dispersed in a thixotropic carrier composition and the active solids can include vitamins, pharmaceuticals or nutriceuticals or combinations thereof. Matthews J., "Thixotropic Gelatin Carrier Composition" U.S. Pat. No. 6,365,181 (herein incorporated by reference).

IV. Gently Dried Krill Oils

In one embodiment, the present invention contemplates a method comprising gentle drying a concentrated phospholipid krill oil. In one embodiment, the gentle drying comprises lypophilization. In one embodiment, the gentle drying comprises oven heat. In one embodiment, the gently drying comprises a nitrogen stream. Although it is not necessary to understand the mechanism of an invention the gentle drying encompasses any process that will efficiently remove water and organic solvent (e.g., ethanol) from a krill oil without inducing oxidation-induced increases in viscosity.

In one embodiment, the present invention contemplates a method for encapsulation of krill oil with a phospholipid content of 60% or more subsequent to a gentle drying method. As described in detail above, encapsulation of concentrated phospholipid krill oils has previously proven difficult due to the high viscosity of the oil. The present invention solves this problem by creating a semi-solid concentrated phospholipid krill oil at a temperature of at least 40° C. having a physical characteristic of flowability, even though the viscosity may be measured between 100,000-3,000,000 cP.

1. Lyophilization

Freeze-drying, also known as lyophilisation, lyophilization, or cryodesiccation, is a dehydration process typically used to preserve a material or make the material more convenient for handling (e.g., for example, capsule filling). Freeze-drying works by freezing a material and then reducing the surrounding pressure to allow the frozen water in the material to sublimate directly from a solid phase to a gas phase.

a. The Freeze-Drying Process

It is generally accepted that there are at least four stages in the complete drying process including, but not limited to, pretreatment, freezing, primary drying, and secondary drying.

Pretreatment includes any method of treating the product prior to freezing. This may include, but is not limited to, concentrating the product, formulation revision (i.e., addition of components to increase stability, preserve appearance, and/or improve processing), decreasing a high-vapor-pressure solvent, and/or increasing the surface area.

The freezing step is often done by placing a material in a freeze-drying flask and rotating the flask in a bath, called a shell freezer, which is cooled by processes including, but not limited to, mechanical refrigeration, dry ice and methanol, and/or liquid nitrogen. Alternatively, commercially available freeze-drying machines are available (e.g., for example, a lyophilizer). In this step, the material is cooled to below its triple point, typically defined as the lowest temperature at which the solid and liquid phases of the material can coexist. This ensures that sublimation, rather than melting, will occur in the following steps. Larger crystals are easier to freeze-dry. To produce larger crystals, the product should be frozen slowly or can be cycled up and down in temperature. This cycling process is called annealing. Alternatively, the freezing may be done rapidly, in order to lower the material to below its eutectic point quickly, thus avoiding the formation of ice crystals. Usually, the freezing temperatures are between −50° C. and −80° C. Amorphous materials do not have a eutectic point, but they do have a critical point, below which the product must be maintained to prevent melt-back or collapse during primary and secondary drying.

During the primary drying phase, the pressure may be lowered to a range of a few millibars, and enough heat can be supplied to the material for the ice to sublime. The amount of heat necessary can be calculated using the sublimating molecules' latent heat of sublimation. In this initial drying phase, about 95% of the water in the material may be sublimated. This phase may be slow (e.g., for example, several days), because, if too much heat is added, the material's structure could be altered. In this phase, pressure can be controlled through the application of partial vacuum. Vacuum is believed to speed up the sublimation, making it useful as a deliberate drying process. Furthermore, a cold condenser chamber and/or condenser plates provide a surface(s) for the water vapor to re-solidify on. This condenser plays no role in keeping the material frozen; rather, it prevents water vapor from reaching the vacuum pump, which could degrade the pump's performance. Condenser temperatures are typically below −50° C. (−60° F.). Of note is that, in this range of pressure, the heat is brought mainly by conduction or radiation; the convection effect is negligible, due to the low air density.

A secondary drying phase aims to remove unfrozen water molecules, since the ice was removed in the primary drying phase. This part of the freeze-drying process may be governed by the material's adsorption isotherms. In this phase, the temperature can be raised higher than in the primary drying phase, and can even be above 0° C., to break any physico-chemical interactions that have formed between the water molecules and the frozen material. Usually the pressure can also be lowered to encourage desorption (typically in the range of microbars, or fractions of a pascal). However, there are products that benefit from increased pressure as well. After the freeze-drying process is complete, the vacuum is usually broken with an inert gas, such as nitrogen, before the material is sealed. At the end of the operation, the final residual water content in the product is extremely low, around 1% to 4%.

b. Properties of Lyophilized Products

If a freeze-dried substance is sealed to prevent the reabsorption of moisture, the substance may be stored at room temperature without refrigeration. Freeze-drying also causes less damage to the substance than other dehydration methods using higher temperatures. Freeze-drying does not usually cause shrinkage or toughening of the material being dried.

In addition, flavors, smells and nutritional content generally remain unchanged, making the process popular for preserving edible substances (e.g., for example, krill oil compositions). However, water is not the only chemical capable of sublimation, and the loss of other volatile compounds such as acetic acid (vinegar) and alcohols can yield undesirable results.

Freeze-dried products can be rehydrated (reconstituted) much more quickly and easily because the process leaves microscopic pores. The pores are created by the ice crystals that sublimate, leaving gaps or pores in their place.

2. Lyophilization of Concentrated Phospholipid Krill Oil Products

In some embodiments, the present invention contemplates a method that effectively reduces the water content and organic solvent content of a concentrated phospholipid krill oil product to create a flowable semi-solid at a temperature of at least 40° C. In one embodiment, the flowable concentrated phospholipid semi-solid krill oil product is encapsulated in to a capsule.

In general, the present invention may be practiced on any krill oil composition regardless of the method of making. Nonetheless, it is preferred that the concentrated phospholipid krill oil is produced using fresh krill (e.g., generally on board the trawler), where the whole krill is disintegrated and subjected to hydrolytic enzymatic digestion, or disintegrated and subjected to denaturation by heating. Both hydrolytic enzymatic digestion and/or heat denaturation produces a phospholipid-peptide complex (PPC) krill meal composition that is capable of krill oil extraction.

Subsequent to hydrolytic enzyme digestion and/or heat denaturation, the PPC may be subjected to a low speed centrifugation (e.g., ~2000 g) that separates the krill exoskeleton from the peptide\lipid biomass (PPC). This process has the added advantage of producing low fluoride krill oil compositions as the vast majority of fluoride is located in the exoskeleton. The PPC may then be used as a starting material for krill oil extraction using either a polar solvent (e.g., ethanol), a sub-critical gaseous fluid or a supercritical gaseous fluid (e.g., for example, carbon dioxide). These extractions may be peformed individually or in series and in any combination.

These process have been reported to result in the production of concentrated phospholipid krill oil compositions having high viscosity. See, Bruheim et al., United States Patent Application Publication No. 2013/0225794 (herein incorporated by reference); and Sampalis et al., U.S. Pat. No. 8,586,567 (herein incorporated by reference). As discussed above, conventionally extracted krill oil viscosity is proportional to phospholipid content. There are no available reports of successful encapsulation of krill oil having a phospholipid concentration of above 50% (e.g., Omenia®, Acasti, Inc.). Although it is not necessary to understand the mechanism of an invention it is believed that the encapsulation of a 60% phospholipid krill oil is not possible with commercially available capsule filling equipment because the resulting viscosity results in a solid composition at a temperature of at least 80° C.

Such concentrated phospholipid krill oil compositions may then be lyophilized as described above into a low water content, low organic solvent content semi-solid krill oil product that is flowable at a temperature of at least 40° C. This semi-solid phospholipid concentrate krill oil composition may then encapsulated using commercially available capsule filling equipment.

V. Phospholipid Enrichment by Small Molecule Organic Solvent Fractionation

A. Krill Oil Extraction from Krill Meal

Commercial extraction of krill oil from dried krill meal is mainly performed by ethanol extraction. In the process, triglycerides are co-extracted with the phospholipids and the amount of polar lipids in the obtained krill oil decided by the krill meal composition. In some embodiments, the present invention contemplates a method for concentrating an ethanol-extracted krill meal polar lipid fraction by a reduction in temperature during an ethanol evaporation step. Although it is not necessary to understand the mechanism of an invention, it is believed that the precipitation of triglycerides from an extracted krill oil composition results in a greater phospholipid percentage (w/w) as the originally extracted concentrated phospholipid krill oil composition.

Crude krill oil extracted from Antarctic krill (*Euphausia superba*) contains typically around 40% phospholipids and 300 mg/kg poly-unsaturated fatty acids (PUFAs; e.g., for example, omega-3 PUFAs). In one embodiment, the present invention contemplates a krill oil composition comprising greater than 300 mg/kg omega-3 PUFA product and at least 60% phospholipids. Although it is not necessary to understand the mechanism of an invention, it is believed that by modifying krill oil extraction methods to increase the phospholipid content, the omega-3 PUFA concentration concomitantly increases.

Krill oil production based on ethanol extraction of krill meal can be performed on-board fishing vessels. In one embodiment, an ethanol evaporation step comprises separation and crystallization of triacylglycerol (TAG). Although it is not necessary to understand the mechanism of an invention, it is believed that TAG separation and crystallization can be obtained by controlling water content and temperature level. In one embodiment, a>60% phospholipid ethanol soluble fraction is isolated subsequent to removal of a non-soluble fraction.

The data provided herein illustrates a central composite design within a temperature range of between 4.1° C. and −24.1° C. showing effects on lipid and fatty acid composition, sodium chloride (NaCl) and astaxanthin levels in ethanol soluble lipids having a water content in the ethanol phase of between 0-10%. These variables are futher assesed using response surface models having an $R^2$>0.74. Concentrations of a combined polar lipid fraction (e.g., for example, PE+PC+lyso-PC) were observed to be above 60%.

Optimal conditions to obtain increased polar lipid levels were observed when the ethanol phase comprised 10% water at a temperature of 249° K. (−24.1° C.), where predicted levels of polar lipids based on these conditions are approximately 73%. For example, an above 60% level of polar lipids can be obtained by using: i) pure ethanol at a temperature level of 249° K. (−24.1° C.); ii) a water content below 6.0% at a temperature level of 277.3° K. (4.1° C.); and iii) combinations within the conditions specified in (i) and (ii). Product yield is positively correlated to temperature (K) and negatively to water content. Predicted levels for the above specified conditions giving >60% polar lipid content is 66.0% and 64.1%, respectively.

Astaxanthin content was observed to be strongly negatively correlated to water content and the highest carry over to the polar lipids is obtained using pure ethanol. Pure ethanol concentration also coincides with lowest level of undesired compounds including, but not limited to, sodium chloride (NaCl), cholesterol, trimethylamine oxide (TMAO) and trimethylamine (TMA).

Omega-3 PUFA retention was maximal during extractions at low temperature and a 1.5% water content. These fractional conditions produced a solid fraction and a soft sediment fraction that separated easily. In one embodiment, the soft sediment composition comprises an ethanol insoluble phase including, but not limited to, the separated and crystallized TAGs, <1% polar lipids, and approximately 559 mg/kg astaxanthin (cf. 222 mg/kg astaxanthin in the krill oil fraction). Although it is not necessary to understand the mechanism of an invention, it is believed that the presently disclosed ethanol fractionation method may be applied to concentrate astaxanthin esters from a krill oil fraction.

It is further believed that water content in the ethanol phase has a strong impact on the composition and yield of polar lipids. For example, the extracted polar lipid content depends on both ethanol water content and krill meal moisture content. In some embodiments, the present invention contemplates an ethanol fractionation method that controls ethanol water content and krill meal moisture content to create a krill oil comprising at least 60% polar lipids.

In one embodiment, the present invention contemplates an organic solvent (e.g., for example, ethanol) fractionation method that produces a concentrated phospholipid krill oil composition. In one embodiment, the concentrated phospholipid krill oil composition further comprises lipids, fatty acids, astaxanthin and sodium chloride (NaCl). In one embodiment, the ethanol fractionation method partitions out TMAO and TMA from the concentrated phospholipid krill oil composition.

B. Phospholipid Enrichment: Effects of Ethanol Water Content and Extraction Temperature A two-factorial rotatable central composite design (CCD) was used to study the effect of temperature and concentration of water (w/w %) in the ethanol phase on yield and composition of the lipids in the sediment and ethanol phase. Meyers et al., In: *Response Surface Methodology. Process and Product Optimization Using Designed Experiments* John Wiley & Sons, New York, N.Y. (USA) (2002). A total of 11 experimental settings were used with three replications of the centre point. See, Table 7.

TABLE 7

Coded and experimental values for the experimental design variables.

| ENO. | Coded value | Water (%) | Temperature (° C.) | (K) |
|---|---|---|---|---|
| 1 | −1   −1   | 1.5 | −20.0 | 253.2 |
| 2 | 1    −1   | 8.5 | −20.0 | 253.2 |
| 3 | −1    1   | 1.5 | 0.0 | 273.2 |
| 4 | 1     1   | 8.5 | 0.0 | 273.2 |
| 5 | −1.41  0  | 0.1 | −10.0 | 263.2 |
| 6 | 1.41   0  | 9.9 | −10.0 | 263.2 |
| 7 | 0    −1.41| 5.0 | −24.1 | 249.0 |
| 8 | 0     1.41| 5.0 | 4.1 | 277.3 |
| 9 | 0     0   | 5.0 | −10.0 | 263.2 |
| 10| 0     0   | 5.0 | −10.0 | 263.2 |
| 11| 0     0   | 5.0 | −10.0 | 263.2 |

The distance ($\alpha$) from the centre point to the axial points (star points) was calculated based on the equation $\alpha=(2k)_{1/4}$, were k is the number (2) of independent variables. The temperature was varied between 249.0 and 277.3 K (+24.1° C. and +4.1° C., respectively), and the water content was varied between 0.1% (w/w) and 9.9% (w/w), respectively. For practical reasons, the experiments were run in blocks depending on the temperature level.

1. Acetone Fractionation of Krill Oil

The krill oil used as a starting material in this study contained approximately equal levels of polar and neutral lipids. Acetone fractionation was performed to establish the obtainable level based on current industrial lecithin de-oiling practice. The level of polar lipids could be increased to 72% with a reduction in neutral lipids to 3.4%. The yield of acetone insoluble matter was 44.5%. In contrast, the acetone soluble fraction contained low level of polar and high level of neutral lipids. See, Table 8.

TABLE 8

Composition (w/w %) and yield (% of starting material) of lipids after acetone fractionation of Rimfrost krill oil.

|  |  | Rimfrost Batch# | Acetone insoluble fraction | Acetone soluble fraction |
|---|---|---|---|---|
| Ash | g/100 g | 3.7 | NA | NA |
| Astaxanthin esters[a] | mg/kg | 222 | 15 | 354 |
| Free astaxanthin | mg/kg | <2 | <2 | 2 |
| TMA-N | mg N/100 g | 43 | 47 | <1 |
| TMAO-N | mg N/100 g | 73 | 44 | 2 |
| NaCl | g/100 g | 1.4 | NA | NA |
| Water | g/100 g | 0.23 | 2.1 | NA |
| TAG | g/100 g | 38 | 1.8 | 56 |
| DAG | g/100 g | 0.7 | <0.5 | 1.2 |
| MAG | g/100 g | <1 | <1 | <1 |
| FFA | g/100 g | 2.7 | <0.5 | 4.2 |
| Cholesterol | g/100 g | 2.2 | 0.9 | 2.8 |
| Cholesterol esters | g/100 g | <0.5 | <0.5 | <0.5 |
| PE | g/100 g | 1.8 | 2.2 | <0.5 |
| PI | g/100 g | <1 | <1 | <1 |
| PS | g/100 g | <1 | <1 | <1 |
| PC | g/100 g | 41 | 67 | 11 |
| Lyso-PC | g/100 g | 1.2 | 2.6 | <0.5 |
| Polar lipids | g/100 g | 44.4 | 72 | 11.3 |
| Neutral lipids | g/100 g | 44 | 3.4 | 63.9 |
| Sum lipids | g/100 g | 88.4 | 75.4 | 75.3 |
| Yield | w/w % | — | 44.5 | 60.9 |

TAG—triacylglycerols;
DAG—diacylglycerols;
MAG—monoacylglycerols;
FFA—free fatty acids;
Chol—cholesterol;
Chol-ester—cholesterol esters;
PE—phosphatidylethanolamine;
PI—phosphatidylinositol;
PS—phosphatidylserine;
PC—phosphatidylcholine;
Lyso-PC—lyso phospahatidylcholine;
Polar—polar lipids = PE + PC + Lyso-PC;
Neutral—neutral lipids = TAG + DAG + FFA + Chol + Chol-ester;
NA—not analyzed.
[a]Given as astaxanthin equivalents.

Most of the astaxanthin esters and cholesterol followed the acetone phase, with only 6.8% and 40.9%, respectively, of the initial level found in the obtained polar lipid fraction. TMA and TMAO was less soluble in the acetone and concentrated quantitatively in the polar lipids. The observed levels indicate some loss of TMAO during the processing, and might be linked to redox reactions and formation of TMA. The latter compound is volatile and may, to some extent, be removed during evaporation of the acetone after the fractionation process.

2. Ethanol Fractionation of Krill Oil

Ethanol fractionation of krill oil for the concentration of polar lipids was evaluated by use of a 2-factorial CCD within a temperature range of between −24.1° C. to 4.1° C.

and an ethanol water content between 0.1% (w/w) and 9.9% (w/w). See, Table 7. The starting material, Rimfrost krill oil, contained 0.23 g/100 g moisture and this was corrected for when adjusting the water content in the ethanol phase. See, Table 8. Moisture content in the krill oil was quantified and validated by spiking of samples to a 1% and 2% level using the Karl Fischer technique. Krakeli et al., "Matriksinterferenser i krillolje ved måling av vanninnhold (KF)" *Nofima notat.* (2015). A retrieval degree of 101.7% and 98.2%, respectively, confirmed a feasible use of the method to quantify moisture content in this matrix.

Figure 9A:
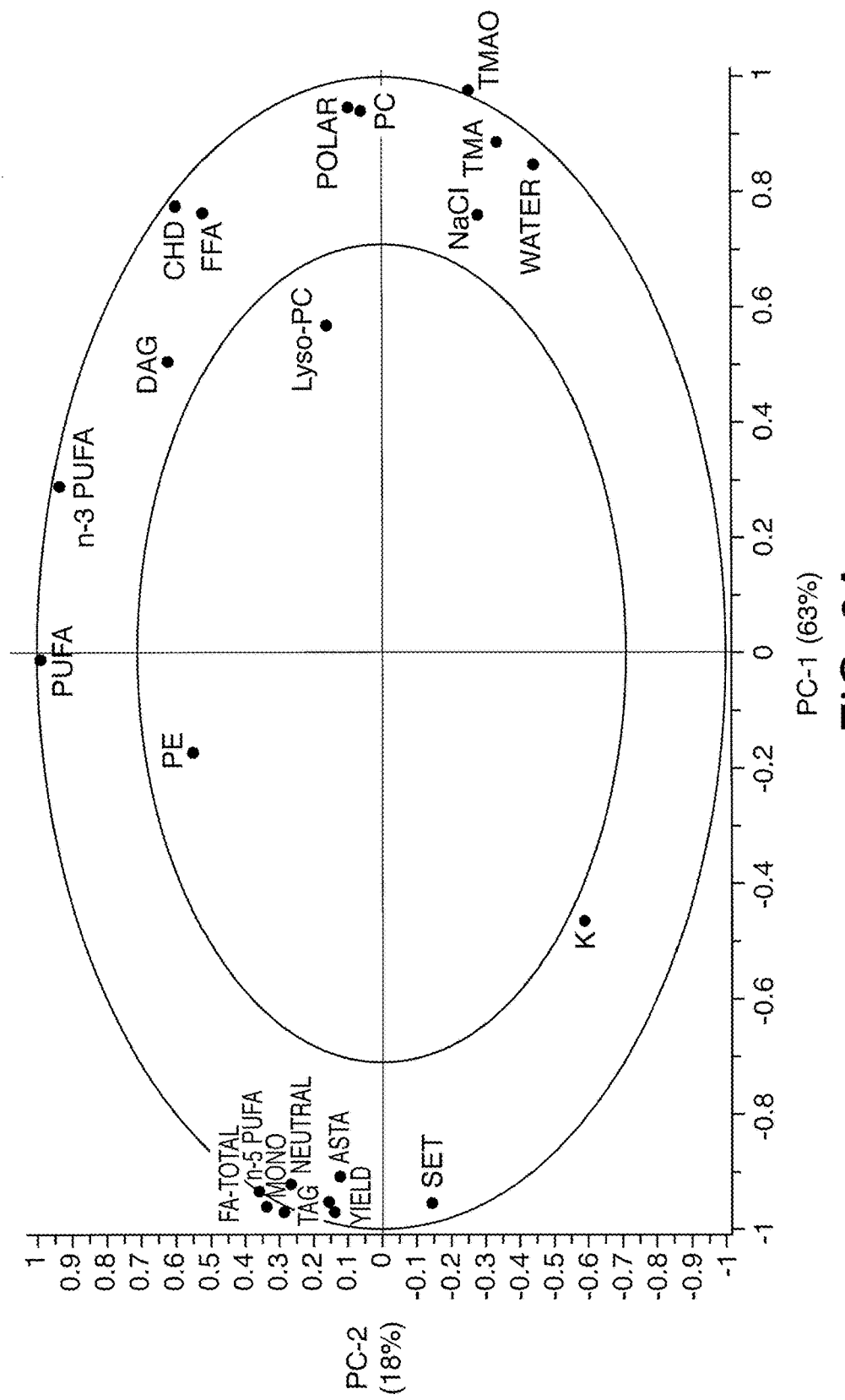

The data show an extraction of polar lipids above 60% (w/w) based on several of the experimental conditions with the highest level of 70.8% (e.g., ENo 2). See, Table 9.

gests that lowering the extraction temperature appears to increase the concentration of polar lipids in the ethanol extract (e.g., positively correlated with temperature). In contrast, a lowered extraction temperature appears to decrease the concentration of DAG, cholesterol and FFA, and in part to PUFA and n-3 PUFA in the ethanol extract (e.g., negatively correlated with temperature). The variance of lyso-PC and PE were explained by less than 50%. A score plot shows groups of experimental conditions giving a comparable extracted lipid fraction composition. FIG. 9B. To the left, ENo 3 and 5 experimental conditions provide the highest level (e.g., most concentrated) of neutral lipids and astaxanthin esters. To the right, ENo 2 and 6 experimental conditions provide the highest level (e.g., most concen-

TABLE 9

Composition (w/w %), yield (% of starting material) and astaxanthin (mg/kg) in ethanol soluble components.

| ENo | FFA | Chol | Chol-ester | MAG | DAG | TAG | Neutral | PE | PI | PS | PC | Lyso-PC | Polar | NaCl | Yield | Asta |
|---|---|---|---|---|---|---|---|---|---|---|---|---|---|---|---|---|
| 1  | 3.7 | 3.3 | <0.5 | <1 | 0.8 | 17  | 24.7 | 2.0 | <1 | <1 | 61 | 2.1 | 64.7 | 1.9 | 63.9 | 60  |
| 2  | 3.6 | 3.3 | <0.5 | <1 | 1.0 | 3.5 | 11.5 | 1.6 | <1 | <1 | 67 | 2.7 | 70.8 | 2.7 | 44.2 | 15  |
| 3  | 2.4 | 2.7 | <0.5 | <1 | 0.6 | 23  | 28.5 | 2.0 | <1 | <1 | 53 | 2.4 | 57.5 | 1.5 | 73.0 | 72  |
| 4  | 3.6 | 3.0 | <0.5 | <1 | 0.9 | 7.8 | 15.4 | 1.8 | <1 | <1 | 62 | 1.6 | 65.5 | 1.9 | 56.9 | 28  |
| 5  | 3.0 | 2.6 | <0.5 | <1 | 0.9 | 24  | 30.3 | 1.7 | <1 | <1 | 48 | 1.5 | 51.1 | 1.4 | 74.9 | 114 |
| 6  | 3.8 | 3.1 | <0.5 | <1 | 0.8 | 3.6 | 11.3 | 1.6 | <1 | <1 | 62 | 2.4 | 66.3 | 2.5 | 45.3 | 17  |
| 7  | 4.0 | 3.4 | <0.5 | <1 | 0.9 | 6.5 | 14.9 | 1.7 | <1 | <1 | 61 | 2.2 | 64.8 | 1.7 | 50.6 | 25  |
| 8  | 2.7 | 2.6 | <0.5 | <1 | 0.7 | 12  | 17.7 | 2.0 | <1 | <1 | 54 | 1.9 | 58.1 | 1.5 | 64.8 | 38  |
| 9  | 3.6 | 3.1 | <0.5 | <1 | 1.0 | 12  | 19.6 | 2.4 | <1 | <1 | 56 | 2.0 | 60.1 | 1.6 | 62.2 | 38  |
| 10 | 3.7 | 3.1 | <0.5 | <1 | 1.0 | 8.7 | 16.7 | 2.3 | <1 | <1 | 59 | 2.4 | 63.5 | 1.6 | 59.6 | 29  |
| 11 | 4.2 | 3.5 | <0.5 | <1 | 1.1 | 9.6 | 18.4 | 2.4 | <1 | <1 | 61 | 2.4 | 66.0 | 1.6 | 59.1 | 28  |

FFA—free fatty acids;
Chol—cholesterol;
Chol-ester—cholesterol esters;
MAG—monoacylglycerols;
DAG—diacylglycerols;
TAG—triacylglycerols;
Neutral—neutral lipids = FFA + Chol + DAG + TAG;
PE—phosphatidylethanolamine;
PI—phosphatidylinositol;
PS—phosphatidylserine;
PC—phosphatidylcholine;
Lyso-PC—lyso phospahatidylcholine;
Polar—polar lipids = PE + PC + Lyso-PC;
Asta—Astaxanthin esters expressed as astaxanthin equivalents These polar lipid levels are close to levels obtained using acetone fractionation (e.g., 72%, w/w). See, Table 8. The obtained yield was also at approximately the same level (~44%) and confirms that ethanol extraction may be used as an alternative fractionation solvent to acetone.

Principal Component Analysis (PCA) of the combined acetone/ethanol experimental settings and all measured responses shows an explained variance by the first and second Principal Component (PC) of 63% and 19%, respectively. See, FIG. 9A. The third and fourth PC (not shown) explained 8% and 5%, respectively, of the variance. The first PC explains the variance in polar and neutral lipids and astaxanthin esters, and the second PC the variance in PUFA. The loading plot shows a negative correlation between yield and the level of polar lipids in the ethanol soluble fraction. The level of polar lipids are associated with PC, TMAO, TMA and NaCl, and the water content in the ethanol phase. The level of neutral lipids in the ethanol soluble fraction are associated with TAG, astaxanthin esters and n-6 PUFA. The latter might indicate a higher level of n-6 PUFA in TAG compared to PL.

The temperature level is in part correlated to the level of neutral lipids and astaxanthin. The data shown herein sugtrated) of polar lipids and NaCl. At the top, the ENo 11 experimental condition gave the highest level (e.g., most concentrated) of DAG, cholesterol and FFA. The fatty acid composition and TMAO/TMA levels were only analyzed under the ENo 1-4 experimental conditions. However, the inclusion of these parameters had only minor impact on the position of the respective samples in the score plot, and improved the explained variance by PC1 from 62% to 63% and PC2 from 15% to 19%. The ENo 11 experimental condition showed some deviations from the ENo 9 and Eno 10 experimental conditions, however, Eno 11 was not identified as an outlier based on the default Unscrambler software settings. See, FIG. 9B.

Figure 10D:
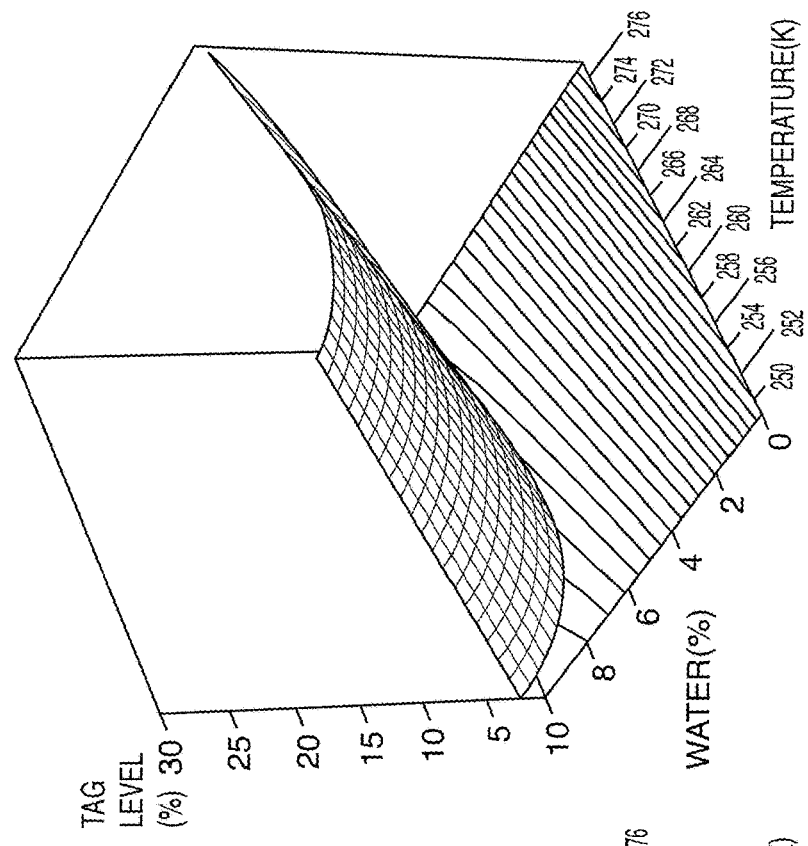
Figure 10C:
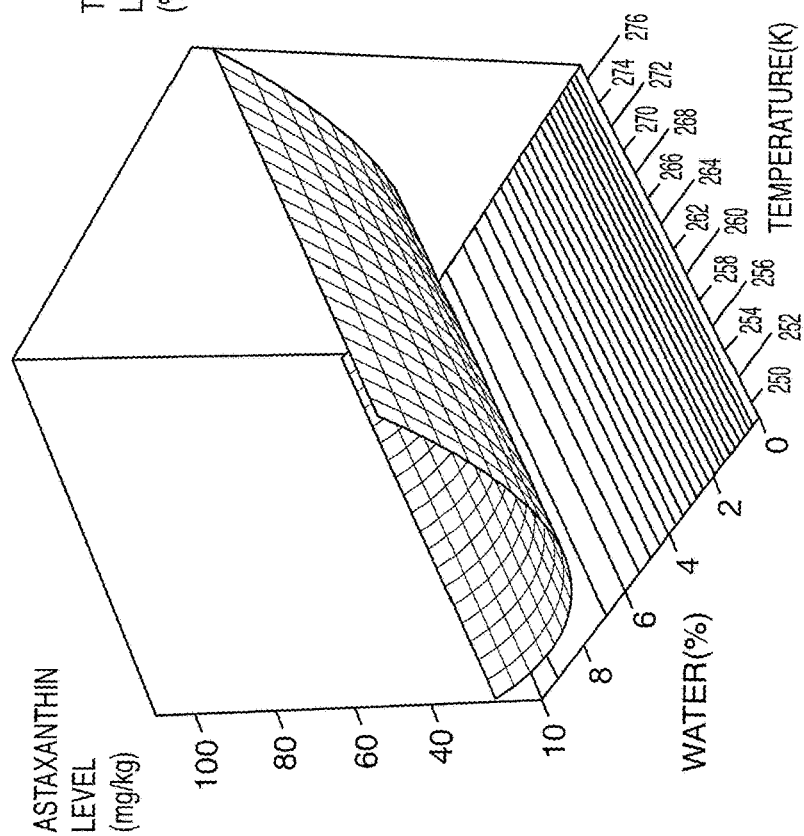
Figure 10E:
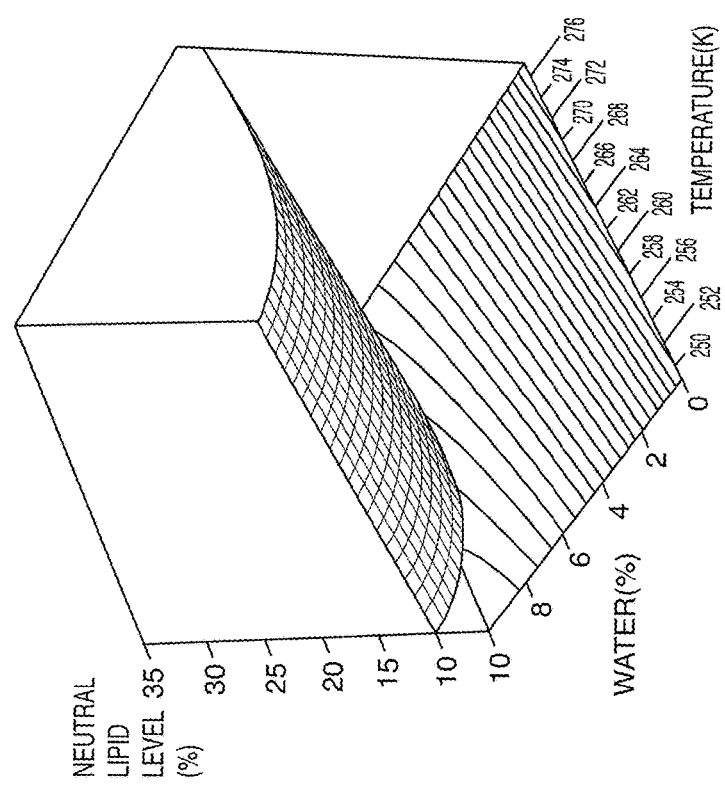

Overall, a response surface modelling of the assessed variables showed a complex and different behavior of the chemical constituents depending on their polarity and solubility in the ethanol phase. For most of the variables, satisfactory models with $R^2 > 0.88$ were achieved. See, Table 10 and FIG. 10.

TABLE 10

Response models after backward elimination of nonsignificant (NS) regression coefficients representing composition (w/w %), and yield (%) of ethanol soluble components.

| | FFA | Chol | Asta | TAG | Neutral | PE |
|---|---|---|---|---|---|---|
| Intercept | −1.50E+02 | 6.43E+00 | 1.04E+02 | −5.39E+01 | −7.46E+00 | −1.61E+02 |
| T | 1.25E+00[a] | NS | NS | 2.99E−01 | 1.46E−01 | 1.23E+00 |
| $T^2$ | −2.54E−03 | −5.38E−05 | NS | NS | NS | −2.34E−03 |
| W | −2.18E+00 | NS | −2.12E+01 | NS | −3.39E+00 | NS |
| $W^2$ | −1.87E−02[b] | −1.11E−02[c] | 1.31E+00 | 1.79E−01 | 1.49E−01 | −2.73E−02 |
| T × W | 9.29E−03 | 5.61E−04 | NS | −1.46E−02 | NS | 9.38E−04 |
| $R^2$ | 0.918 | 0.775 | 0.925 | 0.980 | 0.969 | 0.935 |

| | Lyso-PC | PC | Polar | NaCl | Yield |
|---|---|---|---|---|---|
| Intercept | 1.95E+00 | 1.34E+02 | 1.35E+02 | 1.59E+00 | −6.41E+01 |
| T | NS | −3.10E−01 | −2.99E−01 | NS | 5.22E−01 |
| $T^2$ | NS | NS | NS | NS | NS |
| W | 1.20E+00 | NS | NS | 8.48E−01 | −2.77E+00 |
| $W^2$ | NS | NS | NS | 1.74E−02 | NS |
| T × W | −4.43E−03[d] | 4.73E−03 | 484E−03 | −3.50E−03 | NS |
| $R^2$ | 0.462 | 0.770 | 0.742 | 0.885 | 0.977 |

T—temperature in Kelvin;
W—water content (%) in ethanol phase;
NS—not significant
[a] p = 0.052;
[b] p = 0.058;
[c] p = 0.097;
[d] p = 0.0502.

Figure 7:
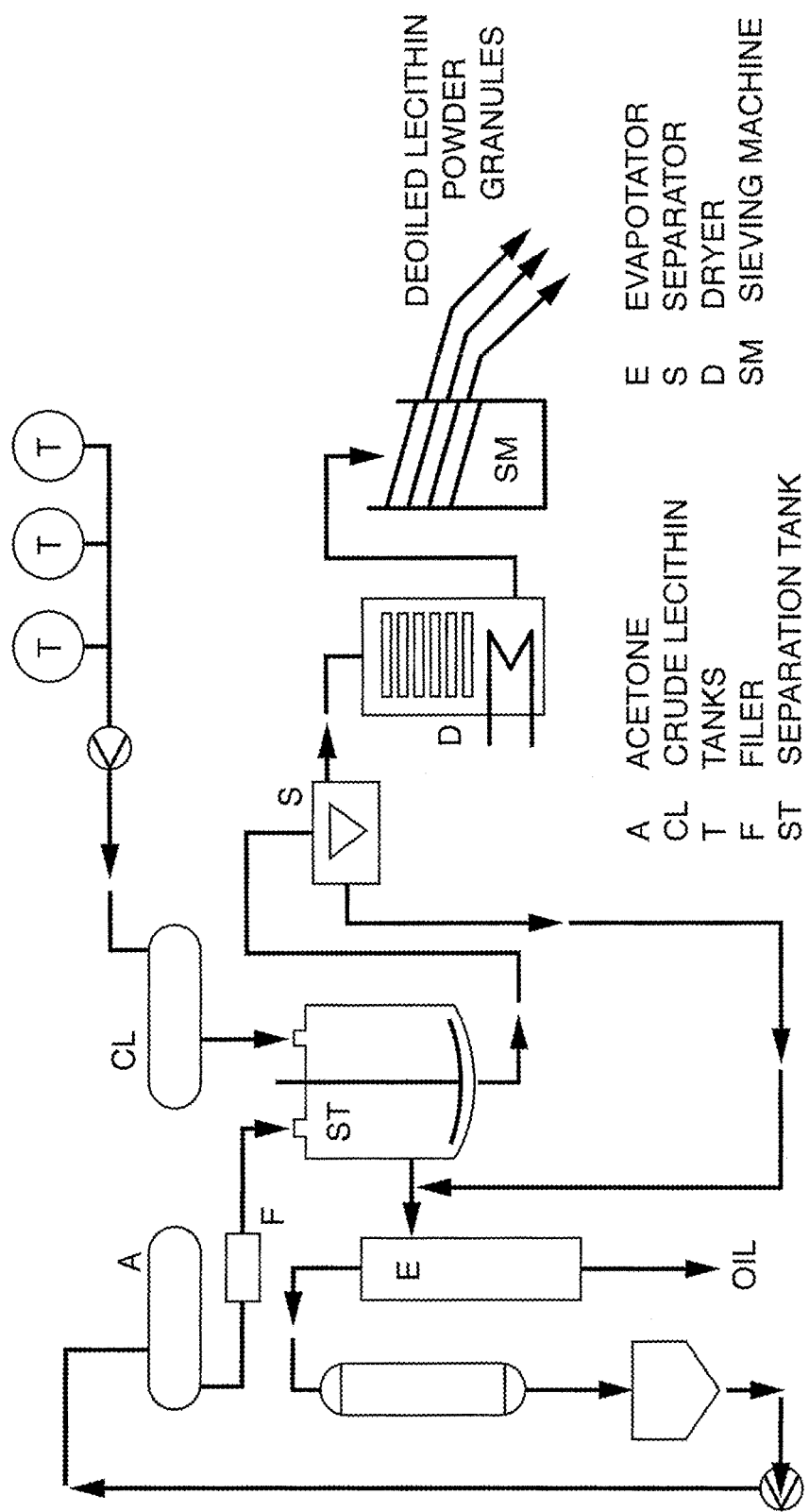
FIG. 7 presents a conventional industrial phospholipid extraction process based upon acetone extraction.

The TAG level in the ethanol soluble lipids was dependent on temperature (T), a squared water content ($W^2$) and a negative interaction between the two variables. See, Table 10. The response surface demonstrates a dominant effect of W within the tested T-range. The solubility of TAG in ethanol is strongly dependent on the water content and temperature. The ethanol azeotrope contains 4.5% by weight of water, close to the centre point in this study. See, Table 7. The use of a 1:3 ratio between krill oil and ethanol gives a TAG concentration of 9.5% in the experimental ethanol phase. This is higher than the solubility of TAG in pure ethanol and a water/ethanol azeotrope within the tested temperature range. See, FIG. 7; and Lusas et. al., "Final report: IPA as an extraction solvent" INFORM 8(3):290-306 (1997). Although it is not necessary to understand the mechanism of an invention, it is believed that a two-phase system may be formed during cool-down of the samples after the initial conditioning at 35° C. and, depending on the temperature, some of the TAGs may crystallize and form a solid phase that can be observed as a sediment after centrifugation of the experimental samples.

A full model could be fitted to the FFA response, including both negative and positive regression coefficients. However, this suggested the use of a slightly higher criteria for the removal of insignificant regressors, where the final model included variables with a significance level up to p=0.058. See, Table 10. This response surface demonstrated a curvature with a dominating effect of temperature. The interaction effect gives a minor effect of water at low compared to high temperature levels. The data suggest that a maximum FFA level can be expected at conditions T=264 K (−9° C.) and 7% water.

The cholesterol response model shows a negative squared effect of both T and W in addition to a positive interaction. The obtained model has a $R^2$=0.77 and includes the $W^2$ regressor with a significance level of 0.096. The response surface shows a clear curvature for water. The net T-effect is approximately linear, mainly caused by a very low $T^2$ coefficient. The interaction effect gives less effect of water at low compared to high temperature level. See, Table 10.

The astaxanthin response model shows no effect of T, and a negative main and positive squared effect of W. See, Table 10. Astxanthin mainly partitions in the apolar TAG phase and the shown astaxanthin response is consistent with the TAG and neutral lipids responses. In contrast, the acetone fractionation carried less astaxanthin over to the polar lipids than the ethanol fractionation. See, Table 8. However, even at the best experimental condition (e.g., ENo 5) an astaxanthin reduction of 49% was observed in the ethanol fractionation.

The neutral lipids response model show a positive effect of T, a negative main and positive squared effect of W, and no interaction. See, Table 10. The resulting response surface is very similar to the TAG response and identifies the neutral lipids as a dominating component.

The dominating polar lipid class (e.g., PC) response model shows a simple behavior with a negative effect of T and a positive interaction. See, Table 10. The data show a response surface having a dominating effect of water, reflecting a reduced solubility of TAG with increasing water content in an ethanol phase. See, FIG. 11. A less satisfactory model was obtained for lyso-PC with a negative effect of W and positive interaction. PE shows a more complex behavior to ethanol fractionation with a positive and negative main and squared T effect, respectively, and a negative squared W effect and positive interaction. The level of lyso-PC in krill oil is very low which increases the analytical uncertainty and also influences the obtainable quality of the fitted model. In general, the total polar lipids response surface is dominated by the PC response wherein the highest level is obtained by combining the lowest T and highest W within the experimental range.

The sodium chloride response model shows a positive main and squared effect of water content in the ethanol phase and a negative interaction effect. See, Table 10. The response surface reflects a dominating effect of water with minor effect of temperature. See, FIG. 11.

The response model for the total yield of ethanol soluble compounds is only dependent on T and W with no interaction. See, Table 10. The model has a very high-explained variance of 97.7%. The response surface reflects the linear effect of the main variables with the highest effect of temperature within the tested experimental range. See, FIG. 11. The highest yield is obtained when combining the highest T and lowest W within the experimental range. However, a higher yield also gives a higher TAG and lower PL content in the final product.

The fatty acid composition was analyzed in the cube points of the experimental design. See, Table 11.

The data disclosed herein show that both the Rimfrost starting material krill oil and acetone insoluble fraction contained high levels of TMA and TMAO. Table 8. TMA has a strong smell characterized as fishy and ammonia, and can be expected to have a significant impact on the sensory characteristics of the product. Both compounds were quantitatively carried over to the acetone insoluble fraction, with a minor increase in the TMA level of the obtained product. TMAO was somewhat reduced, probably through redox reaction with unsaturated compounds during the processing

TABLE 11

Fatty acid composition (g/100 g) in Rimfrost, acetone insoluble and soluble lipids, and ethanol soluble lipids ENo 1-4.

| Fatty add | Acetone fractionation | | | Ethanol fractionation-soluble | | | |
|---|---|---|---|---|---|---|---|
| | Rimfrost | Insoluble | Soluble | ENo1 | ENo2 | ENo3 | ENo4 |
| C14:0 | 5.8 | 1.6 | 8.5 | 2.7 | 1.7 | 4.2 | 2.3 |
| C16:0 | 13.9 | 13.8 | 13.8 | 12.3 | 11.9 | 13.5 | 12.2 |
| C16:1 n-7 | 2.4 | 0.7 | 3.8 | 1.6 | 0.9 | 1.9 | 1.1 |
| C16:2 n-4 | 0.4 | 0.1 | 0.7 | 0.3 | 0.1 | 0.3 | 0.2 |
| C16:3 n-4 | 0.2 | 0.1 | 0.3 | 0.1 | 0.1 | 0.1 | 0.1 |
| C18:0 | 0.8 | 0.5 | 0.8 | 0.5 | 0.4 | 0.6 | 0.5 |
| C18:1 n-9/7/5 | 10.2 | 6.3 | 12.8 | 7.6 | 5.6 | 8.3 | 6.1 |
| C18:2 n-6 | 1.3 | 0.9 | 1.6 | 1.1 | 0.9 | 1.2 | 0.9 |
| C18:3 n-3 | 2.6 | 2.1 | 3.1 | 2.4 | 2.1 | 2.5 | 2.1 |
| C18:3 n-6 | 0.1 | 0.1 | 0.2 | 0.2 | 0.1 | 0.2 | 0.1 |
| C18:4 n-3 | 5.6 | 2.6 | 8 | 4.9 | 3.4 | 5 | 3.5 |
| C20:0 | 0.1 | <0.1 | 0.1 | <0.1 | <0.1 | 0.1 | <0.1 |
| C20:1 n-9/7 | 0.7 | 0.4 | 0.8 | 0.5 | 0.4 | 0.5 | 0.4 |
| C20:2 n-6 | 0.1 | 0.1 | 0.1 | 0.1 | <0.1 | 0.1 | 0.1 |
| C20:3 n-3 | 0.2 | 0.1 | 0.2 | 0.1 | 0.1 | 0.1 | 0.1 |
| C20:3 n-6 | <0.1 | 0.1 | <0.1 | 0.1 | 0.1 | 0.1 | 0.1 |
| C20:4 n-3 | 0.5 | 0.5 | 0.5 | 0.6 | 0.6 | 0.5 | 0.5 |
| C20:4 n-6 | 0.2 | 0.2 | 0.1 | 0.2 | 0.2 | 0.2 | 0.2 |
| C20:5 n-3 | 11.4 | 15.2 | 9.3 | 15.6 | 16.5 | 14.3 | 15.4 |
| C21:5 n-3 | 0.5 | 0.6 | 0.5 | 0.7 | 0.7 | 0.6 | 0.6 |
| C22:0 | <0.1 | <0.1 | <0.1 | <0.1 | <0.1 | <0.1 | <0.1 |
| C22:1 n-11/9/7 | 0.3 | 0.4 | 0.2 | 0.3 | 0.3 | 0.3 | 0.3 |
| C22:4 n-6 | <0.1 | <0.1 | <0.1 | <0.1 | <0.1 | <0.1 | <0.1 |
| C22:5 n-3 | 0.3 | 0.4 | 0.3 | 0.4 | 0.4 | 0.3 | 0.3 |
| C22:6 n-3 | 6.8 | 9.3 | 4.9 | 8.7 | 8.9 | 8.1 | 8.7 |
| C24:1 n-9 | <0.1 | 0.1 | <0.1 | <0.1 | <0.1 | <0.1 | <0.1 |
| Sum saturated | 20.5 | 15.9 | 23.2 | 15.5 | 14 | 18.4 | 15 |
| Sum monoenoic | 13.6 | 7.9 | 17.6 | 10 | 7.2 | 11 | 7.9 |
| Sum PUFA | 30.1 | 32.4 | 29.8 | 35.5 | 34.2 | 33.6 | 32.9 |
| Sum n-3 PUFA | 27.8 | 30.8 | 26.8 | 33.4 | 32.7 | 31.4 | 31.2 |
| Sum n-5 PUFA | 1.7 | 1.4 | 2.0 | 1.7 | 1.3 | 18 | 1.4 |
| Sum identified fatty acids | 64.2 | 56.2 | 70.6 | 61 | 55.4 | 63 | 55.8 |

The level of n-3 PUFAs in Rimfrost krill oil was increased after ethanol fractionation (ENo 1) from 27.8 to 33.4% (e.g., W=1.5% and T=−20° C.). See, Table 7. This corresponds to an improvement of 20.1%. Increasing the ethanol/water content to 8.5% (e.g., Eno 2) decreased PUFA levels level to 32.7%. Increasing the temperature to 0° C. further reduced PUFA levels to 31.4% and 31.2% at water contents of 1.5% and 8.5%, respectively. In contrast, acetone fractionation gave a level of polar lipids in the acetone insoluble fraction of 72%; slightly higher than the upper level obtained experimentally by ethanol fractionation (70.8% in ENo 2). However, this higher acetone extraction yield was not reflected by the obtained level of n-3 PUFA (30.8%). See, Table 11. Ethanol fractionation provided a higher level of n-3 PUFAs at all tested experimental conditions as compared to acetone fractionation. For example, acetone fractionation gave a level of soluble fraction n-3 PUFAs of 26.8%. The acetone soluble lipid composition was dominated by TAG and the results indicates a high level of PUFA in this lipid fraction.

steps. The level of TMA in the ethanol soluble fraction showed a comparable level to acetone insolubles. Cf, Table 8 and Table 12.

TABLE 12

Levels (mg N/100 g) of trimethylamine (TMA) and trimethylamine N-oxide (TMAO) in ethanol soluble lipids from cube design treatments.

| | TMA-N | TMAO-N |
|---|---|---|
| 1 | 42 | 105 |
| 2 | 78 | 142 |
| 3 | 45 | 91 |
| 4 | 58 | 130 |

It was also noted that the TMA/TMAO levels correlated to the water content in the ethanol phase. FIG. 9. The level of TMAO was increased compared to the krill oil level and is highly correlated to the TMA level ($R^2$=0.817).

After centrifugation of the ethanol fractionated samples a solid, and easy to decant, sediment was obtained at the three lowest temperature levels. At 0 and 4.1° C. a softer sediment was formed, where a separation funnel was used to control the separation of the two phases. The solid structure and analyses of the composition of the sediment confirmed the separation and crystallization of TAGs in the ethanol insoluble phase. Table 13. Some higher FFA and lower cholesterol concentration could also be observed.

From a practical perspective an easy to separate solid to soft sediment was formed based on the used fractionation conditions. The solid structure and analyses of the composition of the sediment confirmed the separation and crystallization of TAGs in the ethanol insoluble phase. The polar lipid levels were <1% when using a 1.5% water content with astaxanthin levels of approximately 559 mg/kg. In one embodiment, the present invention contemplates a method

TABLE 13

Composition (w/w %), yield (% of starting material) and astaxanthin (mg/kg) in the sediment after ethanol fractionation.

| ENo | FFA | Chol | Chol-ester | TAG | DAG | MAG | Neutral | PE | PI | PS | PC | Lyso-PC | Polar | NaCl | Yield | Asta |
|---|---|---|---|---|---|---|---|---|---|---|---|---|---|---|---|---|
| 1 | 5.1 | 2.1 | <0.5 | 75 | 3.5 | <1 | 86.3 | 0.7 | <1 | <1 | <1 | <0.5 | 0.7 | — | 38.9 | 454 |
| 2 | 4.1 | 2.2 | <0.5 | 65 | 1.1 | <1 | 72.5 | 1.8 | <1 | <1 | 15 | <0.5 | 17 | — | 59 0 | 356 |
| 3 | 4.9 | 0.7 | <0.5 | 75 | 2.1 | <1 | 83.0 | 0.9 | <1 | <1 | <1 | <0.5 | 0.9 | — | 30.1 | 559 |
| 4 | 5.6 | 0.8 | <0.5 | 77 | 1.0 | <1 | 84.4 | 2.0 | <1 | <1 | 5.5 | <0.5 | 7.5 | — | 48.0 | 430 |

The polar lipids levels was <1% when using a 1.5% water content. (e.g., ENo 1 and ENo 3). Use of 8.5% water significantly increased the polar lipid level. (e.g., ENo 2 and ENo 4). The astaxanthin level was generally much higher than observed in the ethanol soluble lipids with a maximum level of 559 mg/kg as compared to 222 mg/kg in the krill oil. Cf. Table 13: ENo3 and Table 7. The tested processing conditions can thereby optionally be applied to concentrate astaxanthin esters from the krill oil.

Figure 11A:
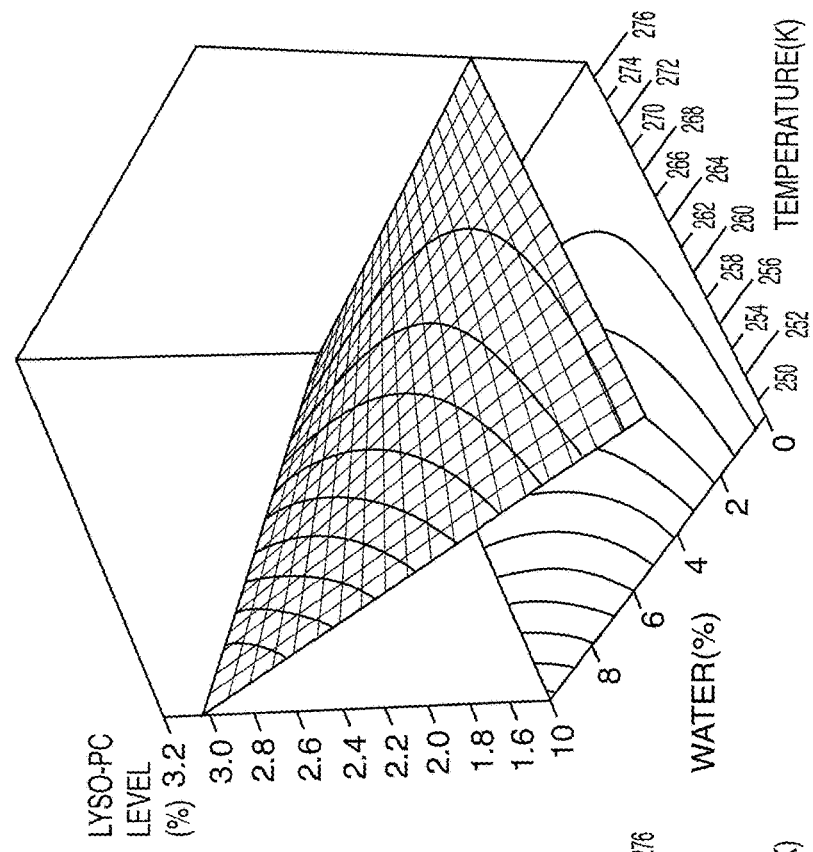
Figure 11B:
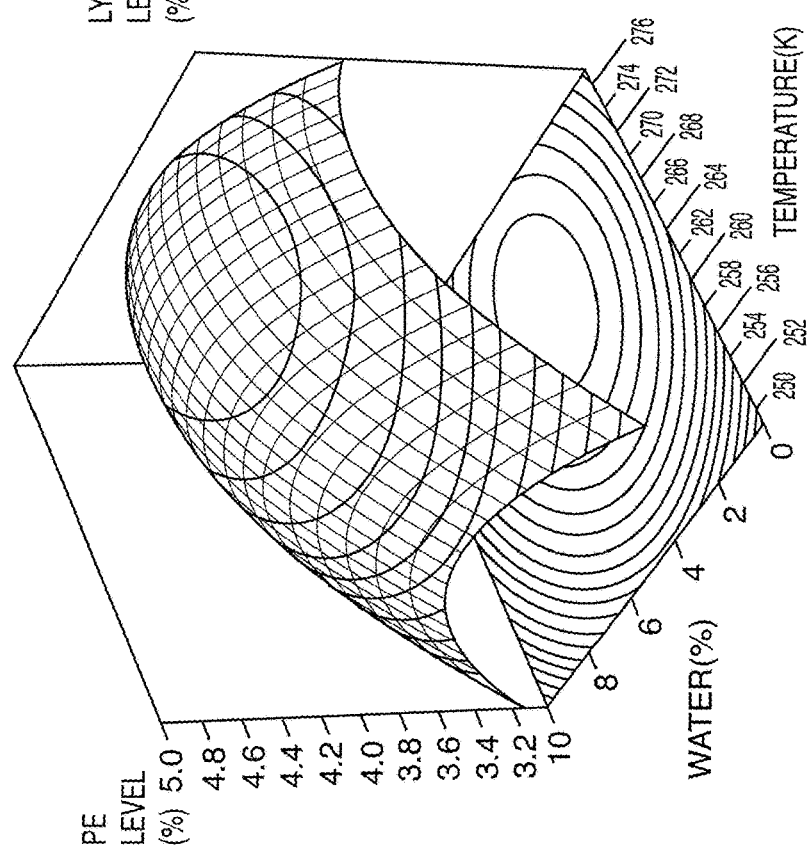

In one embodiment, the present invention contemplates a method for concentrating a combination of polar lipids (e.g., for example, PE+PC+lyso-PC) to above 60%. In one embodiment, the method comprises ethanol fractionation of a krill extract (e.g., for example, a krill oil). Although it is not necessary to understand the mechanism of an invention, it is believed that the presently disclosed method can easily be integrated in a downstream process for removal of ethanol after extraction of lipids from krill meal. In one embodiment, the method comprises an ethanol extraction mixture ranging between 90%:10% ethanol/water and 100%:0% ethanol/water. In one embodiment, the method comprises a 94%:6% ethanol/water mixture. In one embodiment, the method is performed at a temperature ranging between approximately 277.3° K. (4.1° C.) and 249° K. (−24.1° C.). In one embodiment, the method produces a concentrated phospholipid krill oil ranging between approximately 60-73% polar lipids. FIG. 11.

Figure 5:
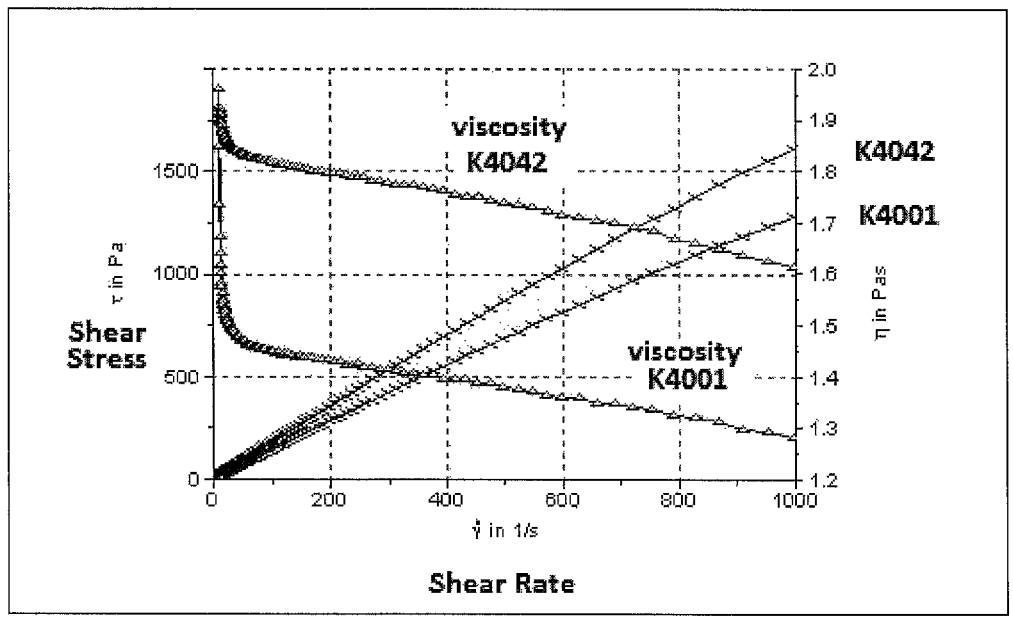
FIG. 5 presents exemplary data measuring shear stress and shear rate of krill oil incubated at 40° C.

Overall, the data suggest that ethanol fractionation results in a product yield that is positively correlated to temperature and negatively to water content. In some embodiments, ethanol fractionation provides a krill oil having a polar lipid content of >60% polar lipid content (e.g., 66.0% and 64.1%). FIG. 5. In comparison, a level of 72% polar lipids could be obtained based on acetone fractionation of the krill oil.

The data also show that astaxanthin content is strongly negatively correlated to water content and the highest carry over of astaxanthin from the starting krill oil material to the ethanol fractionated concentrated polar lipid krill oil is obtained when using pure ethanol (e.g., ~114 mg/kg). A 100% ethanol extraction also resulted in a concentrated polar krill oil having the lowest level of unwanted compounds (e.g., for example, NaCl, cholesterol, TMAO and TMA). Best retention of n-3 PUFA is obtained at low temperature and water content.

comprising ethanol fractionation of krill oil that creates a composition comprises concentrated astaxanthin esters.

Although it is not necessary to understand that mechanism of an invention, it is believed that the water content in the ethanol phase has a strong impact on the composition and yield of polar lipids. In a processing plant, the polar lipid yield depends on the water content of the used ethanol and the moisture content in the krill meal. The need to control these parameters depends on the target level of polar lipids after ethanol fractionation.

VII. Non-Supercritical Carbon Dioxide Krill Oil Extraction

Figure 16:
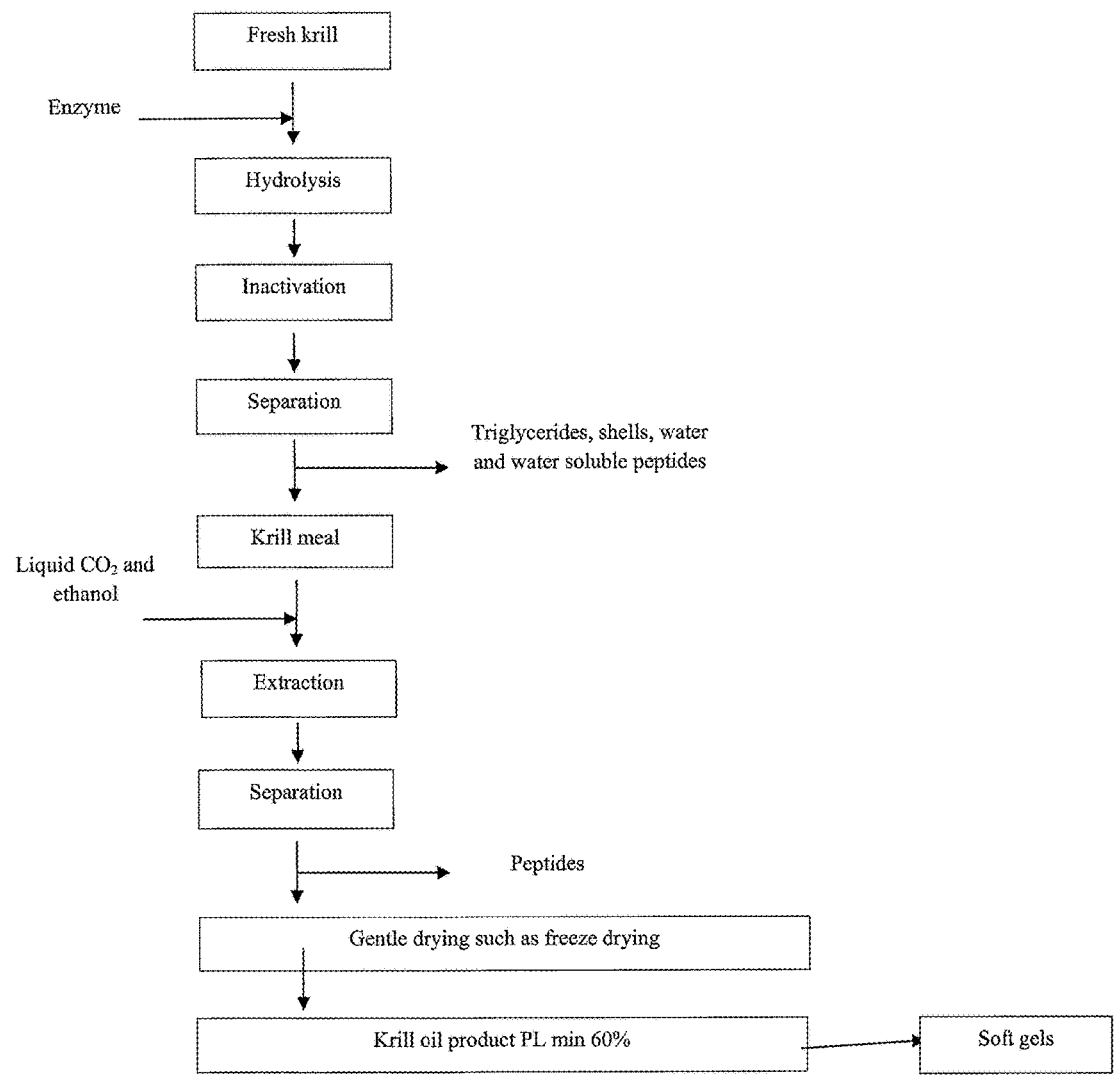
FIG. 16 presents an embodiment of a two stage process where the manufacture of krill meal is performed on board the krill fishing ship and the extraction is performed in an extraction plant on shore.

In one embodiment, a krill lipid extract is obtained by extraction process of dried meal derived from the marine crustacean *Euphausia superba* (Antarctic Krill) with sub-critical liquid $CO_2$ and ethanol extraction (two steps). It is a two stage process where the manufacture of krill meal is performed on board the krill fishing ship and the extraction is performed in an extraction plant on shore. The manufacturing process is presented in FIG. 16.

1) The manufacturing process of the krill oil starts on board a ship. Antarctic krill is immediately (maximally 20 minutes after catch) shredded through a knife cutter into pieces of a particle size of 3-6 min at a temperature of 1-2° C.
2) Fresh water and proteolytic enzymes are added and heated to a temperature of 55-60° C. The reaction is allowed to run for 45 minutes.
3) The material is then transferred to a decanter separating the fluorine-containing fine particles and the liquid proteinaceous fraction.
4) The material is then heated to a temperature of 93° C. in order to deactivate the enzymatic activity.
5) The liquid proteinaceous fraction is then transferred to a separation step by a specially designed decanter, separating the solid phase containing insoluble proteins and polar lipids concentrate (PPC) from the hydrolysate,
6) The PPC is then dried in a thin film vacuum drier and packed in air tight bags under nitrogen atmosphere.
7) The aqueous soluble protein (hydrolysate) and neutral lipid phase are feed to a separator separating the neutral lipid phase from the hydrolysate.
8) The oil is stored in air tight containers under nitrogen atmosphere.

9) The hydrolysate are continuously feed into a flash evaporator for dewatering/concentration giving a concentrated hydrolysate fraction (CHF) with dry weight of 55-70% and stored in air tight containers under nitrogen atmosphere.

10) The lipids and proteins are separated and extracted from the hydrolysate via the addition of ethanol and sub-critical liquid $CO_2$. The hydrolysate and 100% ethanol are loaded into extractors and kept there under elevated temperature and pressure until extraction rate is reached and process completed (approximately 12 hours).

11) Proteins and krill material are removed from the lipid extract by precipitation and filtration.

12) The ethanol and residual water are removed by subsequent gentle drying evaporation steps (e.g., lyophilization).

The lipid extract is then loaded into drums and stored at room temperature.

Use of controlled enzymatic hydrolysis step in production of krill meal allows separation of fluorine containing exoskeleton and thus, the reduction of the fluorine content of krill lipid extract.

Figure 12:
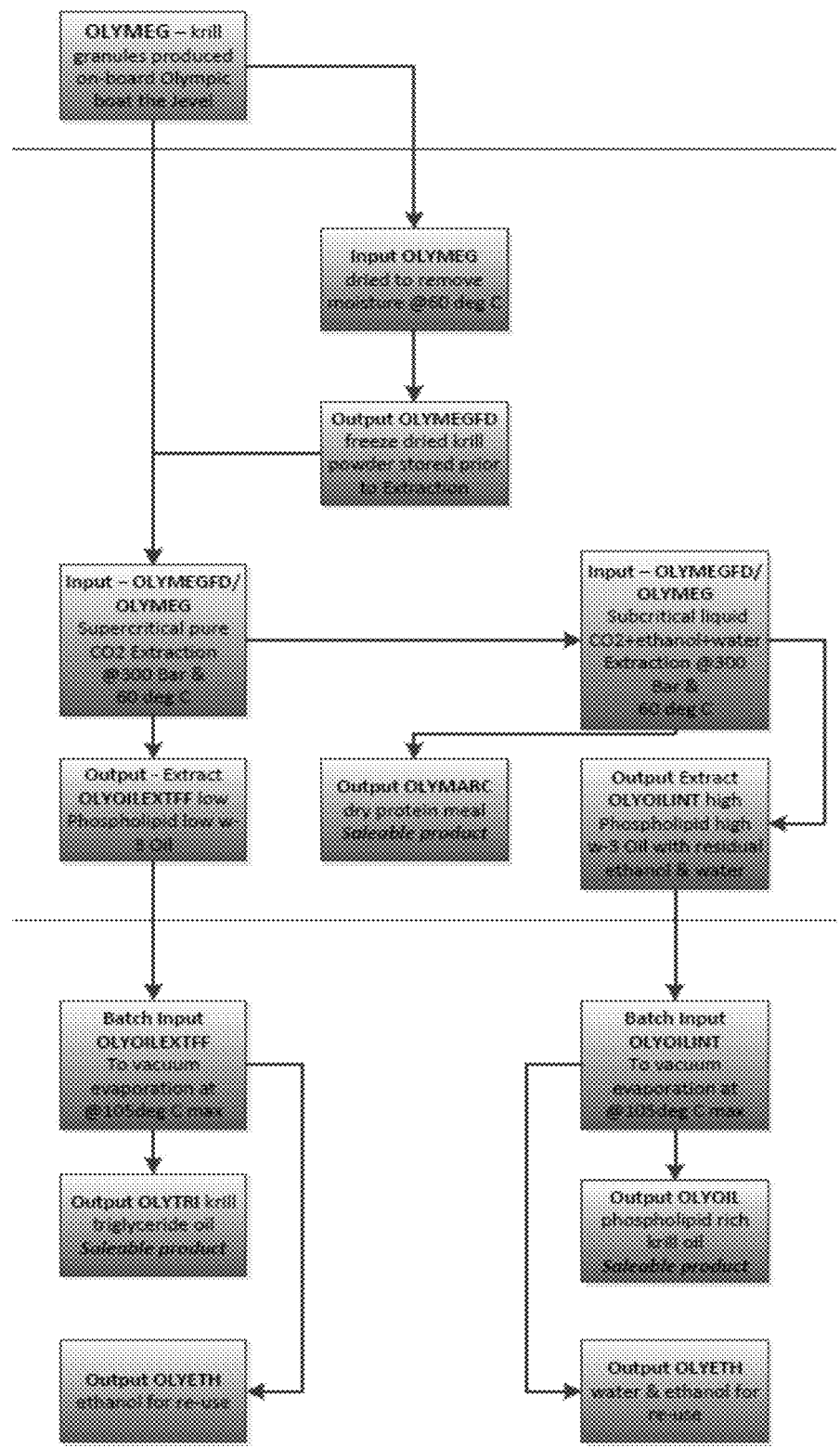
FIG. 12 presents one embodiment of a krill oil production workflow to produce various embodiments of the present invention.

In one embodiment, the present invention contemplates a method for producing krill oil comprising extracting a krill meal with a solvent comprising subcritical carbon dioxide, ethanol and water to produce a concentrated phospholipid krill oil (e.g., OLYOIL) that was subsequently subjected to lyophilization. Table 14. In one embodiment, the method further comprises extracting the krill meal with a solvent comprising supercritical carbon dioxide. See, FIG. 12.

TABLE 14

Lyophilized Krill Oil Extracted With A Subcritical Carbon Dioxide Solvent

| | |
|---|---|
| Astaxanthin | 12-13 mg/100 gm |
| Esterified Astaxanthin | 234 mg/1000 gm |
| Ethanol | 0.3 ml/100 gm |
| Total Fatty Acids[a] | 68.7-72.1% |
| Flash Point, PMCC | 112-118° C. |
| Specific Gravity @ 15/15° C. | 1.0011-1.0118 |
| Total Microbiology | <10 cfu/g |
| Moisture @ 70° C. | 3 g/100 g |
| Peroxide | <0.1 Meq $O_2$/1000 g fat |
| Eicosapentaenoic Acid 20:5 (EPA) | 15.5% (w/w) relative to total triglycerides |
| Docosahexaenoic Acid 22:6 (DHA) | 9.4% (w/w) relative to total triglycerides |
| Total Omega 3 Fatty Acids | 29.5% (w/w) relative to total triglycerides |
| Eicosapentaenoic Acid 20:5 (EPA) | 21.8% (w/w) relative to total fatty acids |
| Docosahexaenoic Acid 22:6 (DHA) | 13.2% (w/w) relative to total fatty acids |
| Total Omega 3 Fatty Acids | 41.5% (w/w) relative to total fatty acids |
| Total Phospholipids[b] | 60 g/100 g |
| TMA | 31-39 mg/100 g |
| TMAO | 618-661 mg/100 g |
| Viscosity @ 35° C. | 1,700,000 Centiposie |

[a]Individual fatty acid composition. FIG. 13
[b]Individual phospholipid composition. FIG. 14.

Figure 15:
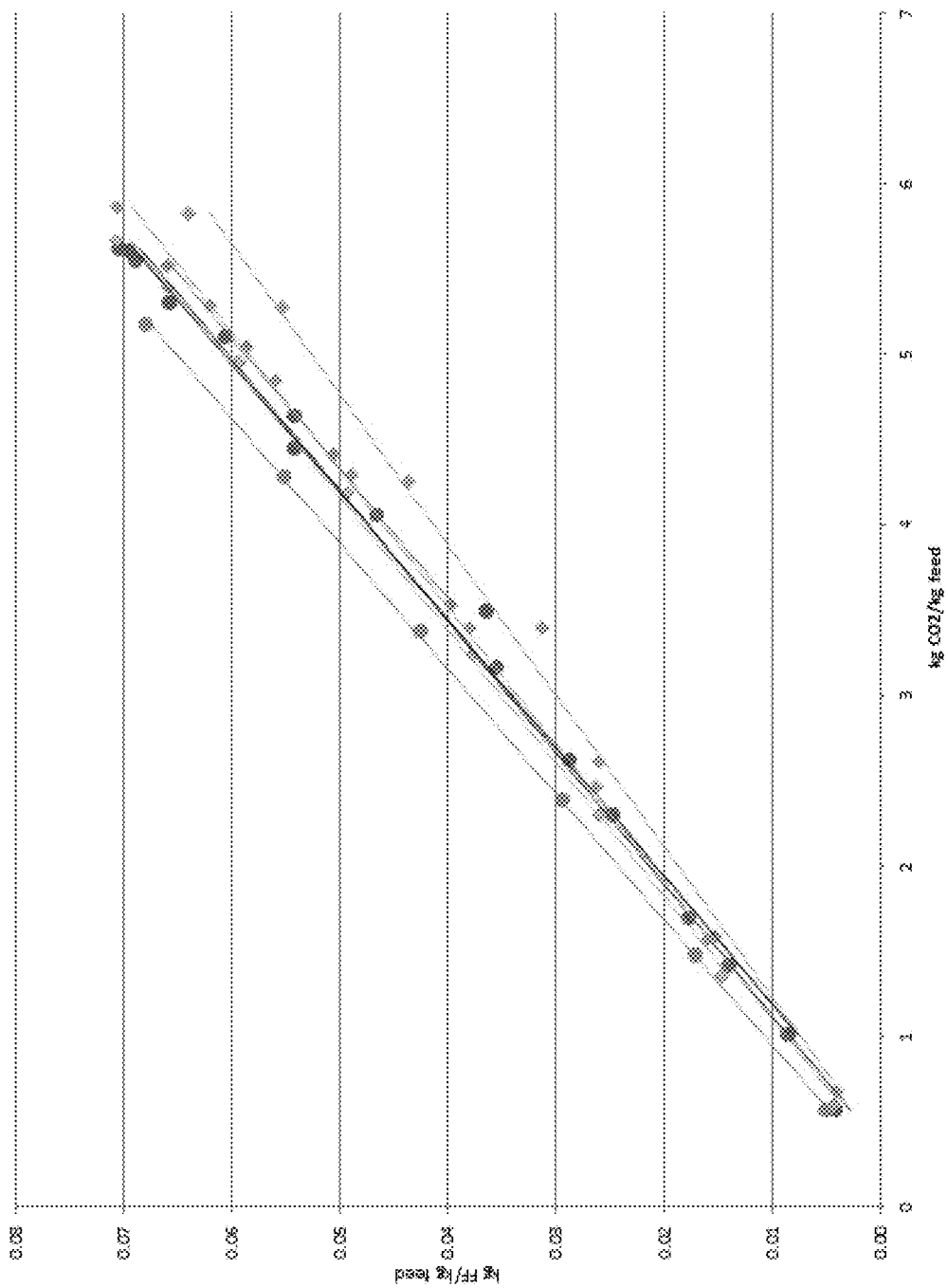
FIG. 15 presents exemplary data showing a comparison of a subcritical liquid $CO_2$ solvent to a supercritical $CO_2$ solvent monitoring triglyceride (TG) extraction. Circles: Supercritical TG extraction batches. Diamonds: Subcritical liquid TG extractions. It can be seen that very little difference in solubility is present between the two solvents.

Several runs comparing triglyceride (TG) removal using subcritical liquid $CO_2$ to supercritical $CO_2$ were performed by plotting the production of $CO_2$ versus the production of free fatty acids (FF). FIG. 15. As can be seen from the graph, the solubility between these two extraction conditions was very similar. Analysis of the TG oil samples indicated that omega 3 fatty acid loss is insignificant with subcritical CO2 extraction, and intersample variation was observed to be between 5-10%. In one embodiment, the present invention contemplates a method comprising, providing a subcritical $CO_2$, ethanol and water solvent and extracting a high phospholipid krill oil with said solvent.

VI. Nutritional and Health Consequences of Aging

Nutritional needs are known to change as animals (e.g., mammals, such as humans) age. Reasons for these changes include, but are not limited to, decreased absorption of essential nutrients from diet, a more sedentary lifestyle, a decreased appetite and/or a change in metabolism. These nutritional changes occur in both the healthy elderly population and the elderly with exceptional nutritional needs due to health problems or diseases. There is growing scientific documentation that shows that certain essential macro and micro nutrients can prevent the development of certain diseases in the elderly population.

There has surprisingly been found that high phospholipid/low viscosity krill oil compositions are effective in alleviation, prevention or treatment certain diseases in the elderly population or in groups of particular nutritional needs. It has also been surprisingly found that high phospholipid/low viscosity krill oil compositions enhance the absorption of some essential minerals and lipid soluble health ingredients and that these krill compositions are effective in prevention and treatment of health conditions related to aging.

In one embodiment, the present invention contemplates a use of a nutritional supplement composition by administering the composition ranging between approximately 0.005-0.50 g krill meal per day per kg of body weight of an animal for the treatment of a degenerative joint disease. In one embodiment, the composition is homogenous. In one embodiment, the composition further comprises at least one omega-3 fatty acid. In one embodiment, the composition is stable. In one embodiment, the homogeneity of the composition is characterized by a lack of phase separation.

A. Homeostatic Control

Aging may be characterized by an inability of tissues to maintain homeostasis. This leads to an impaired response to stress and, as a consequence, an increased risk of morbidity and mortality. The incidence of numerous debilitating chronic diseases, such as cardiovascular disease, neurodegeneration, diabetes, arthritis, and osteoporosis, increases almost exponentially with age. Aging is thought to be driven, at least in part, by the accumulation of stochastic damage in cells. This includes damage to proteins, DNA, mitochondria, and telomeres, which is driven by reactive oxygen species. Mitochondria are the major producers of reactive oxygen species, which damage DNA, proteins, and lipids if not rapidly quenched. Alterations in mitochondria have been noted in aging, including decreased total volume, increased oxidative damage, and reduced oxidative capacity. These biochemical and bioenergetic changes are accompanied by perturbations in cellular dynamics, such as a decrease in mitochondrial biogenesis and an increase in mitochondrially mediated apoptosis. Peterson et al, *Journal of Aging Research*, Epub Jul. 19, 2012.

A lack of homeostasis control can lead to an impaired response to stress and, as a consequence, an increased risk of morbidity and mortality. For example, reports suggest that the incidence of numerous debilitating chronic diseases, such as cardiovascular disease, neurodegeneration, diabetes, arthritis, and osteoporosis, increases almost exponentially with age. Tilstra et al., *The Journal of Clinical Investigation* 122(7):2601-2612 (2012). Aging is associated with progressive loss of neuromuscular function that often leads to progressive disability and loss of independence. The term sarcopeniais now commonly used to describe the loss of skeletal muscle mass and strength that occurs in concert with biological aging. The prevalence of sarcopenia, which may be as high as 30% for those over 60 years, will increase as the percentage of the very old continues to grow in our populations. The link between sarcopenia and disability among elderly men and women highlights the need for continued research into the development of the most effective interventions to prevent or at least partially reverse sarcopenia. The aging process is also believed to be a factor in the age-dependent occurrence of central nervous system disabilities, such as dementia.

The ability of a cell to resist oxidant damage during homeostatic imbalance is determined by a balance between the generation of reactive oxygen species and the defensive capacity to produce antioxidants. Glutathione (γ-glutamylcysteinylglycine) is the most abundant endogenous intracellular antioxidant present in millimolar quantities within cells. Glutathione plays a central role in antioxidant defenses, and irreversible cell damage supervenes when the cell is unable to maintain intracellular glutathione concentrations. Evidence from several animal and human studies suggests that concentrations of glutathione decline with aging. It has been shown that dietary supplementation with the glutathione precursors cysteine and glycine fully restores glutathione synthesis and concentrations and lowers levels of oxidative stress and oxidant damages in elderly persons. Rajagopal et al, *Am J Clin Nutr* 94:847-853 (2011). Other naturally occurring bioactive compounds, such as pyrroloquinoline quinone (PQQ), resveratrol, genistein, hydroxytyrosol, and quercetin have also been reported to improve mitochondrial respiratory control or stimulate mitochondrial biogenesis.

Cell permeable peptide antioxidants have been reported that are very potent at reducing intracellular ROS and preventing cell death. The peptides are tetrapeptides with alternating aromatic residues and basic amino acids. Zhao et al, *The Journal of Biological Chemistry* 279, 34682 (2004).

As many of the components in high phospholipid/low viscosity krill oil compositions might work as antioxidants and/or affect the antioxidative/inflammatory defense in the cell it would be interesting to test the high phospholipid/low viscosity krill oil compositions in biological systems that can measure the antioxidative effect and the anti-inflammatory effect in vitro to identify the most interesting composition. The compositions should also be tested in bioavailability studies to identify if the compounds of interest will be absorbed.

B. Age-Related Macular Degeneration

Age-related macular degeneration (AMD) is also a major cause of disability in the elderly. More than 20 million people worldwide are severely affected either by age-related macular degeneration or cataracts. AMD is the leading cause of blindness in people over 55 years of age in the western world. Nearly 30% of Americans over the age of 75 years have early signs of AMD and 7% have late stage disease. There are currently no effective treatment strategies for most patients with AMD, attention has focused on efforts to stop the progression of the disease or to prevent the damage leading to AMD.

C. Diabetes

Type 2 diabetes is the most common chronic metabolic disease in the elderly, affecting ~30 million individuals 65 years of age or older in developed countries. The estimated economic burden of diabetes in the United States is ~$100 billion per year, of which a substantial proportion can be attributed to persons with type 2 diabetes in the elderly age group. Epidemiological studies have shown that the transition from the normal state to overt type 2 diabetes in aging is typically characterized by a deterioration in glucose tolerance that results from impaired insulin-stimulated glucose metabolism in skeletal muscle. Petersen et al, *Science* 300(5622):1140-1142 (2003).

D. Inflammation

Recent scientific studies have advanced the notion of chronic inflammation as a major risk factor underlying aging and age-related diseases. Low-grade, unresolved, molecular inflammation is described as an underlying mechanism of aging and age-related diseases, which may serve as a bridge between normal aging and age-related pathological processes.

Elevated oxidative stress has been linked to chronic inflammation and several aging related illnesses. The ability of a cell to resist oxidant damage is determined by a balance between the generation of reactive oxygen species and the defensive capacity to produce antioxidants. A central problem associated with the assessment of free radical induced oxidative stress in disease development has been the limitation in existing assay methods for in vivo measurement of free radical generation. For example, F2-isoprostanes, structural isomers of PGF2α, are formed during free-radical catalysed peroxidation of arachidonic acid. A major F2-isoprostane, 8-iso-PGF2α, is now a well-recognised reliable indicator of oxidative stress in vivo. Basu S., *Antioxid. Redox Signal.* 10:1405-1434 (2008).

The transcription factor NF-κβ is a component of the cellular response to damage, stress, and inflammation. Numerous studies report increased NF-kB activity with aging, and NF-kB was identified as the transcription factor most associated with mammalian aging based on patterns of gene expression. Adam et al, *Genes and Development* 3244 (2007). Chronic activation of NF-κB is observed in numerous age-related diseases including, but not limited to, muscle atrophy, multiplesclerosis, atherosclerosis, heart disease, both type 1 and 2 diabetes, osteoarthritis, dementia, osteoporosis, and cancer. Tilstra et al, *The Journal of Clinical Investigation* 122(7):2601-2612 (2012). NF-κB DNA binding is increased in skin, liver, kidney, cerebellum, cardiac muscle, and gastric mucosa of old rodents compared with that in young rodents. In addition, NF-κB was identified as the transcription factor most associated with mammalian aging, based on patterns of gene expression. Furthermore, chronic activation of NF-κB is observed in numerous age-related diseases, including muscle atrophy, multiple sclerosis, atherosclerosis, heart disease, both type 1 and 2 diabetes, osteoarthritis, dementia, osteoporosis, and cancer.

Several scientific publications strongly suggest that inhibitors of the IKK/NF-κB pathway may delay damage and extend health span in patients with accelerated aging and chronic degenerative diseases of old age.

Based on literature in the area of age related diseases, it is apparent that oxidative damage and low grade inflammation are central in the development of many of the age related diseases. The transcription factor NF-κB is a central component for the cellular response to these triggers. A scientific approach to the development of nutritional supplements and drugs for the aging population could be to focus on the development of effective antioxidants to target these central biological mechanisms.

VII. Treatment of Medical Disorders with Krill Oil

A. Central Nervous System Medical Disorders

In one embodiment, the medical disorder comprises a central nervous system disorder. In one embodiment, the central nervous system disorder comprises a mental disorder. In one embodiment, the mental disorder includes, but is not limited to infancy, childhood or adolescence disorders, cognitive disorders, substance-related disorders, psychotic disorders including but not limited to schizophrenia, mood disorders including but not limited to depression, anxiety disorders, somatoform disorders, factitious disorder, dissociative disorders, sexual disorders, eating disorders, sleep disorders, impulse-control disorders, adjustment disorders or personality disorders.

The central nervous system is particularly vulnerable to oxidative insult on account of the high rate of $O_2$ utilization, the relatively poor concentrations of classical antioxidants and related enzymes, and the high content of polyunsaturated lipids, the biomacromolecules most susceptible to oxidation. In addition, there are regionally high concentrations of redox-active transition metals capable of the catalytic generation of ROS. Thus, it is not surprising that oxidative stress is a common discussion point for neurodegenerative disease, where damage to neurons can reflect both an increase in oxidative processes and a decrease in antioxidant defenses.

Accumulating data indicate that oxidative stress (OS) plays a major role in the pathogenesis of multiple sclerosis (MS). Reactive oxygen species (ROS), leading to OS, generated in excess primarily by macrophages, have been implicated as mediators of demyelization and axonal damage in MS. ROS cause damage to main cellular components such as lipids, proteins and nucleic acids (e.g., RNA, DNA), resulting in cell death by necrosis or apoptosis. In addition, weakened cellular antioxidant defense systems in the central nervous system (CNS) in MS, and its vulnerability to ROS effects may augmented damage. Thus, treatment with antioxidants might theoretically prevent propagation of tissue damage and improve both survival and neurological outcome. Miller et al, *Pol Merkur Lekarski.* 27(162):499-502 (2009).

B. Ocular Medical Disorders

The use of herbal medicines and nutritional supplements in ocular disorders including, but not limited to, age-related macular degeneration (AMD), cataracts, diabetic retinopathy and glaucoma, has recently been reviewed. Antioxidants and zinc have been used in patients with certain forms of intermediate and advanced AMD. However, there has been growing evidence regarding potential significant adverse effects associated with the AREDS (Age-Related Eye Disease Study) formula vitamins. However, whether the use of antioxidants or herbal medications in the prevention or treatment of cataracts, glaucoma or diabetic retinopathy would be beneficial is inconclusive. It was recommended that further study of nutritional supplements and herbal medicines in the treatment of eye disease is needed to determine their safety and efficacy. Wilkinson et al., "Use of herbal medicines and nutritional supplements in ocular disorders: an evidence-based review" *Drugs* 71(18):2421-2434 (2011).

Some nutritional remedies have been tried for cataracts, glaucoma, and retinal diseases (macular degeneration, diabetic retinopathy, retinopathy of the newborn, and retinitis pigmentosa). Specifically, some nutritional treatments were given for asthenopia, blepharitis, chalazion, conjunctivitis (including giant papillary conjunctivitis), gyrate atrophy of the choroid and retina, keratoconus, myopia, sicca syndrome (dry eyes), and uveitis. The data suggest that nutritional supplements may play role the further of clinical therapy strategies to ocular disorders. Gaby A R., "Nutritional therapies for ocular disorders: Part Three" *Altern Med Rev.* 13(3):191-204 (2008).

C. Digestive Disorders

Functional digestive disorders can be characterized by symptoms related to the digestive tract for which no pathological causes can be found using routine diagnostic techniques. Recently, several methods have been developed to the study digestive function allow relation between in humans functional alterations, mainly motor and sensory and to be related to functional digestive symptoms. As a result of these advances, both motor and sensory alterations have been identified in subgroups of patients with functional digestive disorders. This knowledge should enable current symptom-based classifications of these disorders to be replaced with new classifications based on specific physiopathologic mechanisms. This would allow more effective therapies aimed at the specific mechanism causing the symptoms to be developed. Serra J., "Clinical research techniques in functional digestive disorders" *Gastroenterol Hepatol.* 29(4):255-62 (2006).

Functional dyspepsia and the irritable bowel syndrome (IBS) are amongst the most widely recognised functional gastrointestinal disorders. Symptom based diagnostic criteria have been developed and refined for the syndromes (the Rome criteria) and these are now widely applied in clinical research. Both functional dyspepsia and IBS are remarkably prevalent in the general population, affecting approximately 20% and 10% of persons, respectively. The prevalence is stable from year to year because the onset of these disorders is balanced by their disappearance in the population. Clinically useful predictors of the course of these disorders have not been identified. Approximately one third of persons with functional dyspepsia concurrently have IBS. In most studies from Western countries, it has been shown that only a minority with functional dyspepsia and IBS present for medical care; the factors that explain consultation behavior remain inadequately defined although fear of serious disease and psychological distress may be important. The majority of patients diagnosed as having functional dyspepsia or IBS continue to have symptoms long term with a significant impact on quality of life. The indirect costs of the functional gastrointestinal disorders greatly outweigh the direct costs but overall these conditions are responsible for a major proportion of health care consumption. Rational management of the functional gastrointestinal disorders will only follow a better understanding of the natural history of these conditions. Talley N. J., "Scope of the problem of functional digestive disorders" *Eur J Surg Suppl.* 582:35-41(1998).

D. Skeletal Disorders

Bone turnover, in which cells of the osteoclast lineage resorb bone and cells of the osteoblast lineage deposit bone, normally occurs in a highly regulated manner throughout life. Perturbations to these processes underlie skeletal disorders, such as osteoporosis, which are common, chronic and disabling, and increase with age. On the basis of empirical observations or on understanding of the endocrinology of the skeleton, excellent bone-resorption inhibitors, but few anabolic agents, have been developed as therapeutics for skeletal disorders. Goltzman D, "Discoveries, drugs and skeletal disorders" *Nat Rev Drug Discov.* 1(10):784-796 (2002). In some embodiment, the present invention contemplates that crustacean meal compositions and other ingredients are useful in treating these disorders.

Notch signaling mediates cell-to-cell interactions that may be involved in embryonic development and tissue renewal. In the canonical signaling pathway, the Notch receptor may be cleaved following ligand binding, resulting in the release and nuclear translocation of the Notch intracellular domain (NICD). NICD induces gene expression by forming a ternary complex with the DNA binding protein CBF1/Rbp-Jk, Suppressor of Hairless, Lag1, and Mastermind-Like (Mam1). Hairy Enhancer of Split (Hes) and Hes related with YRPW motif (Hey) are also Notch targets. Notch canonical signaling plays a central role in skeletal development and bone remodeling by suppressing the differentiation of skeletal cells. The skeletal phenotype of mice misexpressing Hes1 phenocopies partially the effects of Notch misexpression, suggesting that Hey proteins mediate most of the skeletal effects of Notch. Dysregulation of Notch signaling is associated with diseases affecting human skeletal development, such as Alagille syndrome, brachydactyly and spondylocostal dysostosis. Somatic mutations in Notch receptors and ligands are found in tumors of the skeletal system. Overexpression of NOTCH1 is associated with osteosarcoma, and overexpression of NOTCH3 or JAG-GED1 in breast cancer cells favors the formation of osteolytic bone metastasis. Activating mutations in NOTCH2 cause Hajdu-Cheney syndrome, which is characterized by skeletal defects and fractures, and JAG1 polymorphisms, are associated with variations in bone mineral density. In conclusion, Notch is a regulator of skeletal development and bone remodeling, and abnormal Notch signaling is associated with developmental and postnatal skeletal disorders. Zanotti et al., "Notch regulation of bone development and remodeling and related skeletal disorders" *Calcif Tissue Int.* 90(2):69-75 (2012).

Genetic disorders involving the skeletal system may arise through disturbances in the complex processes of skeletal development, growth and homeostasis and remain a diagnostic challenge because of their variety. The Nosology and Classification of Genetic Skeletal Disorders provides an overview of recognized diagnostic entities and groups them by clinical and radiographic features and molecular pathogenesis. The aim is to provide the Genetics, Pediatrics and Radiology community with a list of recognized genetic skeletal disorders that can be of help in the diagnosis of individual cases, in the delineation of novel disorders, and in building bridges between clinicians and scientists interested in skeletal biology. In the 2010 revision, 456 conditions were included and placed in 40 groups defined by molecular, biochemical, and/or radiographic criteria. Of these conditions, 316 were associated with mutations in one or more of 226 different genes, ranging from common, recurrent mutations to "private" found in single families or individuals. Thus, the Nosology is a hybrid between a list of clinically defined disorders, waiting for molecular clarification, and an annotated database documenting the phenotypic spectrum produced by mutations in a given gene. The Nosology should be useful for the diagnosis of patients with genetic skeletal diseases, particularly in view of the information flood expected with the novel sequencing technologies; in the delineation of clinical entities and novel disorders, by providing an overview of established nosologic entities; and for scientists looking for the clinical correlates of genes, proteins and pathways involved in skeletal biology. Warman et al., "Nosology and classification of genetic skeletal disorders: 2010 revision" *Am J Med Genet A* 155A(5):943-968 (2011).

E. Muscular Disorders

Skeletal muscle is the largest organ in the human body, and plays an important role in body movement and metabolism. Skeletal muscle mass is lost in genetic disorders such as muscular dystrophy, muscle wasting and ageing. Chemicals and proteins that restore muscle mass and function are potential drugs that can improve human health and could be used in the clinic. Myostatin is a muscle-specific member of the transforming growth factor (TGF)-beta superfamily that plays an essential role in the negative regulation of muscle growth. Inhibition of myostatin activity is a promising therapeutic method for restoring muscle mass and strength. Potential inhibitors of myostatin include follistatin domain-containing proteins, myostatin propeptide, myostatin antibodies and chemical compounds. These inhibitors could be beneficial for the development of clinical drugs for the treatment of muscular disorders. Bone morphogenetic protein (BMP) plays a significant role in the development of neuromuscular architecture and its proper functions. Modulation of BMP activity could be beneficial for muscle function in muscular disorders. Tsuchida K., "The role of myostatin and bone morphogenetic proteins in muscular disorders" *Expert Opin Biol Ther.* 6(2):147-154 (2006).

Currently, the diagnosis of muscular disorders is mainly clinical, wherein myopathies can present with unusual or atypical clinical features including, but not limited to, myotonia, periodic paralysis, respiratory failure, swallowing difficulties, ptosis, ophtalmoplegia, camptocormia, distal and/or asymmetrical limb muscle weakness. Several recently discovered myopathies include, but are not limited to, reducing body myopathy, X-linked myopathy with postural muscle atrophy, Emery-Dreifuss muscular dystrophy, and scapuloperoneal myopathy.

F. Cardiovascular Disorders

Dyslipidemias and insulin resistance constitute major risk factors of cardiovascular diseases (CVD) and related-features. Furthermore, oxidative stress impairment or altered antioxidant status have been suggested as pivotal keys in the onset of certain chronic diseases such as metabolic syndrome (MS), type 2 diabetes and CVD. In this sense, oxidized low-density lipoprotein (ox-LDL), a recognized oxidative stress marker, has been positively associated with central obesity, metabolic syndrome manifestations and subclinical atherosclerosis. Hermsdorff H., *Nutrition & Metabolism* 8:59 (2011).

EXPERIMENTAL

Example I

Preparation of Conventional Phospholipid Krill Oil

Krill oil compositions contemplated herein were prepared from freshly caught whole krill. A PPC material was obtained from fresh krill using an enzymatic hydrolysis process, involving shell removal, removal of water-soluble peptides and vacuum drying at a low temperature followed by a 40% ethanol in water extraction. The process is carried out immediately after catch to ensure that only fresh krill is used, resulting in less degradation and higher quality PPC. The phospholipid concentration of the extracted krill oil ranged between approximately 60-99% and a viscosity ranging between 100,000-3,000,000 cP.

Example II

Preparation of a Lyophilized Concentration Krill Oil

A mixture comprising krill oil, water and ethanol produced in accordance with Example I is subjected to lyophilization using a commercially available lyophilizer to produce a lyophilized krill oil. Such a lyophilized krill oil comprises a semi-solid composition including, but not limited to, phospholipids, fatty acids, omega-3, EPA and DHA having flowability characteristics at a temperature of at least 40° C.

Example III

Krill Oil Viscosity Measurements

Krill oil viscosity was measured using a Brookfield Rotary Dial viscometer at 35° C. and the values were reported as centipoise (cP).

Example IV

Krill Oil Phospholipid Measurements

The phospholipid levels were measured using the method described in the reference with 31P-NMR spectroscopy. Amidon et al., "A theoretical basis for a biopharmaceutics drug classification: the correlation of in vitro drug product dissolution and in vivo bioavailability" *Pharm. Res.* 12:413-420 (1995).

Example V

Preparation of a Lyophilized Concentrated Krill Oil

A krill oil produced in accordance with Example I is subjected to lyophilization using a commercially available lyophilizer to produce a lyophilized krill oil product in accordance with Example II.

Example VI

Capsule Filling with a Flowable Concentrated Phospholipid Semi-Solid Krill Oil

Five thousand capsules are filled with a flowable/concentrated phospholipid semi-solid krill oil having a phospholipid concentration ranging between 60-99%, a water content between 1-4% and an organic solvent less than 1% using a commercially available capsule filling machine (e.g., for example, Robert Bosch GmbH GKF 1400 L). The capsule filling machine may accommodate either hard gelatin capsules and soft gel capsules, where the production run is completed with a leakage rate of between approximately 0.1-3%

Example VII

Viscosity of Oxidized Krill Oil

Objectives
 1. To investigate if thermal treatment could increase the viscosity of krill oil, which might be resulted from the increase of lipid oxidation and subsequently increase also the oxypolymerization.

Experimental Design
Krill oil (Rimfrost®, Rimfrost AS (formerly Olympic Seafoods, AS) were incubated at different temperatures (20 and 40° C.) for approximately 1, 2, 3, 4 and 6 weeks, under condition of constant stirring while being exposed to air (semi-open air condition). Below is the experimental design from previous experiment.

| Storage time | | Temperature (° C.) | |
|---|---|---|---|
| Weeks | days | 20 | 40 |
| | 0 | K2000 | K4000 |
| | 1 | K2001* | K4001* |
| | 3 | K2003 | K4003 |
| 1 | 7 | K2007 | K4007 |
| 2 | 14 | K2014 | K4014 |
| 3 | 21 | K2021 | K4021 |
| 4 | 28 | K2028* | K4028 |
| 6 | 48 | K2048* | K4042* |

*Samples upon which viscosity was measured.

Method of Measurement
The viscosity of krill oil (1-2 g) was measured by rheometer (Haake Mars Modular Advanced System, Thermo Fisher) at temperature 23° C. by using Sensor plate P 35 Til S (serrated), with shear rate (1/s) from 10-1000.

Figure 6:
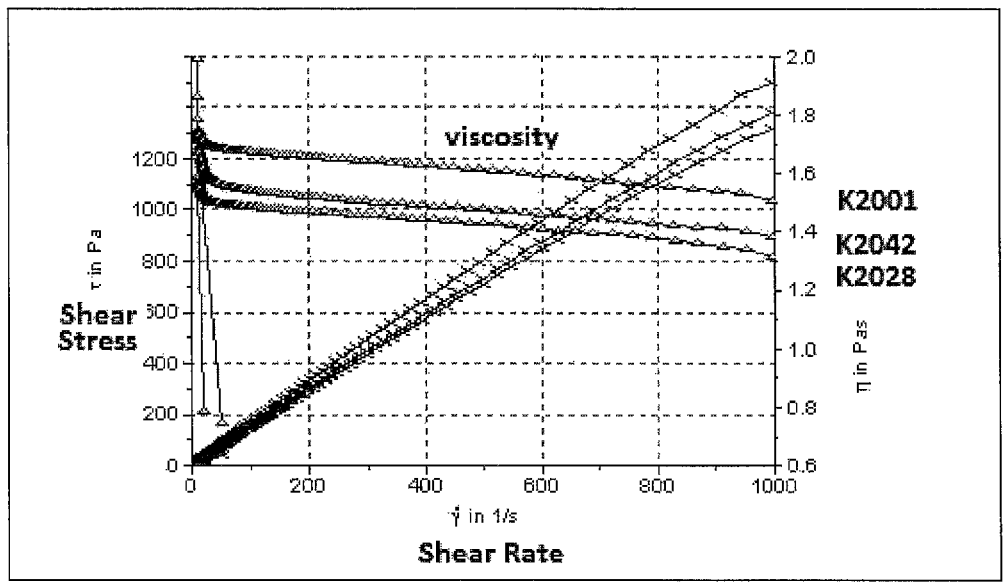
FIG. 6 presents exemplary data measuring shear stress and shear rate of krill oil incubated at 20° C.

Overall Observation
The highest degree of viscosity index was obtained for krill oil incubated at 40° C. after 42 days of storage. The increase of lipid oxidation seemed to increase the oxypolymerisation in krill oil as illustrated by the increase of viscosity index of krill oil. See, Table 15; FIGS. 5 and 6.

TABLE 15

Viscosity index of krill oil incubated at different temperatures

| Samples | Viscosity index (Pa · s) | Mean (Pa · s) |
|---|---|---|
| K2001 | 1.847 | 1.846 ± 0.001 |
| | 1.845 | |
| K2028 | 1.849 | 1.772 ± 0.180 |
| | 1.594 | |
| K2042 | 1.821 | 1.807 ± 0.020 |
| | 1.793 | |
| K4001 | 1.592 | 1.746 ± 0.140 |
| | 1.775 | |
| | 1.872 | |
| K4042 | 2.085 | 2.083 ± 0.070 |
| | 2.149 | |
| | 2.016 | |

Example VIII

Comparison of Acetone and Ethanol Fractionation of Krill Oil

Materials
Commercial krill oil, Rimfrost®, was obtained from Olympic Seafood AS, Fosnavåg, Norway. Pure ethanol (100%) was purchased from Arcus Kjemi A S, Vestby, Norway. Acetone used in the extraction process was of HPLC quality (LiChrosolv®, 99.8%; Merck, Damstadt, Germany). All solvents and reagents for the analyses were of analytical grade.

Chemical Analyses
Lipid class analyses were performed by a HPLC system (Perkin-Elmer, Waltham, USA) equipped with an ESA Corona® Plus Charged Aerosol Detector (ESA Biosciences, Inc., Chelmsford, USA) (Moreau, 2006). The samples were separated on a LiChrosphere® 100, 5 μm diol column, 4×125 mm (Merck KGaA, Germany). A ternary gradient consisting of solvent A=isooctane, B=acetone/diclormetane (1:2) and C=2-propanol/methanol/acetic acid-ethanolamine-water (7.5 mM ethanolamine and 7.5 mM acetic acid) (85:7.5:7.5) was used with the following profile: at 0 min, 100:0:0 (% A:% B:% C); at 1 min, 90:10:0; at 8 min 70:30:0;

at 11 min 40:50:10; at 13 min 39:0:61; at 26.3 min 40:0:60; at 28.4 min 0:100:0; at 30.9 min 100:0:0. The lipid components were identified by comparison to the retention time of commercial standards.

Sodium chloride (NaCl) content was determined based on water soluble chloride. "Method 937.09"; In: *Official Methods of Analysis,* 18th ed. Association of Official Analytical Chemists, Gaithersburg, Md. (2005). Trimethylamine N-oxide (TMAO) and trimethylamine (TMA) were determined based on a previously reported micro-diffusion technique. Conway et al., "An absorption apparatus for the microdetermination of certain volatile substances: The microdetermination of ammonia" *The Biochemical Journal* 27(2): 419-429 (1933). Lipid content was determined by choloroform-methanol extraction. Bligh et al., "A rapid method for total lipid extraction and purification" *Canadian Journal of Biochemistry and Physiology* 37(8):911-917 (1959).

Fatty acid composition was analyzed according to a published method. "Fatty acid composition by GLC. Marine oils" (Method Ce 1b-89) In: Official Methods and Recommended Practices of the AOCS, 5th ed.; Firestone, D., Ed.; AOCS Press: Champaign, Ill., 1998. C23:0 methyl ester was added as internal standard. The fatty acid methyl esters were separated by gas chromatography fitted with a 1.5 m×0.25 mm pre column (VSD Tubing, SGE, i.d. 363 μm) connected to a 60 m×0.25 mm i.d., 0.25 μm stationary phase capillary BPX70 column (Cyano propyl, SGE), using a Thermo Trace GC Ultra gas chromatograph equipped with an AS 2000 autosampler, splitless injector, and flame ionization detector (Thermo Scientific, Milan, Italy). Helium at 70 kPa injector pressure was used as carrier gas. Injection (1.0 μL) was done at 60° C. The temperature profile used was 60° C. for 4 min, 30° C./min to 176° C., 1.5° C./min to 230° C., 119.9° C./min to 250° C. for 7 min. Fatty acid composition was calculated by use of the internal standard method and reported on a sample basis as grams of fatty acid methyl esters per 100 gram. Analyses were run in duplicate.

Acetone Fractionation

The krill oil (20 gram) was extracted with 150 ml acetone. The mixture was heated in a water bath to 45° C. under periodic mixing by use of a glass rod and cooled on an ice/water bath for 30 minutes before 5 minutes centrifugation at 2000 rpm and 5° C. The acetone was decanted and the acetone insoluble fraction extracted a second time with 150 ml cooled acetone on an ice/water bath. The used acetone was pooled and evaporated under vacuum at 45° C. and 300 mbar pressure to collect the acetone soluble fraction. Acetone insoluble matter was dried on a water bath (35° C.) under continuous nitrogen flushing for 2 hours. Amount of krill oil and the respective fractions were measured to establish a mass balance. Triplicate measurements were performed.

Ethanol Fractionation

Krill oil (50 g) was added to ethanol (150 g) in a 250 ml centrifugation bottle and conditioned at 35° C. for one hour with intermittent mixing. The bottle was placed in a controlled temperature circulation bath for 21 hours before separation of solids by centrifugation at 10,000 rpm for 10 minutes. Centrifugation was performed at the equivalent temperature level to avoid any change in lipid partitioning. The supernatant was decanted off and ethanol removed on a rotavapour at 45° C. and 50 mbar pressure. Ethanol in the solid phase was removed on a rotavapor at 45° C. and 50 mbar pressure. Weight and yield of lipids in the two phases where recorded. The samples were stored at −80° C. before analysis.

Statistical Analysis

Principal component analysis (PCA) was performed in Unscrambler v.10.3 (CAMO Software AS, Oslo, Norway) based on mean centered and standardized process and response variables. Possible outlier samples were identified based on the default settings of the PCA module. The experimental data were fitted to a second-order polynomial (Eq. 1) by means of response surface methodology (RSM) with the assistance of STATISTICA (v. 12.0) from Statsoft v.13 (Tulsa, Okla., USA). Meyers et al., "Response Surface Methodology. Process and Product Optimization Using Designed Experiments" John Wiley & Sons, New York, N.Y. (USA) (2002). In the model, y is the estimated response (i.e., yield of lipid class and astaxanthin in the ethanol phase), $\beta_0$ the intercept, $\beta_1$ and $\beta_2$, $\beta_{11}$ and $\beta_{22}$ and $\beta_{12}$ the regression coefficients of each factor, of each quadratic term and of the interaction term between them, respectively, is the residual (error) and xi the independent variables (K and water content):

$$y=\beta_0+\beta_1 x_1+\beta_2 x_2+\beta_{11} x_1^2+\beta_{22} x_2^2+\beta_{12} x_1 x_2+\varepsilon \quad \text{(Eq. 1)}$$

The responses were fitted to the independent variables by multiple regressions, and the best subset model was identified based on backward removal of insignificant regressors (p, remove 0.05). The quality of the fitted models were evaluated based on ANOVA, F-statistics and the coefficient of multiple determination (R2). Possible outlier observations were identified based on normal probability plot of studentized Y-residuals.

SUPPLEMENTAL REFERENCES

Wu, C. and L. Z. Benet, Predicting drug disposition via application of BCS: transport/absorption/elimination interplay and development of a biopharmaceutics drug disposition classification system, Pharm. Res. 22 (2005) 11-23.

Lipinski, C. and F. Lombardo, B. W. Dominy, P. J. Feeney, Experimental and computational approaches to estimate solubility and permeability in drug discovery and development settings, Adv. Drug Deliv. Rev. 46 (2001) 3-26.

Charman, S. W. N. Channan, M. C. Rogge, T. D. Wilson, F. J. Dutko, C. W. Pouton, Self-emulsifying drug delivery systems: formulation and biopharmaceutic evaluation of an investigational lipophilic compound, Pharm. Res. 9 (1992) 87-93.

H. Seager, Soft Gelatin Capsules: a Solution to Many Tableting Problems, Pharm. Tech. 9 (1985) 84, 86, 88, 90, 92, 94, 96, 98, 100, 102, 104. F. Podczek, Technology to manufacture soft capsules, in: F. Podczek, B. E. Jones (Eds.), Pharmaceutical Capsules, Pharmaceutical Press, London, 2004, pp. 195-199.

G. Fischer, Weichgelatinekapseln, in: H. Sucker, P. Fuchs, P. Speiser (Eds.), Pharmazeutische Technologie, Georg Thieme Verlag, Stuttgart, 1991, pp. 337-347.

D. H. Bergstrom, R. P. Waranis, M. S. Rahman, J. C. Ferdinando, Capsules, soft, in: J. Swarbrick, J. C. Boylan (Eds.), Encyclopedia of Pharmaceutical Technology, Marcel Dekker, New York, 2002, pp. 317-327.

P. Ghirardi, G. Catenazzo, O. Mantero, G. C. Merotti, A. Marzo, Bioavailability of digoxin in a new soluble pharmaceutical formulation in capsules, J. Pharm. Sci. 66 (1977) 267-269.

H. Ooi, W. S. Colucci, Pharmacological treatment of heart failure, in: J. G. Hardman, L. E. Limbird (Eds.), Goodman & Gilman's The pharmacological basis of therapeutics, McGraw-Hill, New York, 2001, p. 918.

S. E. Walker, K. Bedford, T. Eaves, Improvements in and Relating to Pharmaceutical Preparations in Solid Unit Dosage Form, British Patent 1 572 226, 1980.

C. McTaggart, R. Wood, K. Bedford, S. E. Walker, The evaluation of an automatic system for filling liquids into hard gelatin capsules, J. Pharm. Pharmacol. 36 (1984) 119-121.

A. Cuiné, C. Mathis, A. Stamm, D. François, Das Einbringen viskoser Lösungen von Aktivstoffen in Hartgelatinekapseln, Pharm. Ind. 40 (1987) 654-657.

W. Lahr, Flüssig befüllte Hartgelatinekapseln, Pharm. Ztg. 131(1986) 871-874.

R. Hermann, Bioverfügbarkeit zweier neuer Nifedipin-Formulieningen, Pharm. Ztg. 131 (1986) 869-870.

N. Yessksel, A. Karatay, Y. Ozkan, A. Savayer, S. A. Ozkan, T. Baykara, Enhanced bioavailability of piroxicam using Gelucire 44/14 and Labrasol: in vitro and in vivo evaluation, Eur. J. Pharm. Biopharm. 56 (2003) 453-459.

K. Schamp, S-A. Schreder, J. Dressman, Development of an in vitro/in vivo correlation for lipid formulations of EMD 50733, a poorly soluble, lipophilic drug substance, Eur. J. Pharm. Biopharm. 62 (2006) 227-234.

H. N. Joshi, R. W. Tejwani, M. Davidovich, V. P. Sahasrabudhe, M. Jemal, M. S. Bathala, S. A. Varia, A. T. M. Serajuddin, Bioavailability enhancement of a poorly water-soluble drug by solid dispersion in polyethylene glycolpolysorbate 80 mixture, Int. J. Pharm. 269 (2004) 251-258.

M. S. Soliman, M. A. Khan, Preparation and in vitro characterization of a semi-solid dispersion of flurbiprofen with Gelucire 44/14 and Labrasol, Phanuazie 60 (2005) 288-293.

C. W. Pouton, Formulation of poorly water-soluble drugs for oral administration: physicochemical and physiological issues and the lipid formulation classification system, Eur. J. Pharm. Sci. 1452 (2006) 1-10.

H. Benameur, Liquid and semi-solid foimulations for enhancing oral absorption, Bull. Tech. Gattefossé 99 (2006).

M. Dürr, H. U. Fridolin, K. D. Gneuss, Entwicklung von Rezepturen und Verfahren zur Abfüllung von flüssigen Massen in Hartgelatinekapseln unter Produktionsbedingungen, Acta Pharm. Technol. 29 (1983) 245-251.

S. E. Walker, J. A. Ganley, K. Bedford, T. Eaves, The filling of molten and thixotropic formulations into hard gelatin capsules, J. Pharm. Pharmacol. 32 (1980) 389-393.

W. J. Bowtle, S. L. Burrows, E. D. Holmes, B. E. Jones, S.S.M. formulations and capsules: an improved way to handle toxic compounds, AAPS annual meeting and exposition, Pharm. Res. 7 (1989) 612 (Poster P T).

C. Doelker, E. Doelker, P. Buri, The incorporation and in vitro release profile of liquid, deliquescent or unstable drugs with fusible excipients in hard gelatin capsules, Drug Dev. Ind. Pharm. 12 (1986) 1553-1565.

W. J. Bowtle, N. J. Barker, J. Woodhams, A new approach to vancomycinformulation using filling technology for semi-solid matrix capsules, Pharm. Technol. 12 (1988) 86-97.

R. A. Lucas, W. J. Bowtle, R. Ryden, Disposition of vancomycin in healthy volunteers from oral solution and semi-solid matrix capsules, J. Clin. Pharm. Ther. 12 (1987) 27-31.

J. R. Howard, P. L. Gould, Drug release from thermosetting fatty vehicles filled into hard gelatin capsules, Drug Dev. Ind. Pharm. 13 (1987) 1031-1045.

A. B. Dennis, S. J. Farr, I. W. Kellaway, G. Taylor, R. Davidson, In vivo evaluation of rapid release and sustained release Gelucire capsule formulations, Int. J. Pharm. 65 (1990) 85-100.

A. C. Vial-Bernasconi, P. Buri, E. Doelker, E. Beyssac, G. Duchaix, J. M. Aiache, In vivo evaluation of an indomethacin monolithic, extended zeroorder release hard gelatin capsule formulation based on saturated polyglycolysed glycerides, Pharm. Acta Helv. 70 (1995) 307-313.

Y. Seta, F. Higuchi, Y. Kawahara, K. Nishimura, R. Okada, Design and preparation of captopril sustained-release dosage forms and theirbiopharmaceutical properties, Int. J. Pharm. 41(1988) 245-254.

Y. Seta, F. Higuchi, T. Otsuka, Y. Kawahara, K. Nishimura, R. Okada, H. Koyke, Preparation and pharmacological evaluation of captopril sustainedrelease dosage forms using oily semi-solid matrix, Int. J. Pharm. 41(1988) 255-262.

Y. Seta, T. Otsuka, H. Tokiwa, H. Naganuma, Y. Kawahara, K. Nishimura, R. Okada, Design of captopril sustained-release preparation with oily semisolid matrix, Int. J. Pharm. 41(1988) 263-269.

T. Baykara, N. Yuksel, The preparation of prolonged action formulations in the form of semi-solid matrix into hard gelatin capsules of oxyprenolol. I. Thetmocap method, Drug Dev. Ind. Pharm. 17 (1991) 1215-1227.

E. T. Cole, R. A. Scott, D. Cade, A. L. Connor, I. R. Wilding, In vitro and in vivo pharmacoscintigraphic evaluation of ibuprofen hypromellose and gelatin capsules, Pharm. Res. 21(2004) 793-798.

N. A. Armstrong, K. C. James, W. K. L. Pugh, Drug migration into soft gelatin capsule shells and its effect on in vitro availability, J. Pharm. Pharmacol. 36 (1984) 361-365.

J. M. Kovarik, E. A. Muller, J-B. Van-Bree, W. Tetzloff, K. Kutz, Reduced inter- and intraindividual variability in cyclosporin pharmacokinetics from a microemulsion formulation, J. Pharm. Sci. 83 (1994) 444-146.

R. G. Strickley, Solubilizing excipients in oral and injectable formulations, Pharm. Res. 21(2004) 201-230.

C. M. Bond, K. A. Lees, J. L. Packington, Cephalexin: a new oral broadspectrum antibiotic, Pharm. J. 205 (1970) 210-214.

M. J. Kontny, C. A. Mulski, Gelatin capsule brittleness as a function of relative humidity at room temperature, Int. J. Pharm. 54 (1989) 79-85.

R. K. Chang, K. S. Raghavan, M. A. Hussain, A study on gelatin capsule brittleness: moisture transfer between the capsule shell and its content, J. Pharm. Sci. 87 (1998) 556-558.

M. Kuentz, D. Röthlisberger, Determination of the optimal amount of water in liquid-fill masses for hard gelatin capsules by means of texture analysis and experimental design, Int. J. Pharm. 236 (2002) 145-152.

D. Cadé, N. Madit, Liquid filling in hard gelatin capsules—preliminary steps, Bulletin Technique Gattefossé, 89 (1996) 15-19.

G. A. Digenis, T. B. Gold, V. P. Shah, Cross-linking of gelatin capsules and its relevance to their in vitro-in vivo performance, J. Pharm. Sci. 83 (1994) 915-921.

M. Dey, R. Enever, M. Kraml, D. G. Prue, D. Smith, R. Weierstall, The dissolution and bioavailability of etodolac from capsules exposed to conditions of high relative humidity and temperature, Pharm. Res. 10 (1993) 1295-1300.

E. T. Cole, N. Madit, D. Cadé, Method of stressing hard gelatin capsules, AAPS Annual Meeting & Exposition, Symposia Abstracts, Nov. 2-6, 1997, p. 101.

C. B. Bottom, J. Clark, J. S. Green, L. J. Starcevich, Stressing methods and dissolution of cross-linked soft gelatin capsules, AAPS Annual Meeting & Exposition, Symposia Abstracts, Nov. 2-6, 1997, p. 102.

J. Brown, N. Madit, E. T. Cole, I. R. Wilding, D. Cadé, The effect of crosslinking on the in vivo disintegration of hard gelatin capsules, Pharm. Res. 15 (1998) 1026-1030.

M. C. Meyer, A. B. Straughn, R. M. Mhatre, A. Hussain, V. P. Shah, C. B. Bottom, E. T. Cole, L. L. Lesko, H. Mallinowski, R. L. Williams, The effect of gelatin cross-linking on the bioequivalence of hard and soft gelatin acetaminophen capsules, Pharm. Res. 17 (2000) 962-966.

S. M. Chatham, The use of bases in semi-solid matrix formulations, S.T.P. Pharma 3 (1987) 575-582.

F. Wittwer, New developments in hermetic sealing of hard gelatin capsules, Pharm. Manuf. 2 (1985) 24-27.

b1151N Pharmaceutical Dosage Forms, USP 30-NF 25, 2007, pp. 620-631.

W. J. Bowtle, Liquid filling of hard gelatin capsules: a new technology for alternative formulations, Pharm. Tech. Eur. 10 (1998) 84-90.

We claim:

1. A semi-solid krill oil comprising a phospholipid content ranging between approximately 60%-99% (w/w), a water content ranging between 1-4% (w/w) and an organic solvent content of less than 1%, wherein said semi-solid krill oil is at a temperature of between at least 40° C. and a maximum of approximately 70° C.

2. The krill oil of claim 1, wherein said organic solvent is ethanol.

3. The krill oil of claim 1, wherein said krill oil further comprises a viscosity ranging between approximately 100,000-3,000,000 cP.

4. The krill oil of claim 1, wherein said krill oil is a gently dried krill oil.

5. The krill oil of claim 4, wherein said gently dried krill oil is a lyophilized krill oil.

6. The krill oil of claim 1, wherein said krill oil is encapsulated.

7. The krill oil of claim 1, wherein said phospholipid content comprising phosphatidylcholine in a range of approximately 35-55% (w/w), alkyl acyl phosphatidylcholine in a range of approximately 3.0-6.0% (w/w), phosphatidylinositol in a range of approximately 0.5-0.9% (w/w), phosphatidylserine (PS) in a range of approximately 0.3-0.6%, lysophosphatidylcholine in a range of approximately 1.5-4.0%, lyso alkyl acyl phosphatidylcholine in a range of approximately 1.0-0.25%, phosphatidylethanolamine in a range of approximately 2.0-4.0%, alkyl acyl phosphatidylethanolamine in a range of approximately 0.25-1.25%, cardiolipin+N-acylphosphatidylethanolamine in a range of approximately 0.5-2.5%, lysophosphatidylethanolamine in a range of approximately 0.2-0.6%, and lyso alkyl acyl phosphatidylethanolamine of <0.1%.

8. The krill oil of claim 6, wherein said encapsulated krill oil comprises a capsule selected from the group consisting of a soft gel capsule and a hard gelatin capsule.

9. A capsule comprising a semisolid krill oil having a phospholipid content ranging between approximately 60%-99% (w/w), a water content ranging between 1-4% (w/w) and an organic solvent content of less than 1%, wherein said capsule is at a temperature of between at least 40° C. and a maximum of approximately 70° C.

10. The capsule of claim 9, wherein said organic solvent is ethanol.

11. The capsule of claim 9, wherein said krill oil comprises a viscosity ranging between approximately 100,000-3,000,000 cP.

12. The capsule of claim 9, wherein said krill oil is a gently dried krill oil.

13. The capsule of claim 12, wherein said gently dried krill oil is a lyophilized krill oil.

14. The capsule of claim 9, wherein said phospholipid content comprises phosphatidylcholine in a range of approximately 35-55% (w/w), alkyl acyl phosphatidylcholine in a range of approximately 3.0-6.0% (w/w), phosphatidylinositol in a range of approximately 0.5-0.9% (w/w), phosphatidylserine (PS) in a range of approximately 0.3-0.6%, lysophosphatidylcholine in a range of approximately 1.5-4.0%, lyso alkyl acyl phosphatidylcholine in a range of approximately 1.0-0.25%, phosphatidylethanolamine in a range of approximately 2.0-4.0%, alkyl acyl phosphatidylethanolamine in a range of approximately 0.25-1.25%, cardiolipin+N-acylphosphatidylethanolamine in a range of approximately 0.5-2.5%, lysophosphatidylethanolamine in a range of approximately 0.2-0.6%, and lyso alkyl acyl phosphatidylethanolamine of <0.1%.

* * * * *